(12) United States Patent
Yamada et al.

(10) Patent No.: US 10,096,786 B2
(45) Date of Patent: Oct. 9, 2018

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Yui Yamada, Kanagawa (JP); Hideko Inoue, Kanagawa (JP); Hiromi Seo, Kanagawa (JP); Tatsuyoshi Takahashi, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 228 days.

(21) Appl. No.: 14/974,142

(22) Filed: Dec. 18, 2015

(65) Prior Publication Data

US 2016/0181550 A1    Jun. 23, 2016

(30) Foreign Application Priority Data

Dec. 19, 2014 (JP) ................................ 2014-256995

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC ............. H01L 51/0084; H01L 51/0085; H01L 51/0087; H01L 51/5012; H01L 51/5016;
(Continued)

(56) References Cited

U.S. PATENT DOCUMENTS 7,649,077 B2    1/2010 Craig et al.
8,012,602 B2    9/2011 Schäfer et al.
(Continued)

FOREIGN PATENT DOCUMENTS

JP    2008-69221       3/2008
JP    2010-182699 A    8/2010
(Continued)

OTHER PUBLICATIONS

Antonio, H. et al. "The reaction of Tetralones with Nitriles: A Simple Approach to the Synthesis of New Substituted benzo[h]quinazolines, benzo[f]quinazolines and dibenzo[a,i]phenanthridines," Tetrahedron, 2006, vol. 62, Issue 12, pp. 2799-2811.

*Primary Examiner* — Susan D Leong
(74) *Attorney, Agent, or Firm* — Husch Blackwell LLP

(57) ABSTRACT

To provide an organometallic complex with high emission efficiency and high heat resistance, which emits yellow green light. The organometallic complex includes a metal and a ligand which is a benzo[h]quinazoline skeleton including a condensed ring bonded to benzo[h]quinazoline through a carbon-carbon bond between the 5-position and the 6-position. The organometallic complex has a structure represented by General Formula (G1). In General Formula (G1), M represents a metal belonging to Group 9 or 10; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

(Continued)

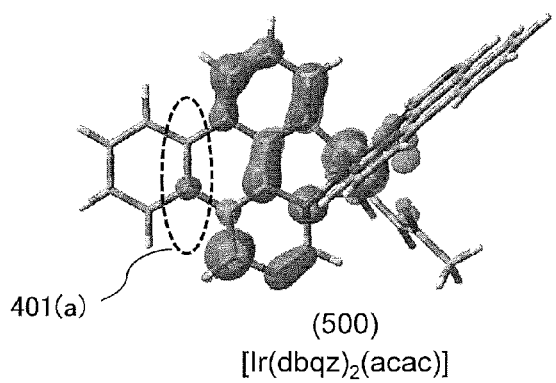

401(a)

(500)

[Ir(dbqz)₂(acac)]

(G1)

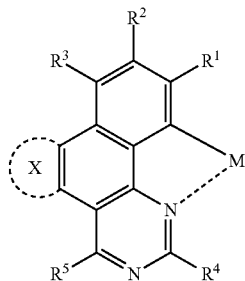

14 Claims, 29 Drawing Sheets

(51) Int. Cl.
*C07F 15/00* (2006.01)
*H01L 51/50* (2006.01)
(52) U.S. Cl.
CPC ............... *C09K 2211/1007* (2013.01); *C09K 2211/1029* (2013.01); *C09K 2211/1044* (2013.01); *C09K 2211/185* (2013.01); *H01L 51/5016* (2013.01)

(58) Field of Classification Search
CPC ............ C09K 11/06; C09K 2211/1044; C09K 2211/185; C07F 15/0033; C07F 15/006; C07F 15/0073; C07F 15/0086
See application file for complete search history.

(56) References Cited

U.S. PATENT DOCUMENTS

| | | | |
|---|---|---|---|
| 8,921,548 B2 | 12/2014 | Inoue et al. | |
| 9,147,849 B2 | 9/2015 | Nam et al. | |
| 9,184,398 B2 | 11/2015 | Inoue et al. | |
| 9,444,059 B2* | 9/2016 | Inoue | H01L 51/0085 |
| 2007/0122655 A1 | 5/2007 | Deaton et al. | |
| 2010/0240892 A1 | 9/2010 | Schafer et al. | |
| 2012/0211701 A1* | 8/2012 | Spreitzer | C07B 59/00 252/301.16 |
| 2013/0079517 A1 | 3/2013 | Schafer et al. | |
| 2014/0231770 A1* | 8/2014 | Inoue | H01L 51/0085 257/40 |
| 2014/0332758 A1 | 11/2014 | Kwong et al. | |

FOREIGN PATENT DOCUMENTS

| | | |
|---|---|---|
| JP | 2011-181660 | 9/2011 |
| JP | 2013-53158 | 3/2013 |
| KR | 2012-0117693 A | 10/2012 |
| WO | WO 2000/070655 A2 | 11/2000 |
| WO | WO 2013/180376 A1 | 12/2013 |

\* cited by examiner

401(a)

(500)
[Ir(dbqz)₂(acac)]

401(b)

(600)
[Ir(bqn)₂(acac)]

(500)
[Ir(dbqz)₂(acac)]

(600)
[Ir(bqn)₂(acac)]

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic complex, particularly, to an organometallic complex capable of converting triplet excitation energy into light emission. In addition, one embodiment of the present invention relates to a light-emitting element, a light-emitting device, an electronic device, and a lighting device each including the organometallic complex.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a power storage device, a memory device, an imaging device, a method for driving any of them, and a method for manufacturing any of them.

2. Description of the Related Art

In recent years, research and development have been extensively conducted on light-emitting elements using electroluminescence (EL). In the basic structure of such a light-emitting element, a layer containing a light-emitting substance (an EL layer) is interposed between a pair of electrodes. By applying a voltage to this element, light emission from the light-emitting substance can be obtained.

Since the above light-emitting element is a self-luminous type, a display device using this light-emitting element has advantages such as high visibility, no necessity of a backlight, and low power consumption. Furthermore, such a light-emitting element also has advantages in that it can be fainted to be thin and lightweight and has high response speed.

In the case of an organic EL element in which an EL layer containing an organometallic complex as a light-emitting substance is provided between a pair of electrodes, application of a voltage between the pair of electrodes causes injection of electrons from a cathode and holes from an anode into the EL layer having a light-emitting property, and thus, a current flows. By recombination of the injected electrons and holes, the organometallic complex is raised to an excited state to provide light emission.

The excited state of the organometallic complex can be a singlet excited state ($S_1$) or a triplet excited state ($T_1$), and light emission from the singlet excited state is referred to as fluorescence and light emission from the triplet excited state is referred to as phosphorescence. The statistical generation ratio thereof in the light-emitting element is considered to be $S_1:T_1=1:3$.

Among the organometallic complexes, a compound capable of converting singlet excitation energy into light emission is called a fluorescent compound (fluorescent material), and a compound capable of converting triplet excitation energy into light emission is called a phosphorescent compound (phosphorescent material).

The internal quantum efficiency (the ratio of the number of generated photons to the number of injected carriers) of a light-emitting element including a fluorescent material is thought to have a theoretical limit of 25%, on the basis of $S_1:T_1=1:3$, while the internal quantum efficiency of a light-emitting element including a phosphorescent material is thought to have a theoretical limit of 75%.

In other words, a light-emitting element including a phosphorescent material has higher emission efficiency than a light-emitting element including a fluorescent material. Therefore, a phosphorescent material capable of converting triplet excitation energy into light emission has been actively developed in recent years. An organometallic complex that contains iridium or the like as a central metal is particularly attracting attention because of its high phosphorescence quantum yield. For example, an organometallic complex that contains iridium as a central metal is disclosed as a phosphorescent material in Patent Documents 1 and 2.

REFERENCE

Patent Document

[Patent Document 1] Japanese Published Patent Application No. 2013-053158
[Patent Document 2] Japanese Published Patent Application No. 2008-069221

SUMMARY OF THE INVENTION

Although phosphorescent materials exhibiting various emission colors have been developed as disclosed in Patent Documents 1 and 2, development of a novel organometallic complex with higher efficiency has been desired.

In view of the above, an object of one embodiment of the present invention is to provide a novel organometallic complex capable of emitting phosphorescence. Another object is to provide a novel organometallic complex capable of emitting blue green to yellow green phosphorescence. Another object is to provide a novel organometallic complex with high emission efficiency. Another object is to provide a novel organometallic complex with high heat resistance. Another object is to provide a light-emitting element, a light-emitting device, an electronic device, or a lighting device including the novel organometallic complex.

Another object is to provide a light-emitting element, a light-emitting device, an electronic device, or a lighting device with high emission efficiency. Another object is to provide a light-emitting element, a light-emitting device, an electronic device, or a lighting device with high reliability. Another object is to provide a light-emitting element, a light-emitting device, an electronic device, or a lighting device with low power consumption. Another object is to provide a novel light-emitting element, light-emitting device, electronic device, or lighting device.

Note that the description of these objects does not disturb the existence of other objects. In one embodiment of the present invention, there is no need to achieve all the objects. Other objects will be apparent from and can be derived from the description of the specification, the drawings, the claims, and the like.

One embodiment of the present invention is an organometallic complex including a metal belonging to Group 9 or 10 of the periodic table and a benzo[h]quinazoline skeleton. The benzo[h]quinazoline skeleton includes a condensed ring (fused) structure that is bonded to benzo[h]quinazoline through a carbon-carbon bond of the 5- and the 6-position (a carbon-carbon bond including carbon in the 5-position and carbon in the 6-position). The benzo[h]quinazoline skeleton is bonded to the metal.

Another embodiment of the present invention is an organometallic complex including a metal belonging to Group 9 or 10 of the periodic table, a first ligand, and a second ligand. The first ligand is a benzo[h]quinazoline skeleton. The benzo[h]quinazoline skeleton includes a condensed ring structure that is bonded to benzo[h]quinazoline through a carbon-carbon bond of the 5- and the 6-position. The second ligand is a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two coordinating elements are both nitrogen. The benzo[h]quinazoline skeleton that is the first ligand is bonded to the metal, and the second ligand is bonded to the metal.

Another embodiment of the present invention is an organometallic complex including a structure represented by General Formula (G1).

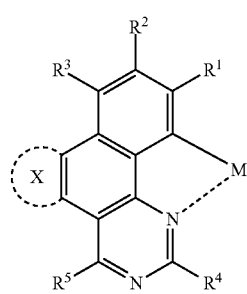

In General Formula (G1), M represents a metal belonging to Group 9 or 10 of the periodic table; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

Another embodiment of the present invention is an organometallic complex represented by General Formula (G2).

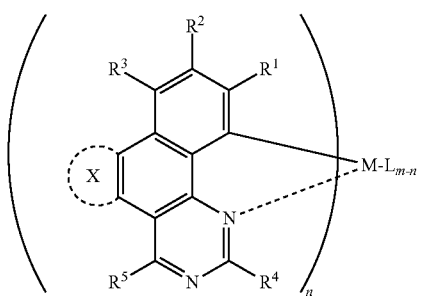

In General Formula (G2), M represents a metal belonging to Group 9 or 10 of the periodic table; L represents a monoanionic ligand; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen. When M represents a metal belonging to Group 9, m is 3 and n is 1, 2, or 3. When M represents a metal belonging to Group 10, m is 2 and n is 1 or 2.

In General Formula (G2), the monoanionic ligand is preferably a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two coordinating elements are both nitrogen. A monoanionic bidentate chelate ligand having a β-diketone structure is particularly preferable because the β-diketone structure allows the organometallic complex to have higher solubility in an organic solvent and to be easily purified. The β-diketone structure is preferably included for realization of an organometallic complex with high emission efficiency. Furthermore, the β-diketone structure brings advantages such as a higher sublimation property and excellent evaporativity.

In each the above-described structures, the monoanionic ligand is preferably represented by any of General Formulae (L1) to (L7). These ligands are useful because they have high coordinative ability and are available at low price.

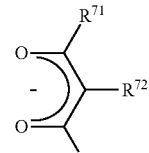

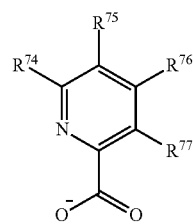

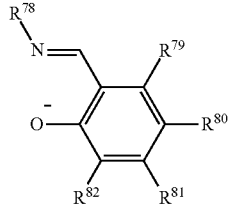

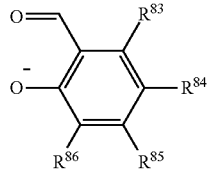

-continued

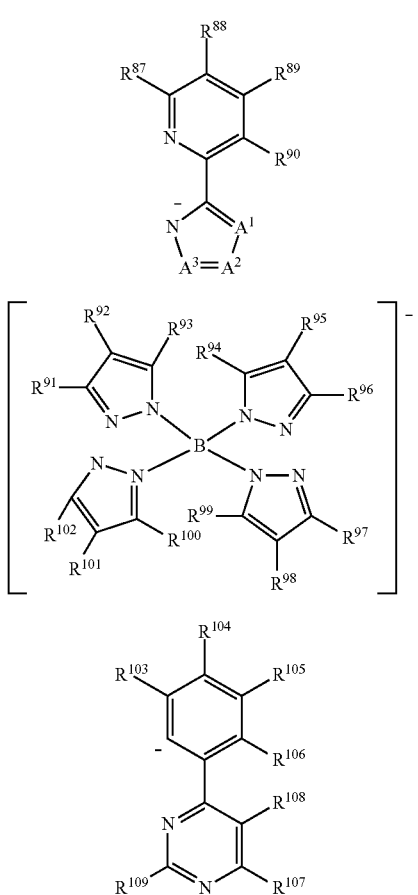

(L5)

(L6)

(L7)

In Formulae, each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. Each of $A^1$ to $A^3$ independently represents nitrogen, sp$^2$ hybridized carbon bonded to hydrogen, or sp$^2$ hybridized carbon having a substituent. The substituent is an alkyl group having 1 to 6 carbon atoms, a halogen group, a haloalkyl group having 1 to 6 carbon atoms, or a phenyl group.

Another embodiment of the present invention is an organometallic complex represented by General Formula (G3).

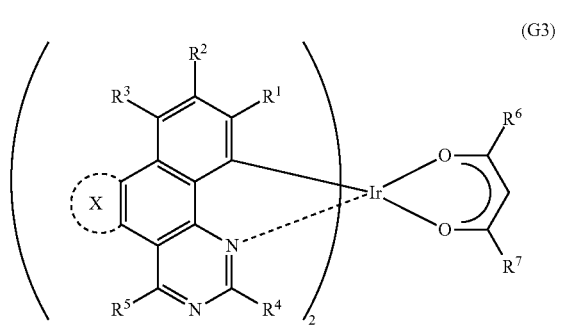

(G3)

In General Formula (G3), each of $R^1$ to $R^4$, $R^6$, and $R^7$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

Another embodiment of the present invention is an organometallic complex represented by General Formula (G4).

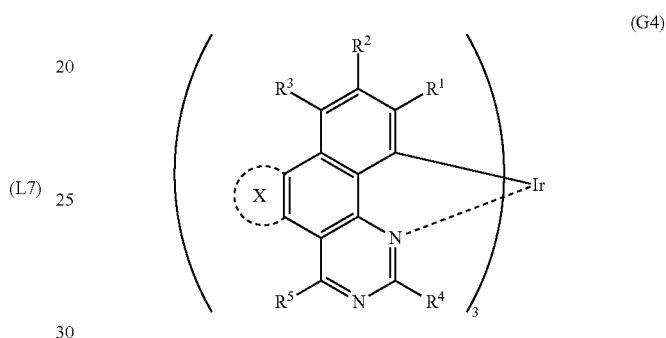

(G4)

In General Formula (G4), each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

Another embodiment of the present invention is an organometallic complex represented by Structural Formula (100).

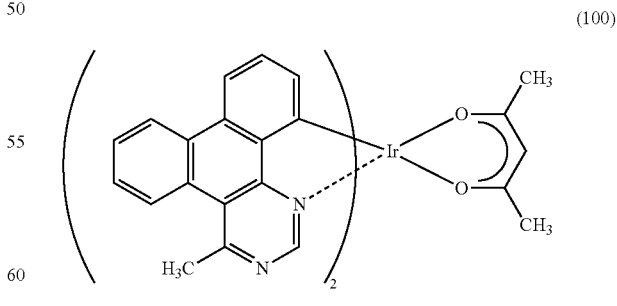

(100)

[Ir(mdbqz)$_2$(acac)]

Another embodiment of the present invention is an organometallic complex represented by Structural Formula (101).

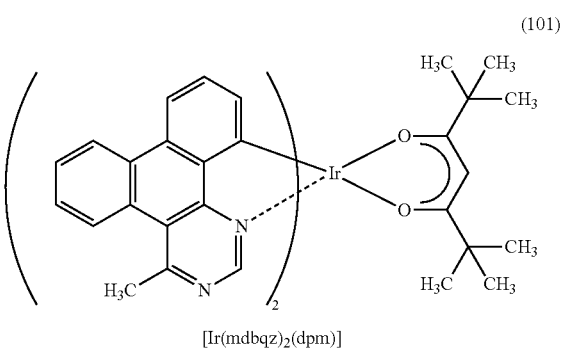

[Ir(mdbqz)₂(dpm)]

Another embodiment of the present invention is an organometallic complex represented by Structural Formula (104).

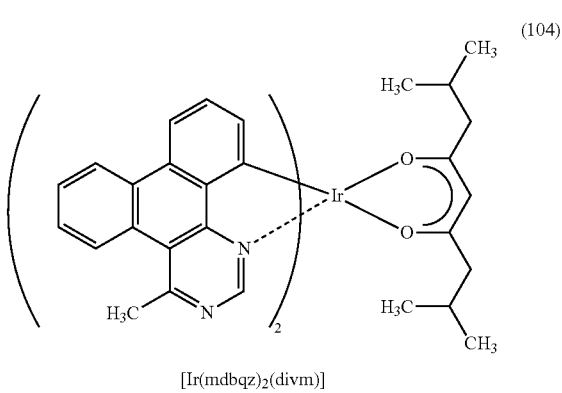

[Ir(mdbqz)₂(divm)]

Another embodiment of the present invention is an organometallic complex represented by Structural Formula (114).

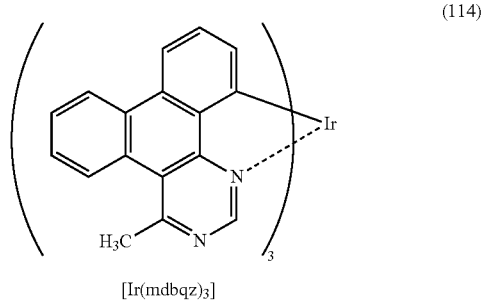

[Ir(mdbqz)₃]

The organometallic complex of one embodiment of the present invention has high heat resistance and high reliability, because the benzo[h]quinazoline skeleton that is a cyclometalated ligand includes a condensed ring structure that is bonded to benzo[h]quinazoline through a carbon-carbon bond of the 5- and the 6-position. In addition, since the organometallic complex of one embodiment of the present invention includes, as part of a ligand, the condensed ring structure that is bonded to benzo[h]quinazoline through a carbon-carbon bond of the 5- and the 6-position, extension of conjugation can be suppressed; thus, the emission wavelength can be shortened, and highly efficient blue green to yellow green light emission can be obtained.

Furthermore, the organometallic complex of one embodiment of the present invention is very effective for the following reason: the organometallic complex can emit phosphorescence, that is, it can provide light emission from the triplet excited state, and therefore, higher efficiency is possible when the organometallic complex is applied to a light-emitting element. Thus, one embodiment of the present invention also includes a light-emitting element in which the organometallic complex of one embodiment of the present invention is used.

In addition, one embodiment of the present invention includes, in its category, not only a light-emitting device including a light-emitting element but also a lighting device including a light-emitting device. Thus, a light-emitting device in this specification refers to an image display device or a light source (e.g., a lighting device). In addition, a light-emitting device includes, in its category, a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

With one embodiment of the present invention, it is possible to provide a novel organometallic complex capable of emitting phosphorescence; a novel organometallic complex with high emission efficiency; a novel organometallic complex with high heat resistance; a novel organometallic complex capable of emitting blue green to yellow green phosphorescence; or a light-emitting element, a light-emitting device, an electronic device, or a lighting device including the novel organometallic complex.

In addition, it is possible to provide a light-emitting element, a light-emitting device, an electronic device, or a lighting device with high emission efficiency, high reliability, or low power consumption. In addition, it is possible to provide a novel organometallic complex. In addition, it is possible to provide a novel light-emitting element, light-emitting device, electronic device, or lighting device.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 4A to 4D, 4D-1, and 4D-2 each illustrate an electronic device.

DETAILED DESCRIPTION OF THE INVENTION

Figure 1:
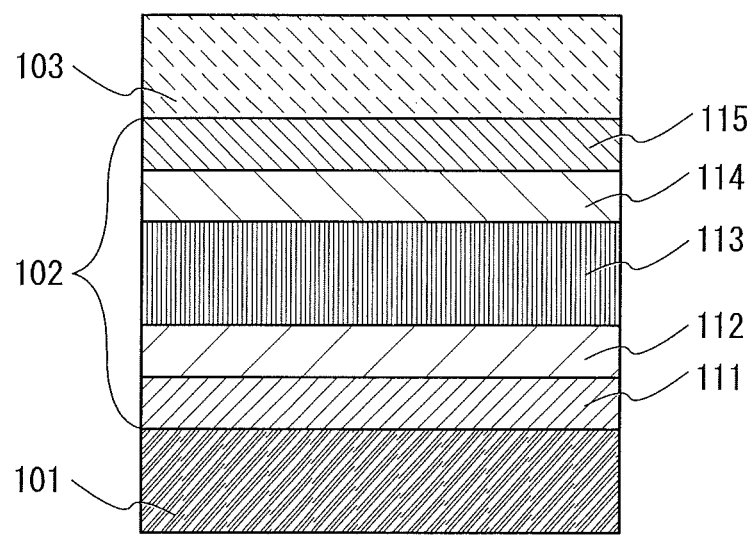
FIG. 1 illustrates the structure of a light-emitting element.

Embodiments of the present invention will be described in detail below with reference to the drawings. Note that the present invention is not limited to the following description, and modes and details thereof can be variously modified without departing from the spirit and the scope of the present invention. Accordingly, the present invention should not be interpreted as being limited to the content of the embodiments below.

Note that the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

Embodiment 1

In this embodiment, organometallic complexes which are embodiments of the present invention will be described.

An organometallic complex of one embodiment of the present invention includes a metal and a ligand. The ligand is a benzo[h]quinazoline skeleton. The benzo[h]quinazoline skeleton includes a condensed ring structure that is bonded to benzo[h]quinazoline through a carbon-carbon bond of the 5- and the 6-position. The benzo[h]quinazoline skeleton is bonded to the metal. One embodiment of the organometallic complex described in this embodiment includes a structure represented by General Formula (G1).

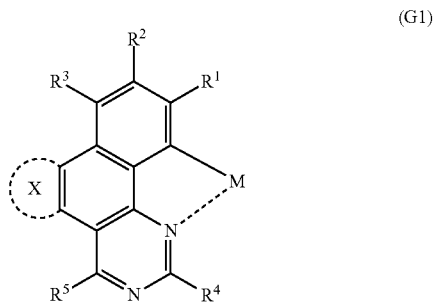

In General Formula (G1), M represents a metal belonging to Group 9 or 10 of the periodic table; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

One embodiment of the organometallic complex described in this embodiment is represented by General Formula (G2).

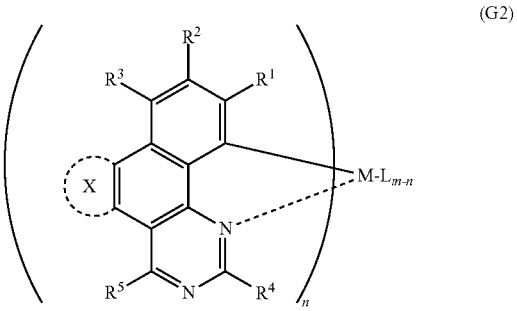

In General Formula (G2), M represents a metal belonging to Group 9 or 10 of the periodic table; L represents a monoanionic ligand; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen. When M represents a metal belonging to Group 9, in is 3 and n is 1, 2, or 3. When M represents a metal belonging to Group 10, in is 2 and n is 1 or 2.

The monoanionic ligand in General Formula (G2) is preferably a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two coordinating elements are both nitrogen. A monoanionic bidentate chelate ligand having a β-diketone structure is particularly preferable because the β-diketone structure allows the organometallic complex to have higher solubility in an organic solvent and to be easily purified.

Specifically, the monoanionic ligand is preferably represented by any of General Formulae (L1) to (L7).

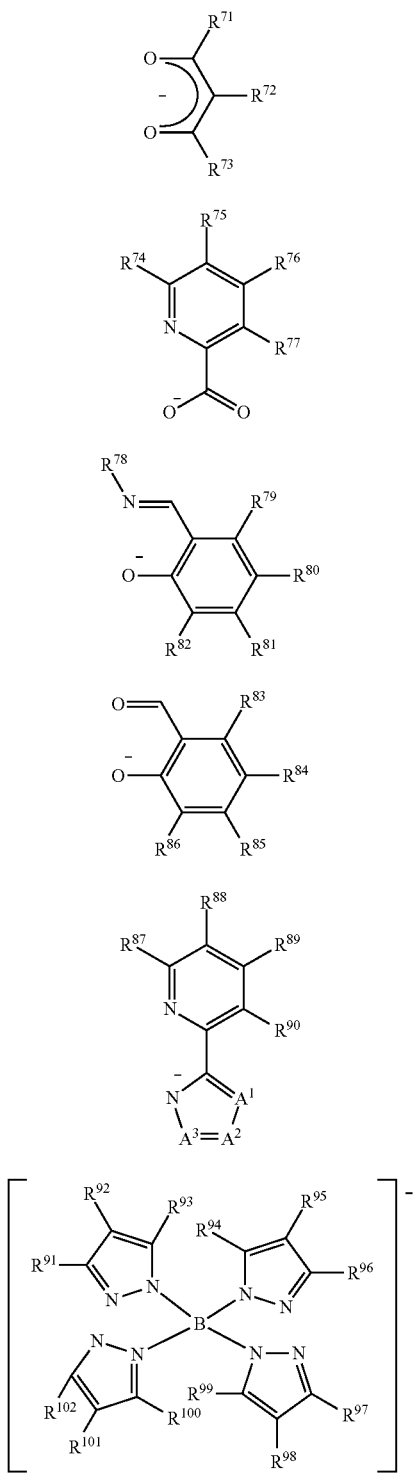

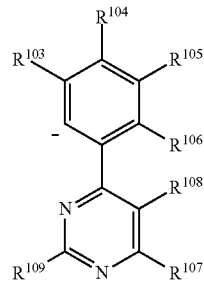

In Formulae, each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. Each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

In the organometallic complex of one embodiment of the present invention, the benzo[h]quinazoline skeleton includes a condensed ring structure. The benzo[h]quinazoline skeleton includes a condensed ring structure; thus, the heat resistance of the organometallic complex can be improved, leading to higher reliability of a light-emitting element including the organometallic complex. Since the organometallic complex includes the benzo[h]quinazoline skeleton, the emission efficiency can be improved. With the use of the organometallic complex of one embodiment of the present invention, a light-emitting material which emits blue green to yellow green light with high efficiency can be obtained.

Another embodiment of the present invention is an organometallic complex represented by General Formula (G4).

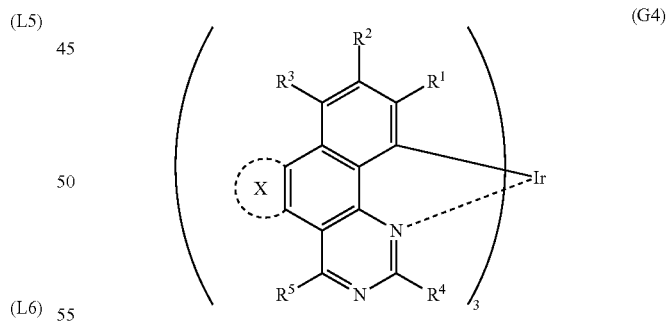

In General Formula (G4), each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

In General Formulae (G1), (G2), and (G4), specific examples of the alkyl group having 1 to 6 carbon atoms which is represented by any of R¹ to R⁵ include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Next, specific Structural Formulae of the above-described organometallic complexes which are embodiments of the present invention will be shown (Structural Formulae (100) to (119)). Note that the present invention is not limited thereto.

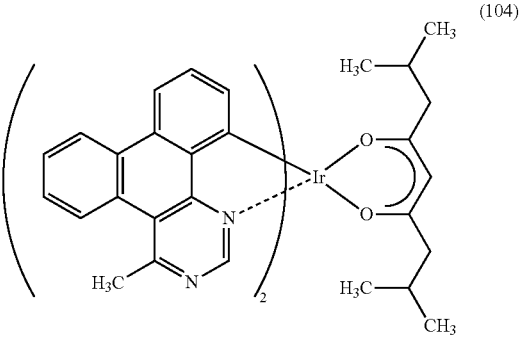

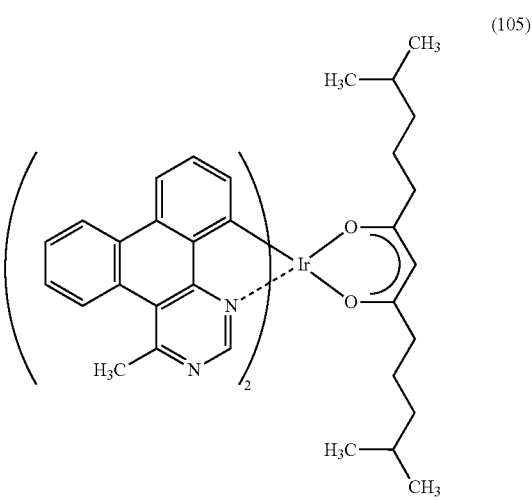

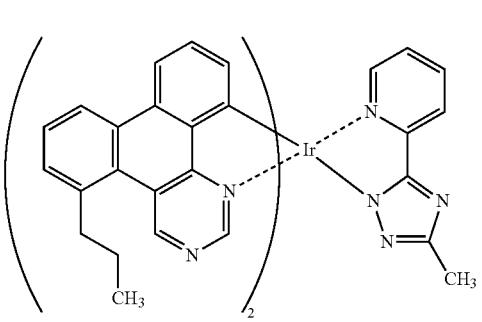

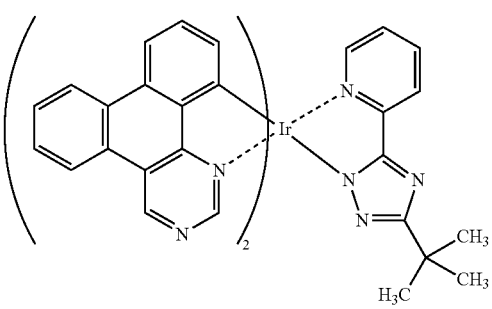

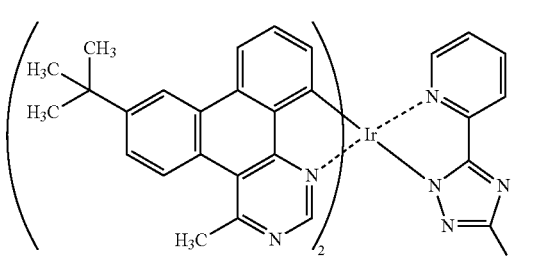
(108)
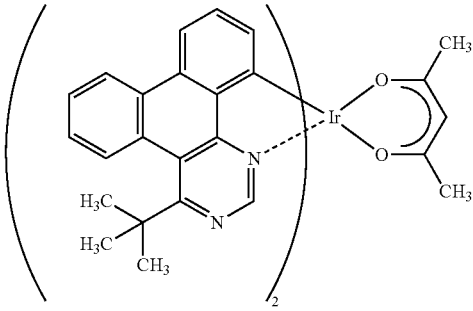
(113)
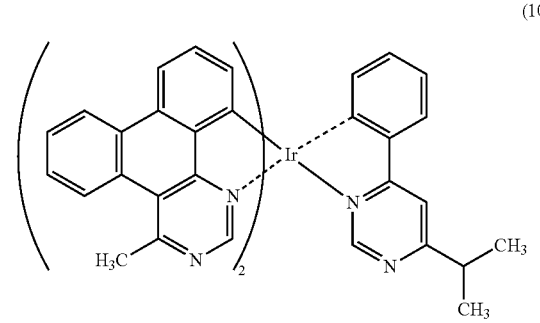
(109)
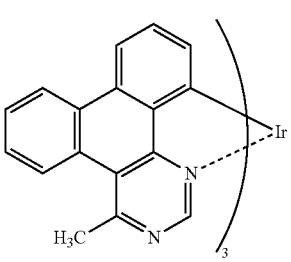
(114)
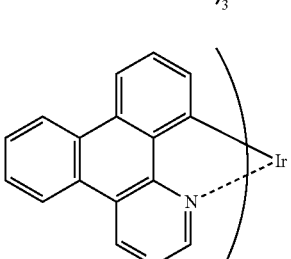
(115)
(110)
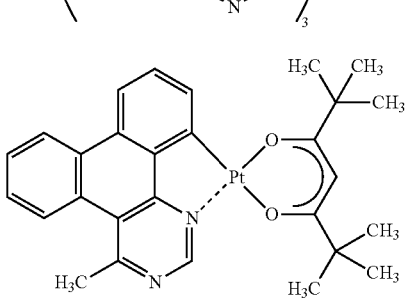
(116)
(111)
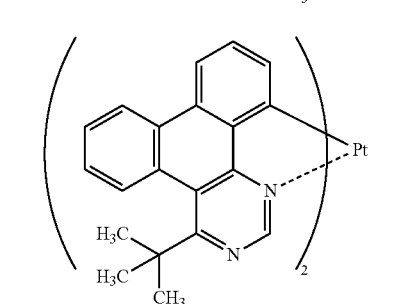
(117)
(112)
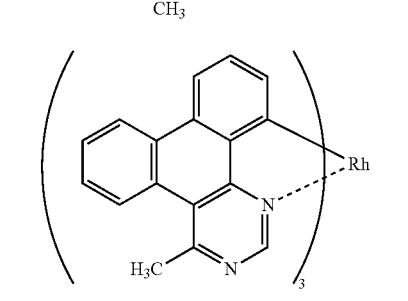
(118)

-continued

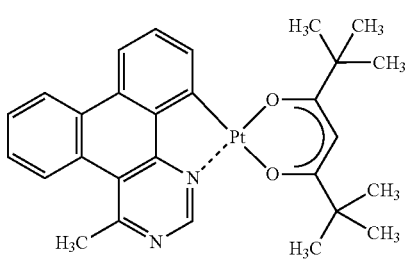
(119)

The organometallic complexes represented by Structural Formulae (100) to (119) are novel substances capable of emitting phosphorescence. Note that there can be geometrical isomers and stereoisomers of these substances depending on the type of the ligand. The organometallic complex of one embodiment of the present invention includes all of these isomers.

Next, an example of a method for synthesizing the organometallic complex of one embodiment of the present invention will be described.

<<Method for Synthesizing a Quinazoline Derivative Represented by General Formula (G0)>>

First, an example of a method for synthesizing a quinazoline derivative represented by General Formula (G0) is described.

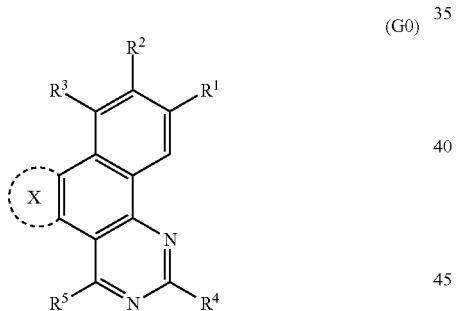
(G0)

In General Formula (G0), each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen.

The quinazoline derivative represented by General Formula (G0) can be synthesized by simple Synthesis Scheme (A) or (A') as shown below. As shown in Synthesis Scheme (A), the quinazoline derivative represented by General Formula (G0) can be synthesized by causing a reaction between a pyrimidine compound (A1) and an oxidizer, between the pyrimidine compound (A1) and acid, or between the pyrimidine compound (A1), an oxidizer, and acid.

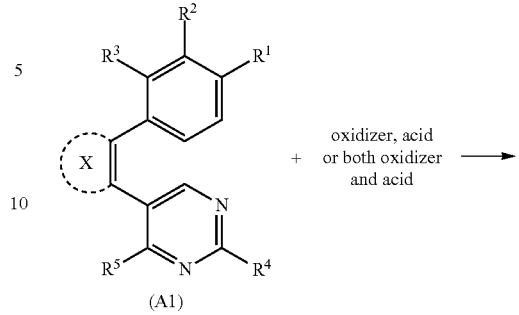
(A)
(A1)

Alternatively, as shown in Synthesis Scheme. (A'), the quinazoline derivative represented by General Formula (G0) can be synthesized by double coupling of a halogenated pyrimidine compound (A1') using a tin compound. In Synthesis Scheme (A'), Q represents halogen.

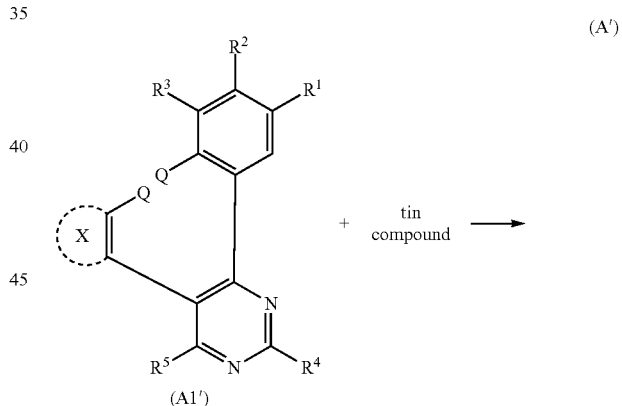
(A')
(A1')

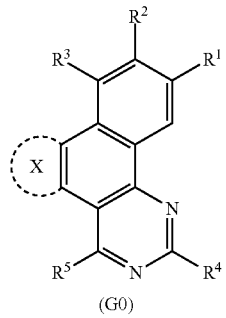
(G0)

Since various kinds of the above-described compounds (A1) and (A1') are commercially available or can be synthesized, many kinds of the quinazoline derivatives represented by General Formula (G0) can be synthesized.

Accordingly, the organometallic complex of one embodiment of the present invention has wide variations of ligands.

<<Method for Synthesizing the Organometallic Complex which is One Embodiment of the Present Invention and Represented by General Formula (G2)>>

Next, an example of a method for synthesizing the organometallic complex which is one embodiment of the present invention and represented by General Formula (G2) is described. As shown in Synthesis Scheme (B-1), the quinazoline derivative represented by General Formula (G0) and a halogen-containing metal compound (e.g., palladium chloride, iridium chloride, iridium bromide, iridium iodide, or potassium tetrachloroplatinate) are heated in an inert gas atmosphere, so that a dinuclear complex (P), which is one type of an organometallic complex including a halogen-bridged structure and is a novel substance, can be obtained. In the above reaction, an alcohol-based solvent (e.g., glycerol, ethylene glycol, 2-methoxyethanol, or 2-ethoxyethanol) or a mixed solvent of water and one or more of the alcohol-based solvents may be used. There is no particular limitation on a heating means, and an oil bath, a sand bath, or an aluminum block may be used. Alternatively, microwaves can be used as a heating means. In Synthesis Scheme (B-1), M represents a metal belonging to Group 9 or 10 of the periodic table. When M represents a metal belonging to Group 9, n is 2. When M represents a metal belonging to Group 10, n is 1.

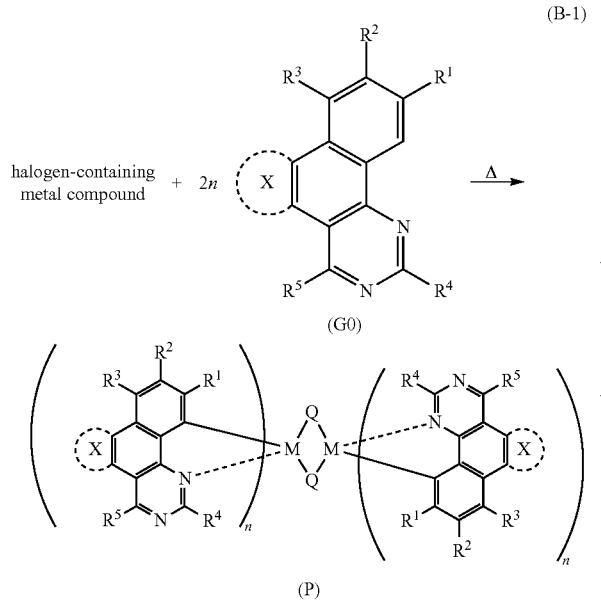

(B-1)

(G0)

(P)

In Synthesis Scheme (B-1), Q represents halogen; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen. When M represents a metal belonging to Group 9, n is 2. When M represents a metal belonging to Group 10, n is 1.

Then, as shown in Synthesis Scheme (B-2), the dinuclear complex (P) obtained in Synthesis Scheme (B-1) and HL which is a material of a monoanionic ligand are heated in an inert gas atmosphere, so that a proton of HL is separated and L coordinates to the central metal M. Thus, the organometallic complex which is one embodiment of the present invention and represented by General Formula (G2) can be obtained. There is no particular limitation on a heating means, and an oil bath, a sand bath, or an aluminum block may be used. Alternatively, microwaves can be used as a heating means. In Synthesis Scheme (B-2), M represents a metal belonging to Group 9 or 10 of the periodic table. When M represents a metal belonging to Group 9, m is 3 and n is 2. When M represents a metal belonging to Group 10, m is 2 and n is 1.

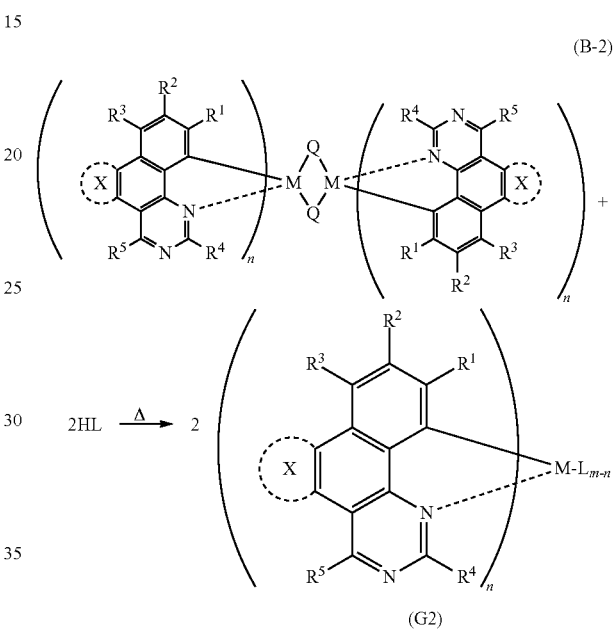

(B-2)

(G2)

In Synthesis Scheme (B-2), L represents a monoanionic ligand; Q represents halogen; each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen. When M represents a metal belonging to Group 9, m is 3 and n is 2. When M represents a metal belonging to Group 10, m is 2 and n is 1.

In one embodiment of the present invention, a substituent is preferably bonded to $R^5$ in order that an ortho-metalated complex containing, as a ligand, the quinazoline derivative represented by General Formula (G0) can be obtained. In particular, a substituted or unsubstituted alkyl group having 1 to 6 carbon atoms or a substituted or unsubstituted phenyl group is preferably used as $R^5$. In that case, decomposition of the halogen-bridged dinuclear metal complex, which is synthesized in Synthesis Scheme (B-1), during the reaction represented by Synthesis Scheme (B-2) is more suppressed than in the case where hydrogen is used as $R^5$, leading to a drastically high yield. This also increases the resolvability of the ortho-metalated complex and facilitates purification using a solution, which can increase the purity of a material. Therefore, when the ortho-metalated complex is used as a dopant of a light-emitting element, the light-emitting element has stable characteristics and high reliability. Furthermore, when the ortho-metalated complex is used as a dopant of a light-emitting element, the dispersibility of the dopant can be improved and quenching can be prevented, increasing the emission efficiency.

The monoanionic ligand L in General Formula (G2) is preferably a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two coordinating elements are both nitrogen. A monoanionic bidentate chelate ligand having a β-diketone structure is particularly preferable because the β-diketone structure allows the organometallic complex to have higher solubility in an organic solvent and to be easily purified. The β-diketone structure is preferably included for realization of an organometallic complex with high emission efficiency. Furthermore, the β-diketone structure brings advantages such as a higher sublimation property and excellent evaporativity.

The monoanionic ligand is preferably represented by any of General Formulae (L1) to (L7). These ligands are useful because they have high coordinative ability and are available at low price.

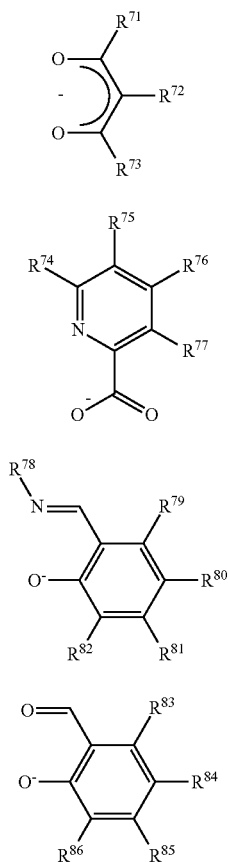

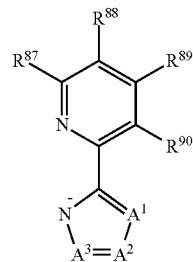

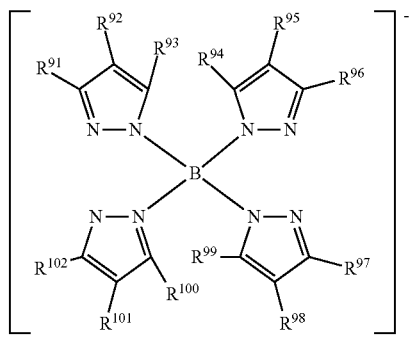

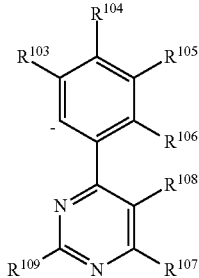

In Formulae, each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. Each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

<<Method for Synthesizing an Organometallic Complex which is One Embodiment of the Invention and Represented by General Formula (G2')>>

An example of a method for synthesizing an organometallic complex which is one embodiment of the present invention and represented by General Formula (G2') is described. As shown in Synthesis Scheme (C), the quinazoline derivative represented by General Formula (G0) is mixed with a halogen-containing compound of a metal belonging to Group 9 or 10 of the periodic table (e.g., rhodium chloride hydrate, palladium chloride, iridium chloride hydrate, ammonium hexachloroiridate, or potassium tetrachloroplatinate) or an organometallic complex compound of a metal belonging to Group 9 or 10 (e.g., an acetylacetonate complex or a diethylsulfide complex), and then, the mixture is heated, so that an organometallic complex including a structure represented by General Formula (G2') can be obtained. This heating process may be performed after the quinazoline derivative represented by General Formula (G0) and the halogen-containing compound of a metal belonging to Group 9 or 10 or the organometallic complex compound of a metal belonging to Group 9 or 10 are dissolved in an alcohol-based solvent (e.g., glycerol, ethylene glycol, 2-methoxyethanol, or 2-ethoxyethanol). In Synthesis Scheme (C), M represents a metal belonging to Group 9 or 10. When M represents a metal belonging to Group 9, n is 3. When M represents a metal belonging to Group 10, n is 2.

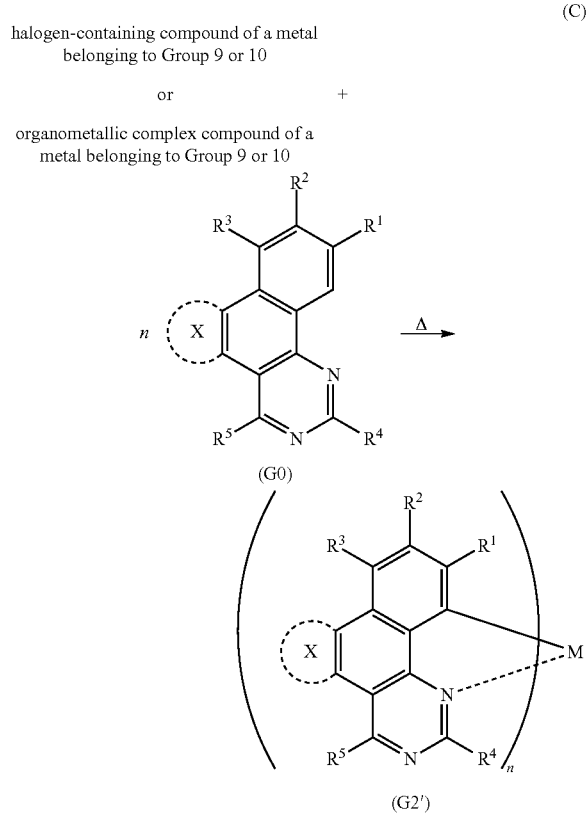

(C)

In Synthesis Scheme (C), each of $R^1$ to $R^4$ independently represents hydrogen, a substituted or unsubstituted alkyl group having 1 to 6 carbon atoms, or a substituted or unsubstituted aryl group having 6 to 10 carbon atoms; and $R^5$ represents hydrogen, a substituted or unsubstituted alkyl group having 1 to 6 carbon atoms, or a substituted or unsubstituted phenyl group. A ring X represents a substituted or unsubstituted six-membered aromatic ring formed with carbon or both carbon and nitrogen. When M represents a metal belonging to Group 9, n is 3. When M represents a metal belonging to Group 10, n is 2.

In one embodiment of the present invention, a substituent is preferably bonded to $R^5$ in order that an ortho-metalated complex containing, as a ligand, the quinazoline derivative represented by General Formula (G0) can be obtained. In particular, a substituted or unsubstituted alkyl group having 1 to 6 carbon atoms or a substituted or unsubstituted phenyl group is preferably used as $R^5$. In that case, as compared to the case where hydrogen is used as $R^5$, the yield in Synthesis Scheme (C) can be higher.

The above is the description of examples of a method for synthesizing the organometallic complex of one embodiment of the present invention; however, the present invention is not limited thereto, and any other synthesis methods may be employed.

The above-described organometallic complex of one embodiment of the present invention can emit phosphorescence and can be used as a light-emitting material or a light-emitting substance of a light-emitting element.

Embodiment 2

In this embodiment, it will be described, how the emission wavelength can be shortened due to a molecular structure in the organometallic complex of one embodiment of the present invention.

Although fusion of a benzene ring can improve the heat resistance of a cyclometalated ligand, conjugation is extended due to the fusion in many cases, which makes the emission wavelength longer. However, when the ligand is a benzo[h]quinazoline skeleton, depending on the position where the benzene ring is fused, extension of conjugation is suppressed, leading to a shorter emission wavelength; in other words, the heat resistance can be improved and the emission wavelength can be shortened. Molecular orbital calculations were performed as described below. The results indicate that the broadening of the spin density distribution is suppressed. Therefore, the $T_1$ level is higher, leading to a shorter emission wavelength.

Molecular orbital distribution obtained by the calculations is described. For the calculations, the organometallic complex represented by Structural Formula (500), bis(dibenzo[f,h]quinazolin-12-yl-κC,κN)(2,4-pentanedionato-κ²O,O')iridium(III) (Abbreviation: [Ir(dbqz)₂(acac)]), was used.

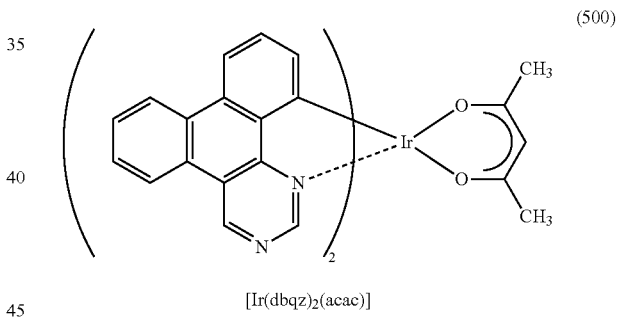

[Ir(dbqz)₂(acac)]

For comparison, the organometallic complex represented by Structural Formula (600), bis(benzo[h]quinazolin-10-yl-κC,κN)(2,4-pentanedionato-κ²O,O')iridium(III) (Abbreviation: [Ir(bqn)₂(acac)]), was used. Note that [Ir(bqn)₂(acac)] emits yellow light.

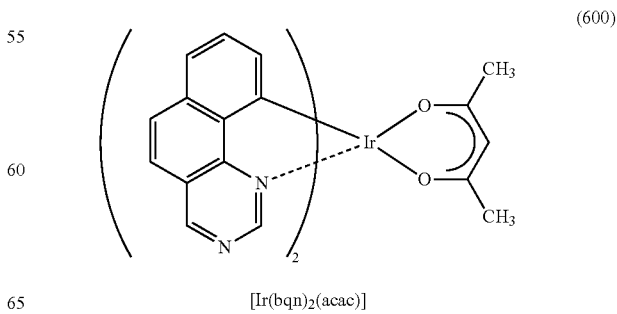

[Ir(bqn)₂(acac)]

Calculation Example

The most stable structures of [Ir(dbqz)$_2$(acac)], which is the organometallic complex of one embodiment of the present invention, in the singlet ground state (S$_0$) and the lowest excited triplet state (T$_1$) and the most stable structures of [Ir(bqn)$_2$(acac)], which is a comparative example, in the singlet ground state (S$_0$) and the lowest excited triplet state (T$_1$) were calculated using the density functional theory (DFT). Then, vibration analysis was conducted on the most stable structures, and the T$_1$ level was calculated from a difference between the total energy in the singlet ground state (S$_0$) and the total energy in the lowest excited triplet state (T$_1$). In the DFT, the total energy is represented as the sum of potential energy, electrostatic energy between electrons, electronic kinetic energy, and exchange-correlation energy including all the complicated interactions between electrons. In the DFT, an exchange-correlation interaction is approximated by a functional (a function of a function) of one electron potential represented in terms of electron density to enable high-speed calculations. Here, B3PW91, which is a hybrid functional, was used to specify the weight of each parameter related to exchange-correlation energy.

In addition, as basis functions, 6-311G (a basis function of a triple-split valence basis set using three contraction functions for a valence orbital) was applied to each of H, C, N, and O atoms, and Lan L2DZ was applied to an Ir atom. By the above basis functions, for example, 1s to 3s orbitals are considered in the case of hydrogen atoms, while is to 4s and 2p to 4p orbitals are considered in the case of carbon atoms. Furthermore, to improve calculation accuracy, the p function and the d function as polarization basis sets were added respectively to hydrogen atoms and atoms other than hydrogen atoms. Note that calculations were performed with a polarizable continuum model in consideration of the solvent effects, that is, the dielectric constant ($\varepsilon$=8.93) corresponding to that of a dichloromethane solvent. Gaussian 09 was used as a quantum chemistry computational program. A high performance computer (Altix 4700, manufactured by SGI Japan, Ltd.) was used for the calculations.

Figure 13A:
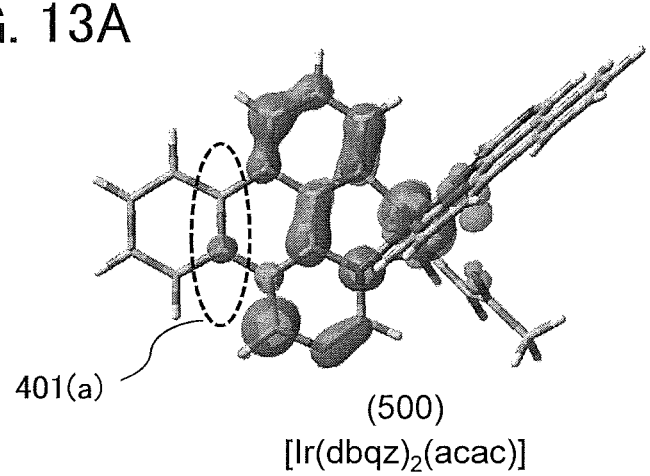
FIGS. 13A and 13B show the spin density distribution of an organometallic complex represented by Structural Formula (500) and that of an organometallic complex represented by Structural Formula (600), respectively.
Figure 13B:
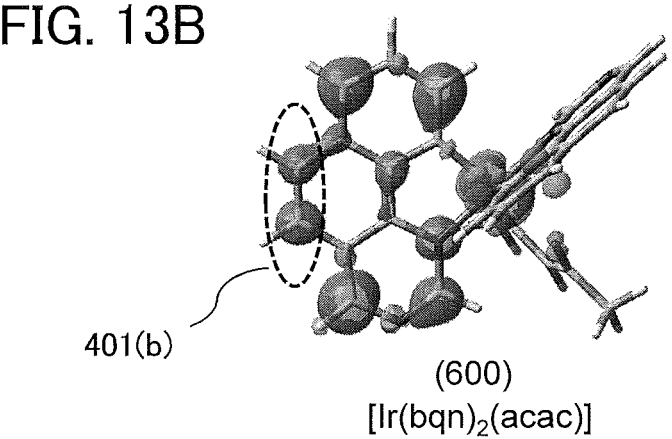

The structure optimization was performed on the singlet ground state (S$_0$) and the lowest excited triplet state (T$_1$) of the organometallic complex [Ir(dbqz)$_2$(acac)] represented by Structural Formula (500) and those of the organometallic complex [Ir(bqn)$_2$(acac)] represented by Structural Formula (600), and the T$_1$ level and the spin density distribution were calculated. FIGS. 13A and 13B show the spin density distribution.

The calculated T$_1$ level of [Ir(dbqz)$_2$(acac)] was 2.22 eV, whereas that of [Ir(bqn)$_2$(acac)] was 2.13 eV. This indicates that the emission wavelength of [Ir(dbqz)$_2$(acac)] is shorter than that of [Ir(bqn)$_2$(acac)].

As shown in FIGS. 13A and 13B, in a region 401(a) of [Ir(dbqz)$_2$(acac)], the spin density distribution is not strong and the broadening of the spin density distribution is suppressed compared to a region 401(b) of [Ir(bqn)$_2$(acac)]. This is caused by a difference in C—C bond length.

Figure 14A:
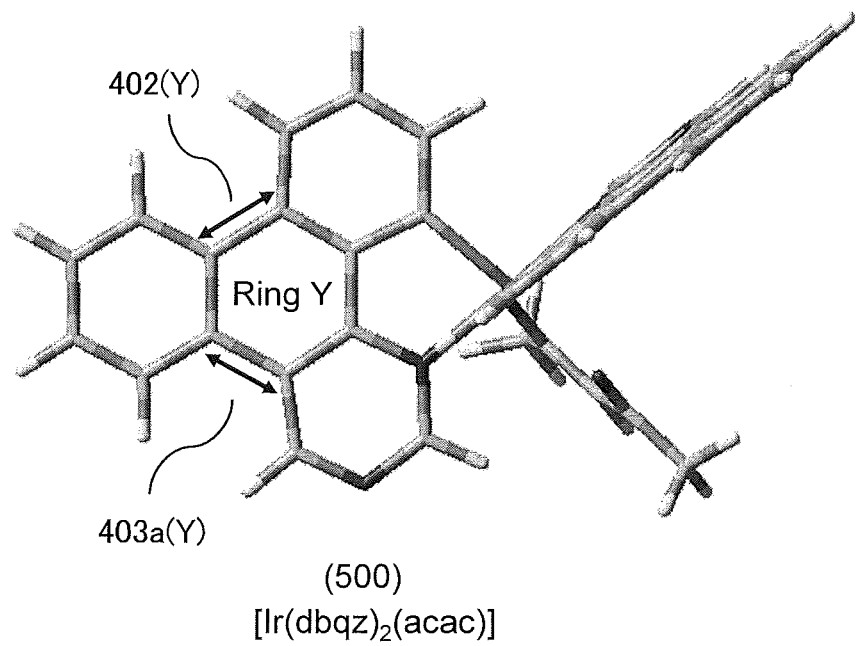
FIGS. 14A and 14B show the positions of C—C bonds in the organometallic complex represented by Structural Formula (500) and those in the organometallic complex represented by Structural Formula (600), respectively.
Figure 14B:
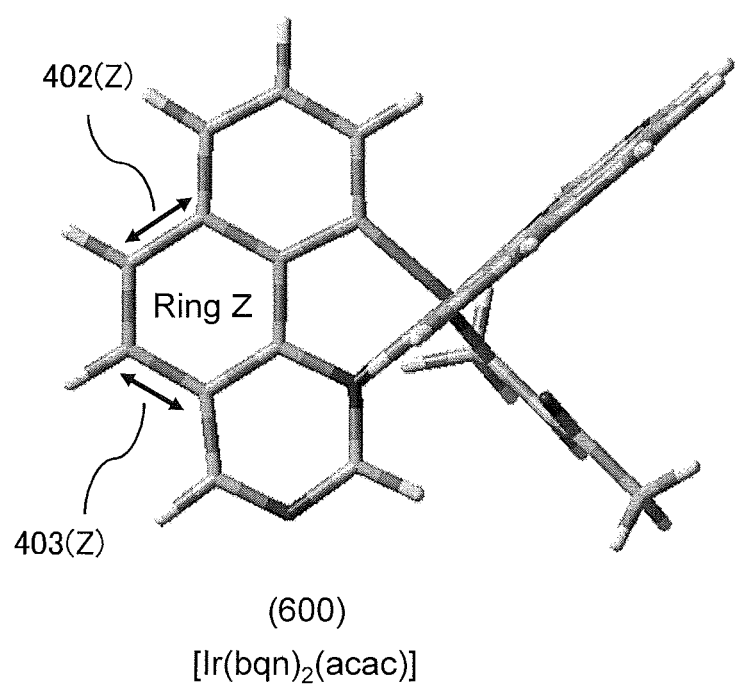

FIG. 14A shows the positions of a C—C bond 402(Y) and a C—C bond 403(Y) in a benzene ring Y of [Ir(dbqz)$_2$(acac)], and FIG. 14B shows the positions of a C—C bond 402(Z) and a C—C bond 403(Z) in a benzene ring Z of [Ir(bqn)$_2$(acac)]. In the benzene ring Y of [Ir(dbqz)$_2$(acac)], the C—C bond distance of the C—C bond 402(Y) is 0.1465 nm, and the C—C bond distance of the C—C bond 403(Y) is 0.1457 nm. In the benzene ring Z of [Ir(bqn)$_2$(acac)], the C—C bond distance of the C—C bond 402(Z) is 0.1438 nm, and the C—C bond distance of the C—C bond 403(Z) is 0.1432 nm. As compared to the C—C bond 402(Z) and the C—C bond 403(Z), the C—C bond 402(Y) and the C—C bond 403(Y) each have a longer C—C bond distance. The following is considered to be a factor of the above difference: in consideration of the resonance structure, the possibility of the C—C bond 402(Y) and the C—C bond 403(Y) becoming a single bond, not a double bond, is higher than that of the C—C bond 402(Z) and the C—C bond 403(Z). With a high possibility of the C—C bond 402(Y) and the C—C bond 403(Y) becoming a single bond, the C—C bond 402(Y) and the C—C bond 403(Y) each have a longer C—C bond distance than the C—C bond 402(Z) and the C—C bond 403(Z); therefore, in [Ir(dbqz)$_2$(acac)], extension of conjugation is suppressed, which suppresses the broadening of the spin density distribution. Accordingly, the T$_1$ level of [Ir(dbqz)$_2$(acac)] is higher, leading to a shorter emission wavelength.

Table 1 shows calculated proportions of the spin density distribution at a central metal and ligands in [Ir(dbqz)$_2$(acac)] and [Ir(bqn)$_2$(acac)].

TABLE 1

|  | [Ir(dbqz)$_2$(acac)] | [Ir(bqn)$_2$(acac)] |
|---|---|---|
| Ir | 25.0% | 19.9% |
| Cyclometalated Ligand_1 | 66.7% | 73.5% |
| Cyclometalated Ligand_2 | 5.4% | 3.7% |
| Monoanionic Ligand | 2.9% | 2.8% |

According to Table 1, the proportion of the spin density distribution at a central metal Ir is 25.0% in [Ir(dbqz)$_2$(acac)], and the proportion of the spin density distribution at a central metal Ir is 19.9% in [Ir(bqn)$_2$(acac)]; thus, the proportion of the spin density distribution at Ir in [Ir(dbqz)$_2$(acac)] is higher than that in [Ir(bqn)$_2$(acac)]. Since the proportion of the spin density distribution at Ir that is a central metal is high, metal-to-ligand charge transfer (MLCT transfer) that is charge transfer to a ligand is considered to occur with a high frequency in [Ir(dbqz)$_2$(acac)]. It is known that the emission mechanism of a phosphorescent transition metal complex with high efficiency is generally MLCT transfer; thus, the calculation results show that the emission efficiency of [Ir(dbqz)$_2$(acac)] is high.

According to the above, in [Ir(dbqz)$_2$(acac)] that is obtained by fusing a benzene ring to a cyclometalated ligand of [Ir(bqn)$_2$(acac)], the broadening of the spin density distribution can be suppressed, leading to a higher T$_1$ level. Accordingly, [Ir(dbqz)$_2$(acac)] is an organometallic complex with high heat resistance and high emission efficiency, which emits blue green to yellow green light whose wavelength is shorter than that of yellow light emitted from [Ir(bqn)$_2$(acac)].

Embodiment 3

In this embodiment, a light-emitting element in which the organometallic complex described in Embodiment 1 is used for a light-emitting layer will be described as one embodiment of the present invention with reference to FIG. 1.

FIG. 1 illustrates a light-emitting element including an EL layer 102 between a first electrode 101 and a second electrode 103. The EL layer 102 includes a light-emitting layer 113, and the light-emitting layer 113 contains the organometallic complex described in Embodiment 1. The EL layer 102 includes, in addition to the light-emitting layer 113, a hole-injection layer 111, a hole-transport layer 112, an electron-transport layer 114, and an electron-injection layer 115.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. In this manner, the organometallic complex of one embodiment of the present invention functions as a light-emitting substance in the light-emitting element. Note that in the light-emitting element described in this embodiment, the first electrode 101 and the second electrode 103 function as an anode and a cathode, respectively.

The hole-injection layer 111 included in the EL layer 102 is a layer containing a substance having a high hole-transport property and an acceptor substance. When electrons are extracted from the substance having a high hole-transport property with the acceptor substance, holes are generated. Thus, holes are injected from the hole-injection layer 111 into the light-emitting layer 113 through the hole-transport layer 112.

A specific example in which the light-emitting element described in this embodiment is fabricated will be described below.

For the first electrode 101 functioning as an anode, any of metals, alloys, electrically conductive compounds, mixtures thereof, and the like which has a high work function (specifically, a work function of 4.0 eV or higher) is preferably used. Specific examples include indium oxide-tin oxide (indium tin oxide, ITO), indium oxide-tin oxide containing silicon or silicon oxide, indium oxide-zinc oxide (indium zinc oxide, IZO), and indium oxide containing tungsten oxide and zinc oxide. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), silver (Ag), aluminum (Al), or the like can be used. When a layer included in the EL layer 102 which is formed in contact with the first electrode 101 is formed using a composite material in which an organic compound and an electron acceptor (acceptor) which are described later are mixed, as a substance for the first electrode 101, any of a variety of metals, alloys, electrically conductive compounds, mixtures thereof, and the like can be used regardless of the work function.

The first electrode 101 can be formed by, for example, a sputtering method, an evaporation method (including a vacuum evaporation method), or the like. In the case of using a silver paste or the like, a coating method, an ink-jet method, or the like can be used.

The EL layer 102 formed over the first electrode 101 includes at least the light-emitting layer 113 and contains the organometallic complex described in Embodiment 1. For part of the EL layer 102, any of a variety of substances can be used, and either a low molecular compound or a high molecular compound can be used. Note that substances for forming the EL layer 102 may consist of organic compounds or may include an inorganic compound as a part.

Examples of the substance having a high hole-transport property, which is used for the hole-injection layer 111 and the hole-transport layer 112, include aromatic amine compounds such as 4,4'-bis[N-(1-naphthyl)-N-phenylamino]biphenyl (abbreviation: NPB or α-NPD), N,N-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). In addition, the following carbazole derivatives can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances described here are mainly substances having a hole mobility of $10^{-6}$ $cm^2/Vs$ or higher. However, other substances may also be used as long as their hole-transport properties are higher than their electron-transport properties.

Furthermore, a high molecular compound such as poly (N-vinylcarbazole) (abbreviation: PVK), poly(4-vinyltriphenylamine) (abbreviation: PVTPA), poly[N-(4-{N'-[4-(4-diphenylamino)phenyl]phenyl-M-phenylamino}phenyl) methacrylamide] (abbreviation: PTPDMA), or poly[N,N'-bis(4-butylphenyl)-N,N'-bis(phenyl)benzidine] (abbreviation: Poly-TPD) can be used.

Examples of the acceptor substance that is used for the hole-injection layer 111 include oxides of metals belonging to Groups 4 to 8 of the periodic table. Specifically, molybdenum oxide is particularly preferable.

The light-emitting layer 113 is a layer containing a light-emitting substance. Note that the organometallic complex described in Embodiment 1 can be used as the light-emitting substance, and the light-emitting layer 113 may contain, as a host material, a substance having higher triplet excitation energy than the organometallic complex (guest material). Alternatively, the light-emitting layer 113 may contain, in addition to the light-emitting substance, two kinds of organic compounds that can form an excited complex (also called an exciplex) at the time of recombination of carriers (electrons and holes) in the light-emitting layer (the two kinds of organic compounds may be any of host materials as described above).

Examples of an organic compound that can be used as the host material and the two kinds of organic compounds that can form an exciplex include compounds having an arylamine skeleton, such as 2,3-bis(4-diphenylaminophenyl)quinoxaline (abbreviation: TPAQn) and NPB; carbazole derivatives such as CBP and 4,4',4"-tris(carbazol-9-yl)triphenylamine (abbreviation: TCTA); and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris (8-quinolinolato)aluminum (abbreviation: Alq$_3$). In addition, a high molecular compound such as PVK can be used.

In the case where the light-emitting layer 113 contains the organometallic complex (guest material) and the host material or the two kinds of organic compounds that can form an exciplex, phosphorescence can be emitted from the light-emitting layer 113 with high efficiency.

Alternatively, the light-emitting layer 113 may contain, in addition to the organometallic complex of one embodiment of the present invention, a light-emitting substance converting singlet excitation energy into light emission or a light-emitting substance converting triplet excitation energy into light emission. In that case, the light-emitting substance may be contained in the same layer as or in a different layer from the organometallic complex. When these light-emitting substances emit light of different colors, the light-emitting element can emit light of a desired color as a whole. For example, a light-emitting element including three light-emitting layers can emit white light as a whole, when the emission color of a first light-emitting layer is red, the emission color of a second light-emitting layer is green, and the emission color of a third light-emitting layer is blue. Described below are examples of the light-emitting substance.

As an example of the light-emitting substance converting singlet excitation energy into light emission, a substance which emits fluorescence (a fluorescent compound) can be given.

Examples of the substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into light emission include a substance which emits phosphorescence (a phosphorescent compound) and a thermally activated delayed fluorescent (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance which emits phosphorescence include bis{2-[3',5'-bis(trifluoromethyl)phenyl]pyridinato-N,$C^{2'}$}iridium(III) picolinate (Abbreviation: [Ir(CF$_3$ppy)$_2$(pic)]), bis[2-(4',6'-difluorophenyl)pyridinato-N,$C^{2'}$]iridium(III) acetylacetonate (abbreviation: FIracac), tris(2-phenylpyridinato)iridium(III) (Abbreviation: [Ir(ppy)$_3$]), bis(2-phenylpyridinato)iridium(III) acetylacetonate (Abbreviation: [Ir(ppy)$_2$(acac)]), tris(acetylacetonato)(monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N, acetylacetonate (Abbreviation: [Ir(dpo)$_2$(acac)]), bis{2-[4'-(perfluorophenyl)phenyl]pyridinato-N,$C^{2'}$}iridium(III) acetylacetonate (Abbreviation: [Ir(p-PF-ph)$_2$(acac)]), bis(2-phenylbenzothiazolato-N,$C^{2'}$)iridium(III) acetylacetonate (Abbreviation: [Ir(bt)$_2$(acac)]), bis[2-(2'-benzo[4,5-a]thienyl)pyridinato-N,$C^{3'}$]iridium(III) acetylacetonate (Abbreviation: [Ir(btp)$_2$(acac)]), bis(1-phenylisoquinolinato-N,$C^{2'}$)iridium(III) acetylacetonate (Abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (Abbreviation: [Ir(mppr-Me)$_2$(acac)]), (acetylacetonato)bis(5-isopropyl-3-methyl-2-phenylpyrazinato)iridium(III) (Abbreviation: [Ir(mppr-iPr)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (Abbreviation: [Ir(tppr)$_2$(dpm)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (Abbreviation: [Ir(dppm)$_2$(acac)]), 2,3,7,8,12,13,17,18-octaethyl-21H,23H-porphyrin platinum(II) (abbreviation: PtOEP), tris(1,3-diphenyl-1,3-propanedionato) (monophenanthroline)europium(II) (abbreviation: [Eu(DBM)$_3$(Phen)]), and tris[1-(2-thenoyl)-3,3,3-trifluoroacetonato](monophenanthroline)europium(III) (abbreviation: [Eu(TTA)$_3$(Phen)]).

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). In addition, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a substance in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the $S_1$ level and the $T_1$ level becomes small.

The electron-transport layer 114 is a layer containing a substance having a high electron-transport property (also referred to as an electron-transport compound). For the electron-transport layer 114, a metal complex such as tris (8-quinolinolato)aluminum (abbreviation: $Alq_3$), tris(4-methyl-8-quinolinolato)aluminum (abbreviation: $Almq_3$), bis(10-hydroxybenzo[h]quinolinato)beryllium (abbreviation: $BeBq_2$), bis(2-methyl-8-quinolinolato)(4-phenylphenolato)aluminum (abbreviation: BAlq), bis[2-(2-hydroxyphenyl)benzoxazolato]zinc (abbreviation: $Zn(BOX)_2$), or bis[2-(2-hydroxyphenyl)benzothiazolato]zinc (abbreviation: $Zn(BTZ)_2$) can be used. Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl] benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances described here are mainly substances having an electron mobility of $10^{-6}$ $cm^2/Vs$ or higher. However, other substances may also be used for the electron-transport layer 114 as long as their electron-transport properties are higher than their hole-transport properties.

The electron-transport layer 114 is not limited to a single layer and may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide ($LiO_x$) can be used. Alternatively, a rare earth metal compound such as erbium fluoride ($ErF_3$) can be used. An electride may also be used for the electron-injection layer 115. Examples of the electride include a substance in which electrons are added at high concentration to calcium oxide-aluminum oxide. Any of the substances for forming the electron-transport layer 114, which are given above, can also be used.

Alternatively, the electron-injection layer 115 may be formed using a composite material in which an organic compound and an electron donor (donor) are mixed. The composite material is superior in an electron-injection property and an electron-transport property, since electrons are generated in the organic compound with the electron donor. In that case, the organic compound is preferably a material which is excellent in transporting the generated electrons. Specifically, the above-described substances for forming the electron-transport layer 114 (e.g., a metal complex or a heteroaromatic compound) can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, or the like can be used. Furthermore, an alkali metal oxide or an alkaline earth metal oxide is preferable, and for example, lithium oxide, calcium oxide, barium oxide, or the like can be used. Alternatively, Lewis base such as magnesium oxide can be used. An organic compound such as tetrathiafulvalene (abbreviation: TTF) can also be used.

The hole-injection layer 111, the hole-transport layer 112, the light-emitting layer 113, the electron-transport layer 114, and the electron-injection layer 115, which are described above, can each be formed by any of the following methods: an evaporation method (including a vacuum evaporation method), a printing method (such as relief printing, intaglio printing, gravure printing, planography printing, or stencil printing), an ink-jet method, a coating method, and the like.

For the second electrode 103 functioning as a cathode, any of metals, alloys, electrically conductive compounds, mixtures thereof, and the like which has a low work function (specifically, a work function of 3.8 eV or lower) is preferably used. Specifically, in addition to elements belonging to Group 1 or 2 of the periodic table, that is, alkali metals such as lithium and cesium, alkaline earth metals such as magnesium, calcium, and strontium, alloys thereof (e.g., Mg—Ag and Al—Li), rare earth metals such as europium and ytterbium, and alloys thereof, aluminum, silver, or the like can be used. When a layer included in the EL layer 102 which is formed in contact with the second electrode 103 is formed using the composite material in which the organic compound and the electron donor (donor) which are described above are mixed, as a substance for the second electrode 103, any of a variety of conductive materials such as Al, Ag, ITO, and indium oxide-tin oxide containing silicon or silicon oxide can be used regardless of the work function.

The second electrode 103 can be formed by a vacuum evaporation method or a sputtering method. In the case of using a silver paste or the like, a coating method, an ink-jet method, or the like can be used.

In the above light-emitting element, a current flows due to a potential difference between the first electrode 101 and the second electrode 103, and holes and electrons recombine in the EL layer 102, so that light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element including only a fluorescent compound.

Note that the structure described in this embodiment can be used in combination with any of the structures described in the other embodiments, as appropriate.

Embodiment 4

Described in this embodiment is a light-emitting element (hereinafter referred to as a tandem light-emitting element) with a structure in which the organometallic complex of one embodiment of the present invention is used as an EL material in an EL layer and a plurality of EL layers are provided with a charge-generation layer provided therebetween.

Figure 2A:
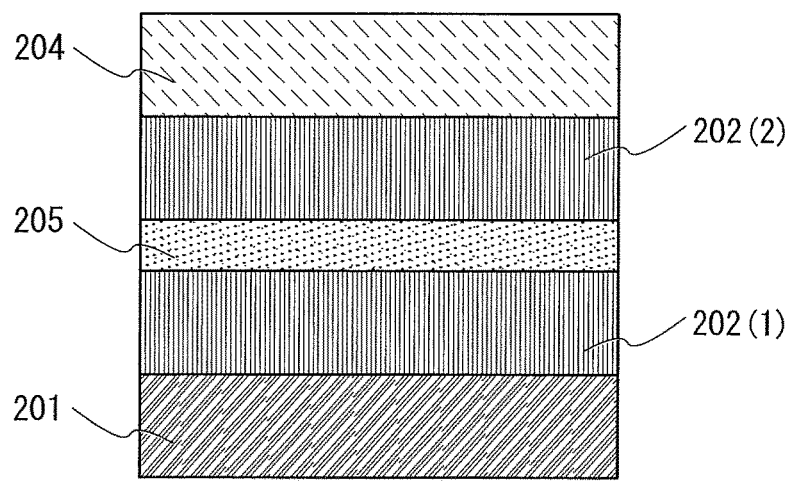
FIGS. 2A and 2B each illustrate the structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode and the second electrode 204 functions as a cathode. Note that the first electrode 201 and the second electrode 204 can each have a structure similar to that described in Embodiment 3. In addition, one or both of the plurality of EL layers (the first EL layer 202(1) and the second EL layer 202(2)) may have a structure similar to that described in Embodiment 3. In other words, the structures of the first EL layer 202(1) and the second EL layer 202(2) may be the same or different from each other and can be similar to that described in Embodiment 3.

A charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when a voltage is applied to the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or BSPB, or the like can be used. The substances described here are mainly substances having a hole mobility of $10^4$ cm$^2$/Vs or higher. However, other substances may also be used as long as their hole-transport properties are higher than their electron-transport properties.

As the electron acceptor, 7,7,8,8-tetracyano-2,3,5,6-tetrafluoroquinodimethane (abbreviation: F$_4$-TCNQ), chloranil, or the like can be used. Moreover, an oxide of any of metals belonging to Groups 4 to 8 of the periodic table can be used. Specifically, it is preferable to use vanadium oxide, niobium oxide, tantalum oxide, chromium oxide, molybdenum oxide, tungsten oxide, manganese oxide, or rhenium oxide because of their high electron accepting properties. In particular, molybdenum oxide is preferable because it is stable in the air, has a low hygroscopic property, and is easy to handle.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$, can be used. Alternatively, in addition to such a metal complex, PBD, OXD-7, TAZ, BPhen, BCP, or the like can be used. The substances described here are mainly substances having an electron mobility of $10^{-6}$ cm$^2$IVs or higher. However, other substances may also be used as long as their electron-transport properties are higher than their hole-transport properties.

As the electron donor, it is possible to use an alkali metal, an alkaline earth metal, a rare earth metal, a metal belonging to Group 2 or 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may also be used as the electron donor.

By forming the charge-generation layer 205 with any of the above materials, it is possible to suppress an increase in driving voltage caused when the EL layers are stacked.

Figure 2B:
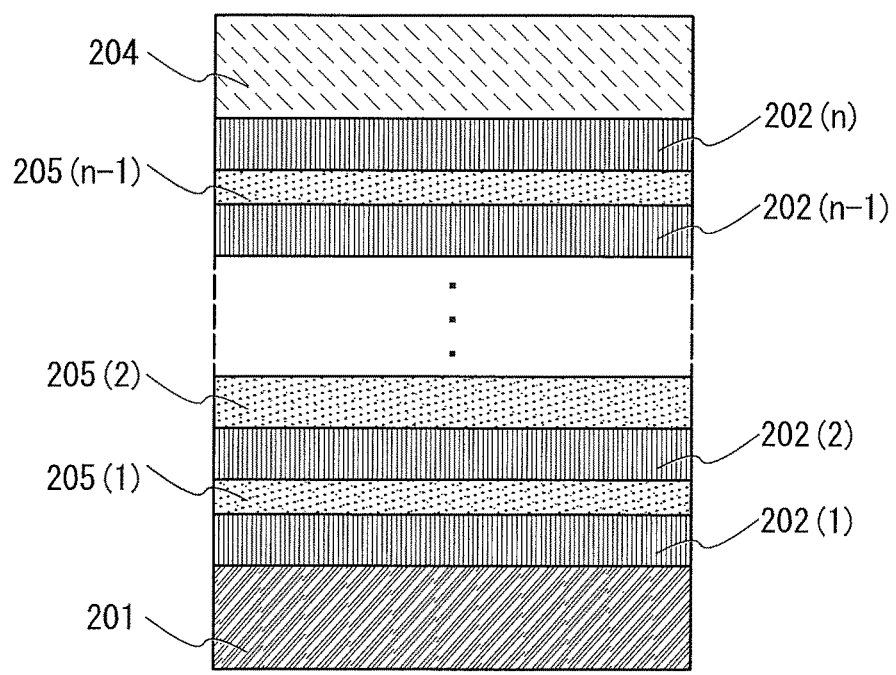

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are provided between a pair of electrodes, by providing charge-generation layers (205(1) to 205(n−1)) between the EL layers as in the light-emitting element of this embodiment, light emission in a high luminance region can be obtained with current density kept low. Since the current density can be kept low, the element can have a long lifetime. When the light-emitting element is applied to a light-emitting device, an electronic device, a lighting device, and the like each having a large light-emitting area, uniform light emission in a large area is possible since voltage drop due to resistance of an electrode material can be reduced.

When the EL layers have different emission colors, a desired emission color can be obtained from the light-emitting element as a whole. For example, in the light-emitting element including two EL layers, when the emission color of a first EL layer and the emission color of a second EL layer are made to be complementary colors, the light-emitting element can emit white light as a whole. Note that "complementary color" means a relation between colors which become an achromatic color when they are mixed. In other words, when lights which are complementary to each other are mixed, white light emission can be obtained.

A light-emitting element including three EL layers can also emit white light as a whole, when the emission color of a first EL layer is red, the emission color of a second EL layer is green, and the emission color of a third EL layer is blue, for example.

Note that the structure described in this embodiment can be combined with any of the structures described in the other embodiments, as appropriate.

Embodiment 5

In this embodiment, a light-emitting device including a light-emitting element in which the organometallic complex of one embodiment of the present invention is used for an EL layer will be described.

The light-emitting device may be either a passive matrix light-emitting device or an active matrix light-emitting device. Any of the light-emitting elements described in the other embodiments can be used for the light-emitting device described in this embodiment.

In this embodiment, an active matrix light-emitting device is first described with reference to FIGS. 3A and 3B.

Figure 3A:
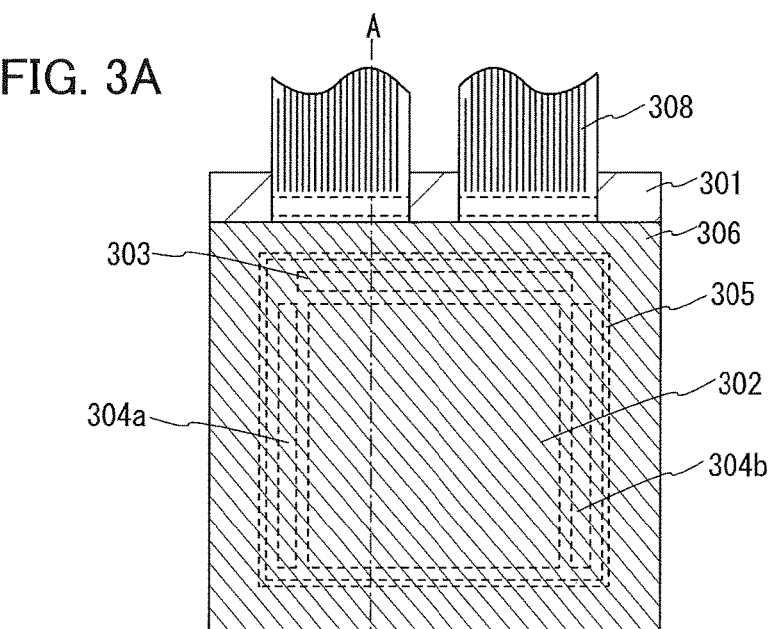
FIGS. 3A to 3C illustrate a light-emitting device.
Figure 3B:
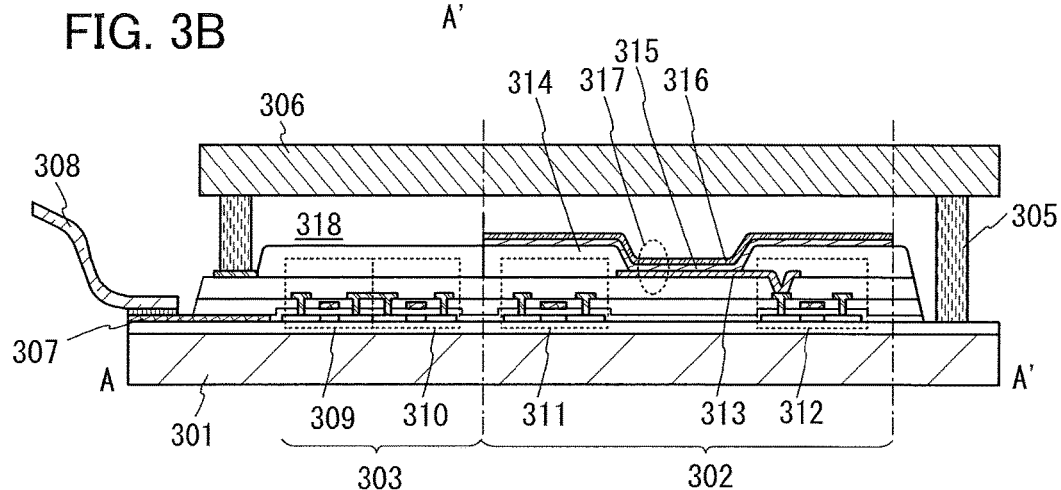

Note that FIG. 3A is a top view illustrating a light-emitting device and FIG. 3B is a cross-sectional view taken along dashed-dotted line A-A' in FIG. 3A. The active matrix light-emitting device of this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal is provided, through which a signal (e.g., a video signal, a clock signal, a start signal, a reset signal, or the like) or potential from the outside is transmitted to the driver circuit portion 303 and the driver circuit portions 304a and 304b. Here is shown an example in which a FPC 308 is provided as the external input terminal. Although only the FPC is shown here, the FPC may be provided with a printed wiring board (PWB). The light-emitting device in this specification includes not only a main body of the light-emitting device but also a light-emitting device with an FPC or a PWB attached.

Next, a cross-sectional structure will be described with reference to FIG. 3B. The driver circuit portions and the pixel portion are formed over the element substrate 301; here are illustrated the driver circuit portion 303 which is the source line driver circuit and the pixel portion 302.

In the driver circuit portion 303, an FET 309 and an FET 310 are combined as an example. Note that the driver circuit portion 303 may be formed with a circuit including transistors having the same conductivity type (either n-channel transistors or p-channel transistors) or a CMOS circuit including an n-channel transistor and a p-channel transistor. Although a driver integrated type in which the driver circuit is formed over the substrate is described in this embodiment, the driver circuit is not necessarily formed over the substrate and can be formed outside, not over the substrate.

The pixel portion 302 includes a plurality of pixels each of which includes a switching FET 311, a current control FET 312, and a first electrode 313 that is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. Examples of a semiconductor material that can be used for the FETs 309, 310, 311, and 312 include semiconductors belonging to Group 13 of the periodic table, semiconductors belonging to Group 14 of the periodic table, compound semiconductors, oxide semiconductors, and organic semiconductors. In addition, there is no particular limitation on the crystallinity of the semiconductor material, and an amorphous semiconductor film or a crystalline semiconductor film can be used, for example. In particular, an oxide semiconductor is preferably used for the FETs 309, 310, 311, and 312. Examples of the oxide semiconductor include an In—Ga oxide and an In-M-Zn oxide (M represents Al, Ga, Y, Zr, La, Ce, or Nd). For example, an oxide semiconductor material that has an energy gap of 2 eV or more, preferably 2.5 eV or more, more preferably 3 eV or more is used for the FETs 309, 310, 311, and 312, so that the off-state current of the transistors can be reduced.

In addition, an insulator 314 is formed to cover an end portion of the first electrode 313. In this embodiment, the insulator 314 is formed using a positive photosensitive acrylic resin. The first electrode 313 is used as an anode in this embodiment.

The insulator 314 preferably has a curved surface with curvature at its upper end portion or lower end portion. This enables the coverage with a film formed over the insulator 314 to be favorable. The insulator 314 can be formed using, for example, either a negative photosensitive resin or a positive photosensitive resin. The material of the insulator 314 is not limited to an organic compound, and an inorganic compound such as silicon oxide, silicon oxynitride, or silicon nitride can be used.

A light-emitting element 317 has a stacked-layer structure including the first electrode (anode) 313, an EL layer 315, and a second electrode (cathode) 316, and the EL layer 315 includes at least a light-emitting layer. Furthermore, in the EL layer 315, a hole-injection layer, a hole-transport layer, an electron-transport layer, an electron-injection layer, a charge-generation layer, and the like can be provided as appropriate in addition to the light-emitting layer.

For the first electrode 313, the EL layer 315, and the second electrode 316, any of the materials given in Embodiment 3 can be used. Although not illustrated, the second electrode 316 is electrically connected to the FPC 308 which is an external input terminal.

Although the cross-sectional view of FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, any of light-emitting elements that emit light of white (W), yellow (Y), magenta (M), cyan (C), and the like may be formed. For example, when any of the light-emitting elements that emit light of a plurality of kinds of colors is used in combination with the light-emitting elements that emit light of three kinds of colors (R, G, and B), effects such as an improvement in color purity and a reduction in power consumption can be obtained. In addition, a light-emitting device capable of full color display may be manufactured by combination with color filters. Furthermore, the light-emitting device may have an improved emission efficiency and a reduced power consumption by combination with quantum dots.

The sealing substrate 306 is attached to the element substrate 301 with the sealant 305, so that the light-emitting element 317 is provided in a space 318 surrounded by the element substrate 301, the sealing substrate 306, and the sealant 305. The space 318 may be filled with an inert gas (such as nitrogen or argon) or the sealant 305. In the case where the sealant is applied and then the substrates are attached, UV treatment, heat treatment, or a combination thereof is preferably performed.

An epoxy-based resin or glass frit is preferably used for the sealant 305. Such a material preferably allows as little moisture and oxygen as possible to penetrate. As the sealing substrate 306, a glass substrate, a quartz substrate, or a plastic substrate formed of fiber reinforced plastic (FRP), polyvinyl fluoride (PVF), polyester, acrylic, or the like can be used. In the case where glass frit is used as the sealant, the element substrate 301 and the sealing substrate 306 are preferably glass substrates in terms of adhesion.

In this manner, the active matrix light-emitting device can be obtained.

The light-emitting device including the light-emitting element in which the organometallic complex of one embodiment of the present invention is used for the EL layer may be a passive matrix light-emitting device, as well as the above-described active matrix light-emitting device.

Figure 3C:
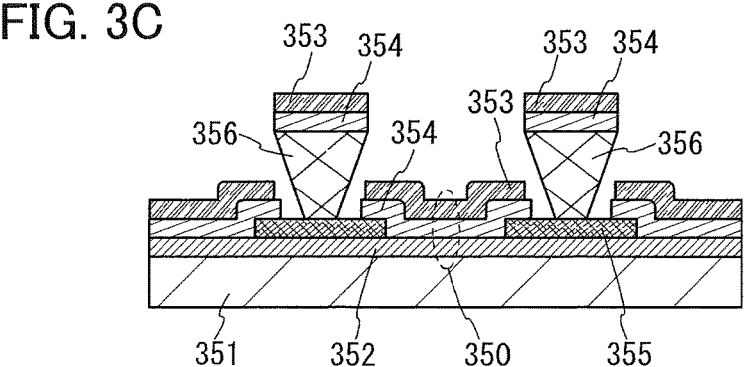

FIG. 3C is a cross-sectional view illustrating a pixel portion of a passive matrix light-emitting device.

As illustrated in FIG. 3C, a light-emitting element 350 including a first electrode 352, an EL layer 354, and a second electrode 353 is formed over a substrate 351. Although not illustrated, a plurality of first electrodes 352 are formed in the form of stripes over the substrate 351, and an insulating film 355 is formed over the first electrodes 352 to cover end portions of the first electrodes 352. The insulating film 355 includes an opening in part of a region over the first electrode 352.

A partition 356 formed using an insulating material is provided over the insulating film 355. The sidewalls of the partition 356 slope so that the distance between the sidewalls is gradually narrowed toward the surface of the substrate. In other words, a cross section taken along the direction of the short side of the partition 356 is trapezoidal, and the lower side (a side which is in the same direction as a plane direction of the insulating film 355 and in contact with the insulating film 355) is shorter than the upper side (a side which is in the same direction as the plane direction of the insulating film 355 and not in contact with the insulating film 355). The partition 356 thus provided can prevent defects in the light-emitting element due to static electricity or the like. After the partition 356 is formed, the EL layer 354 is formed, so that the EL layer 354 is in contact with the first electrode 352 in an opening in part of a region over the first electrode 352.

After the formation of the EL layer 354, the second electrode 353 is formed. Thus, the second electrode 353 is formed over the EL layer 354 (in some cases, over the insulating film 355) without contact with the first electrode 352. Since the EL layer 354 and the second electrode 353 are formed after the formation of the partition 356, the EL layer 354 and the second electrode 353 are also sequentially stacked over the partition 356.

Note that sealing can be performed as in the case of the active matrix light-emitting device and is thus not described here.

In this manner, the passive matrix light-emitting device can be obtained.

In this specification and the like, a transistor or a light-emitting element can be formed using any of a variety of substrates, for example. The type of a substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate such as a stainless steel substrate or a tungsten substrate, and a flexible substrate such as a laminate film, paper containing a fibrous material, or a base material film. Examples of the glass substrate include a barium borosilicate glass substrate, an aluminoborosilicate glass substrate, and a soda lime glass substrate. Examples of the flexible substrate include substrates forming of plastics typified by polyethylene terephthalate (PET), polyethylene naphthalate (PEN), polyether sulfone (PES), polytetrafluoroethylene (PTFE), polypropylene, polyester, polyvinyl fluoride, polyvinyl chloride, polyamide, polyimide, aramid, or an epoxy resin; a synthetic resin such as acrylic; an inorganic film forming by evaporation; and paper.

The use of a semiconductor substrate, a single crystal substrate, an SOI substrate, or the like enables the manufacture of small-sized transistors with few variations in characteristics, size, shape, or the like. A circuit using such transistors achieves lower power consumption or higher integration.

In the case where any of the above-described flexible substrates is used as a substrate, a transistor or a light-emitting element may be provided directly over the flexible substrate. Alternatively, part of or the entire transistor or light-emitting element may be formed over a substrate with a separation layer provided therebetween and separated from the substrate and transferred to another substrate. When the transistor or the light-emitting element is transferred to another substrate by using a separation layer as described above, the transistor or the light-emitting element can be formed over a substrate having low heat resistance or a flexible substrate over which the transistor or the light-emitting element is directly formed with difficulty. For the separation layer, a stack including inorganic films such as a tungsten film and a silicon oxide film, or an organic resin film of polyimide or the like formed over a substrate can be used, for example.

Note that the structure described in this embodiment can be combined with any of the structures described in the other embodiments, as appropriate.

Embodiment 6

In this embodiment, examples of an electronic device manufactured using the light-emitting device of one embodiment of the present invention will be described with reference to FIGS. 4A to 4D.

Examples of the electronic device to which the light-emitting device is applied include television devices (also referred to as TV or television receivers), monitors for computers and the like, cameras such as digital cameras and digital video cameras, digital photo frames, mobile phones (also referred to cellular phones or mobile phone devices), portable game machines, portable information terminals, audio playback devices, and stationary game machines such as pin-ball machines.

Figure 4A:
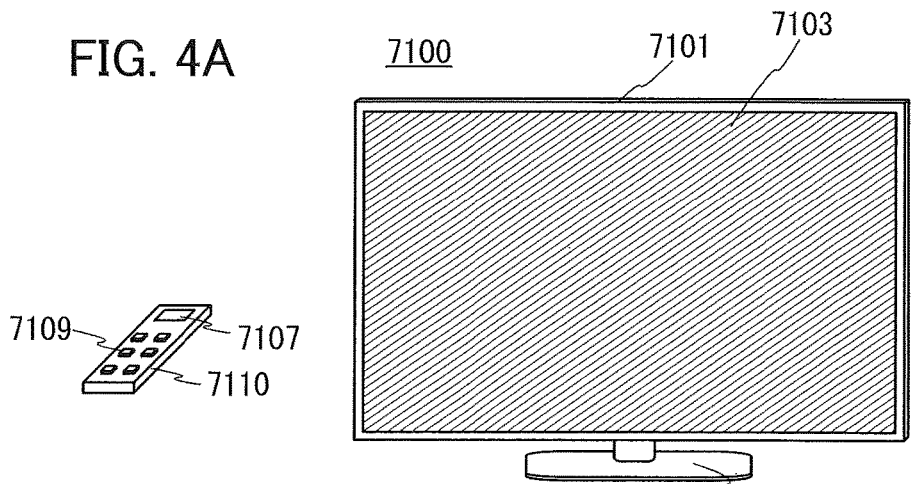

FIG. 4A illustrates an example of a television device. In a television device 7100, a display portion 7103 is incorporated in a housing 7101. The display portion 7103 can display images and may be a touch panel (an input/output device) including a touch sensor (an input device). Note that the light-emitting device of one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 may be provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) data communication can be performed.

Figure 4B:
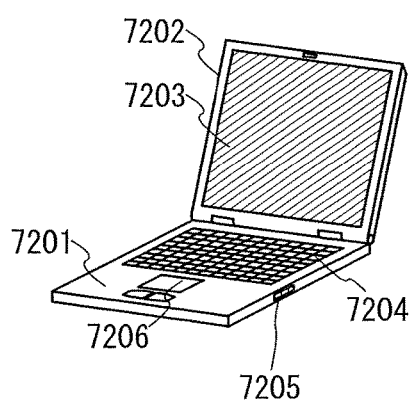

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device of one embodiment of the present invention for the display portion 7203. The display portion 7203 may be a touch panel (an input/output device) including a touch sensor (an input device).

Figure 4C:
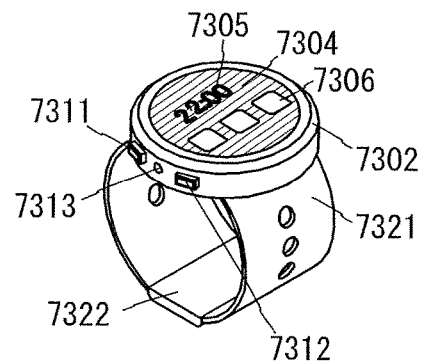

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 4C can have a variety of functions, for example, a function of displaying a variety of data (e.g., a still image, a moving image, and a text image) on a display portion, a touch panel function, a function of displaying a calendar, date, time, and the like, a function of controlling processing with a variety of software (programs), a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. Note that the smart watch can be manufactured using the light-emitting device of one embodiment of the present invention for the display panel 7304.

Figure 4D:
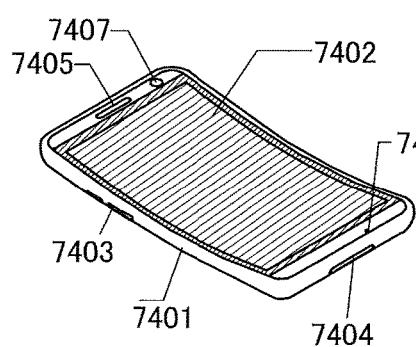

FIG. 4D illustrates an example of a mobile phone (e.g., smartphone). A mobile phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 with a curved surface as illustrated in FIG. 4D.

When the display portion 7402 of the mobile phone 7400 illustrated in FIG. 4D is touched with a finger or the like, data can be input to the mobile phone 7400. Furthermore, operations such as making a call and creating an e-mail can be performed by touching the display portion 7402 with a finger or the like.

There are mainly three screen modes for the display portion 7402. The first mode is a display mode mainly for displaying an image. The second mode is an input mode mainly for inputting data such as text. The third mode is a display-and-input mode in which two modes, the display mode and the input mode, are combined.

For example, in the case of making a call or creating an e-mail, a text input mode mainly for inputting text is selected for the display portion 7402 so that text displayed on the screen can be input. In that case, it is preferable to display a keyboard or number buttons on almost the entire screen of the display portion 7402.

When a detection device such as a gyroscope or an acceleration sensor is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touch on the display portion 7402 or operation with the operation button 7403 of the housing 7401. The screen modes can also be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

If an optical sensor in the display portion 7402 judges that the input by touch on the display portion 7402 is not performed for a certain period in the input mode, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Furthermore, when a backlight or a sensing light source which emits near-infrared light is provided in the display portion, an image of a finger vein, a palm vein, or the like can be taken.

Figures 1, 2, 4D:
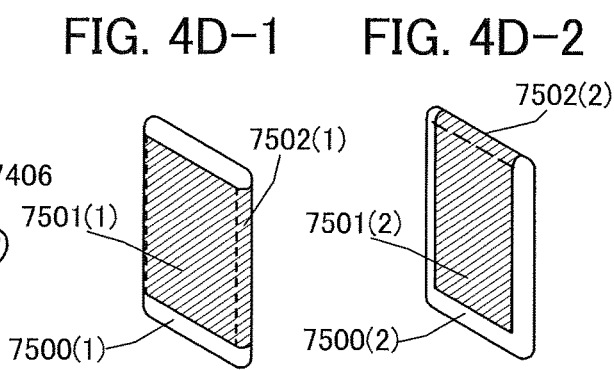

The light-emitting device of one embodiment of the present invention can also be used for a mobile phone having a structure illustrated in FIG. 4D-1 or 4D-2, which is another structure of the mobile phone (e.g., smartphone).

In the case of the structure illustrated in FIG. 4D-1 or 4D-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the mobile phone is placed in user's breast pocket.

Figure 5A:
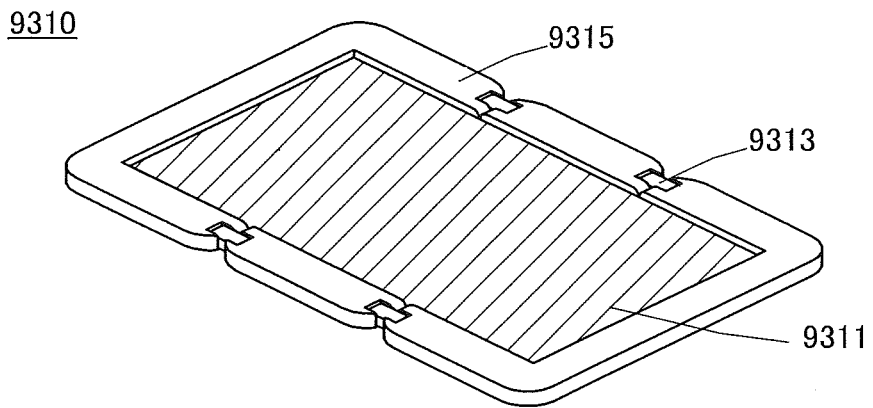
FIGS. 5A to 5C illustrate an electronic device.
Figure 5B:
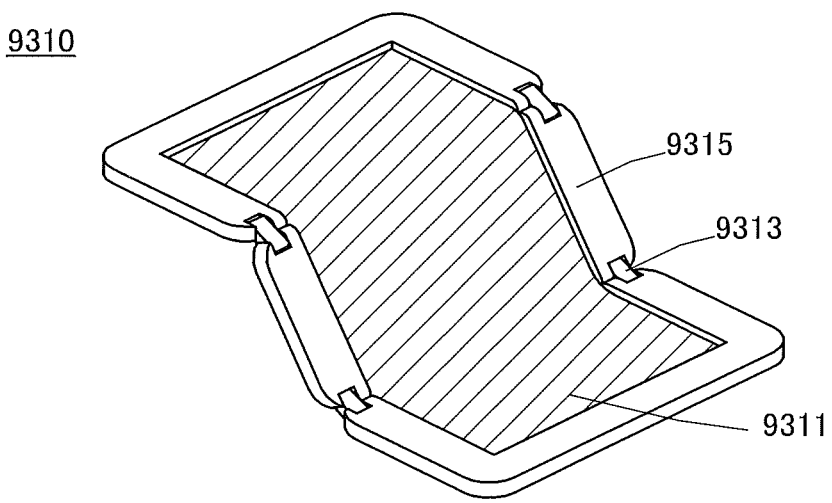
Figure 5C:
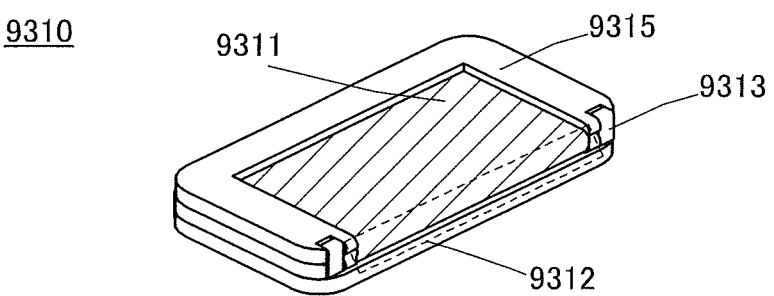

FIGS. 5A to 5C illustrate a foldable portable information terminal 9310. FIG. 5A illustrates the portable information terminal 9310 that is opened. FIG. 5B illustrates the portable information terminal 9310 that is being opened or being folded. FIG. 5C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 is a display region that is positioned at the side surface of the portable information terminal 9310 that is folded. On the display region 9312, information icons, file shortcuts of frequently used applications or programs, and the like can be displayed, and confirmation of information and start of application can be smoothly performed.

As described above, the light-emitting device of one embodiment of the present invention can be used for electronic devices in a variety of fields without being limited to those described in this embodiment.

Note that the structure described in this embodiment can be combined with any of the structures described in the other embodiments, as appropriate.

Embodiment 7

In this embodiment, the structure of a lighting device manufactured using the light-emitting element of one embodiment of the present invention will be described with reference to FIGS. 6A to 6D.

Figure 6A:
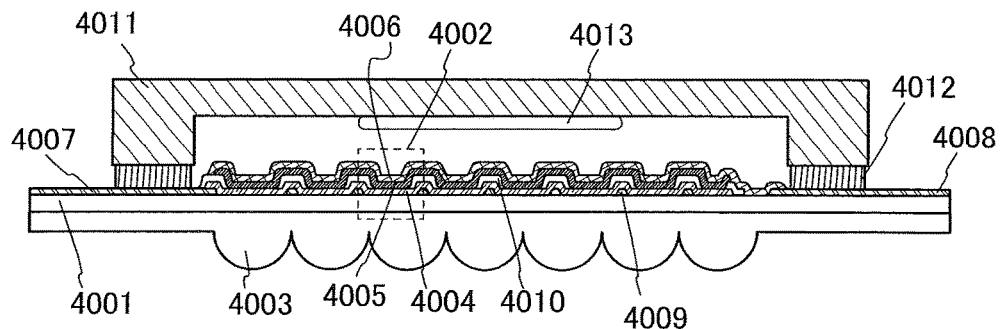
FIGS. 6A to 6D each illustrate a lighting device.
Figure 6B:
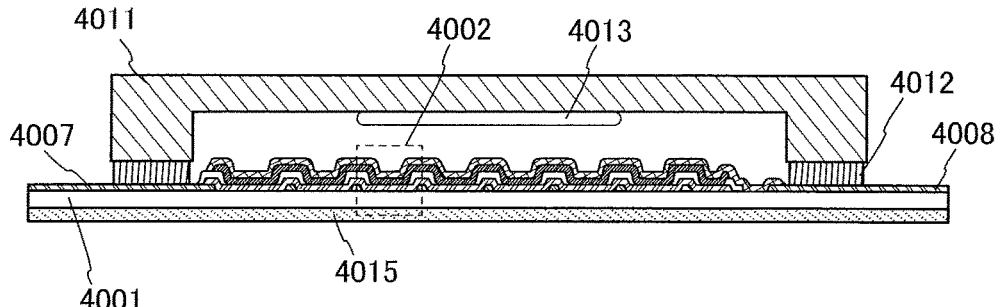
Figure 6C:
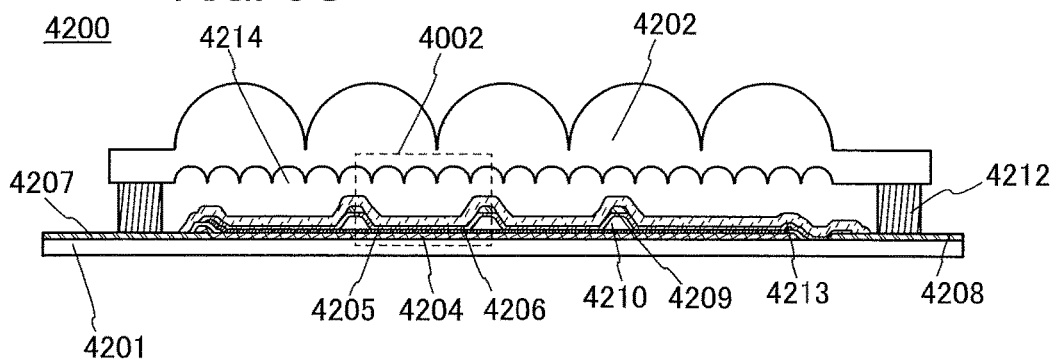
Figure 6D:
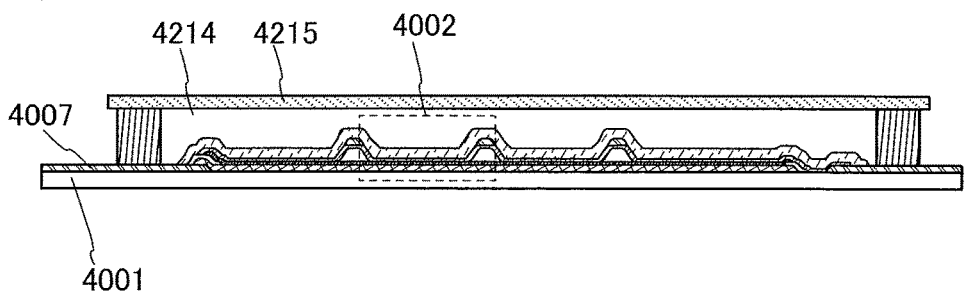

FIGS. 6A to 6D are each an example of a cross-sectional view of a lighting device. FIGS. 6A and 6B illustrate bottom-emission lighting devices in which light is extracted from the substrate side, and FIGS. 6C and 6D illustrate top-emission lighting devices in which light is extracted from the sealing substrate side.

A lighting device 4000 illustrated in FIG. 6A includes a light-emitting element 4002 over a substrate 4001. In addition, the lighting device 4000 includes a substrate 4003 with unevenness on the outer surface of the substrate 4001. The light-emitting element 4002 includes a first electrode 4004, an EL layer 4005, and a second electrode 4006.

The first electrode 4004 is electrically connected to an electrode 4007. The second electrode 4006 is electrically connected to an electrode 4008. An auxiliary wiring 4009 electrically connected to the first electrode 4004 may be provided. Note that an insulating layer 4010 is provided over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 6A, whereby the extraction efficiency of light emitted from the light-emitting element 4002 can be increased.

Instead of the substrate 4003, a diffusion plate 4015 may be provided on the outer surface of the substrate 4001 as in a lighting device 4100 illustrated in FIG. 6B.

A lighting device 4200 illustrated in FIG. 6C includes the light-emitting element 4002 over a substrate 4201. The light-emitting element 4002 includes a first electrode 4204, an EL layer 4205, and a second electrode 4206.

The first electrode 4204 is electrically connected to an electrode 4207. The second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4202 with unevenness are bonded to each other with a sealant 4212. A barrier film 4213 and a planarization film 4214 may be provided between the sealing substrate 4202 and the light-emitting element 4002. The sealing substrate 4202 has the unevenness illustrated in FIG. 6C, whereby the extraction efficiency of light emitted from the light-emitting element 4002 can be increased.

Instead of the sealing substrate 4202, a diffusion plate 4215 may be provided over the light-emitting element 4002 as in a lighting device 4300 illustrated in FIG. 6D.

Note that the EL layers 4005 and 4205 in this embodiment can contain the organometallic complex of one embodiment of the present invention. In that case, a lighting device with low power consumption can be provided.

Note that the structure described in this embodiment can be combined with any of the structures described in the other embodiments, as appropriate.

Embodiment 8

In this embodiment, examples of a lighting device to which the light-emitting device of one embodiment of the present invention is applied will be described with reference to FIG. 7.

Figure 7:
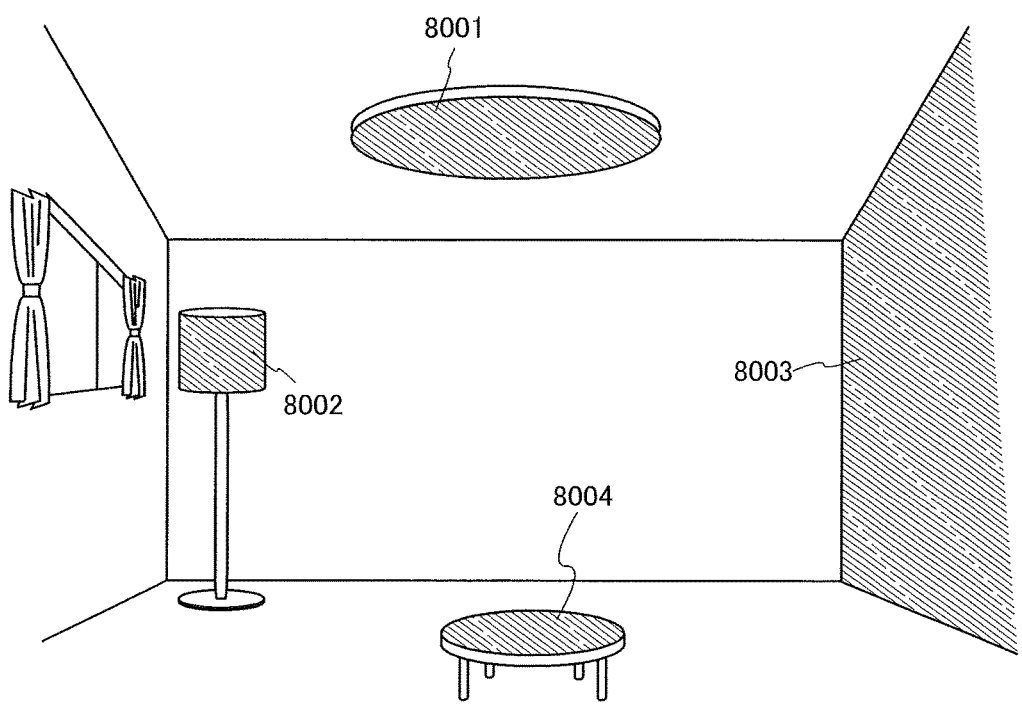
FIG. 7 illustrates lighting devices.

FIG. 7 illustrates an example in which the light-emitting device is used for an indoor lighting device 8001. Since the area of the light-emitting device can be increased, a lighting device having a large area can be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Furthermore, the wall of a room may be provided with a large-sized lighting device 8003.

When the light-emitting device is used for a table by being used as the surface of the table, a lighting device 8004 which has a function of the table can be obtained. When the light-emitting device is used as part of other furniture, a lighting device which has a function of the corresponding furniture can be obtained.

In this manner, a variety of lighting devices to which the light-emitting device is applied can be obtained. Note that such lighting devices are also embodiments of the present invention.

Note that the structure described in this embodiment can be combined with any of the structures described in the other embodiments, as appropriate.

Embodiment 9

In this embodiment, a touch panel including the light-emitting element or the light-emitting device of one embodiment of the present invention will be described with reference to FIGS. 8A and 8B, FIGS. 9A and 9B, FIGS. 10A and 10B, FIGS. 11A and 11B, and FIG. 12.

Figure 8A:
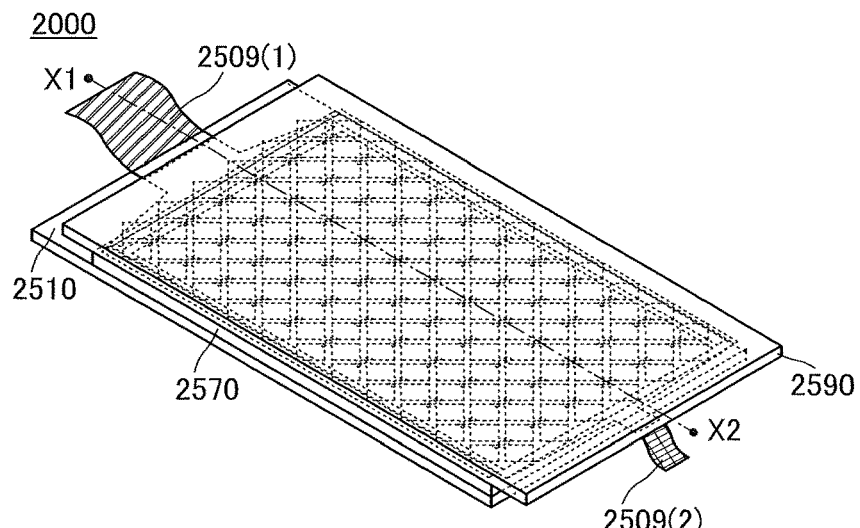
FIGS. 8A and 8B illustrate an example of a touch panel.
Figure 8B:
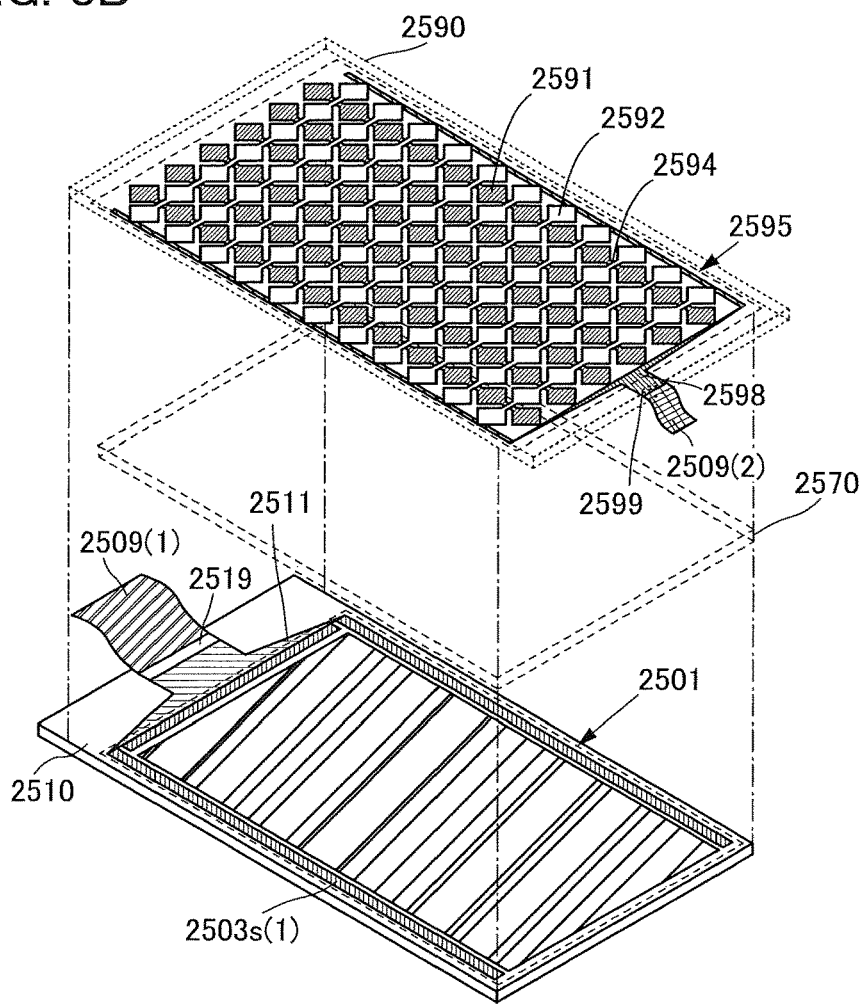

FIGS. 8A and 8B are perspective views of a touch panel 2000. Note that FIGS. 8A and 8B illustrate only main components of the touch panel 2000 for simplicity.

The touch panel 2000 includes a display portion 2501 and a touch sensor 2595 (see FIG. 8B). Furthermore, the touch panel 2000 includes a substrate 2510, a substrate 2570, and a substrate 2590. Note that the substrate 2510, the substrate 2570, and the substrate 2590 each have flexibility.

The display portion 2501 includes a plurality of pixels over the substrate 2510 and a plurality of wirings 2511 through which a signal is supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 8B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor include a surface capacitive touch sensor and a projected capacitive touch sensor.

Examples of the projected capacitive touch sensor include a self-capacitive touch sensor and a mutual capacitive touch sensor, which differ from each other mainly in the driving method. The use of a mutual capacitive touch sensor is preferable because multiple points can be sensed simultaneously.

First, an example of using a projected capacitive touch sensor is described with reference to FIG. 8B. Note that in the case of a projected capacitive touch sensor, a variety of sensors that can sense the approach or contact of an object such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction as illustrated in FIGS. 8A and 8B. In the same manner, the electrodes 2591 each have a shape of a plurality of quadrangles arranged in one direction with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle of greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, variation in luminance of light passing through the touch sensor 2595 can be reduced.

Note that the shapes of the electrodes 2591 and the electrodes 2592 are not limited to the above-mentioned shapes and can be any of a variety of shapes. For example, a plurality of electrodes 2591 may be provided so that a space between the electrodes 2591 is reduced as much as possible, and a plurality of electrodes 2592 may be provided with an insulating layer provided between the electrodes 2591 and the electrodes 2592. In that case, between two adjacent electrodes 2592, it is preferable to provide a dummy electrode which is electrically insulated from these electrodes, because the area of a region having a different transmittance can be reduced.

Figure 9A:
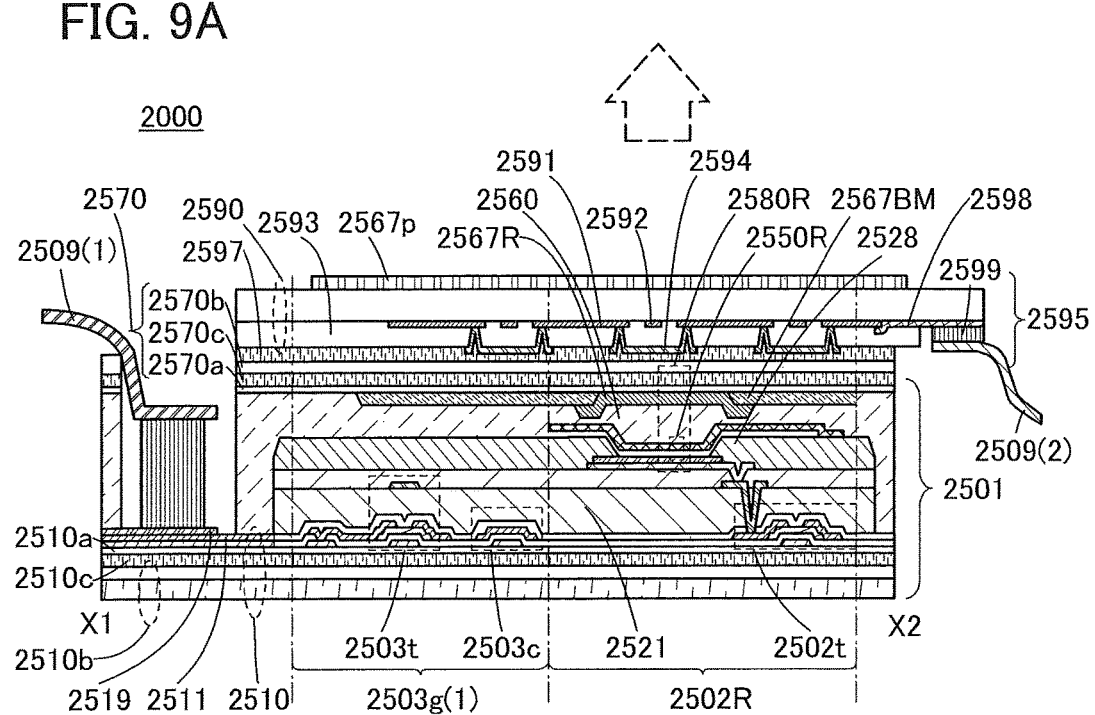
FIGS. 9A and 9B illustrate an example of a touch panel.

Next, the touch panel 2000 will be described in detail with reference to FIGS. 9A and 9B. FIG. 9A is a cross-sectional view taken along dashed-dotted line X1-X2 in FIG. 8A.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

An adhesive layer 2597 is provided under the wiring 2594. The substrate 2590 is attached to the substrate 2570 with the adhesive layer 2597 so that the touch sensor 2595 overlaps with the display portion 2501.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film including graphene oxide. As a reducing method, a method using heat or the like can be employed.

For example, the electrodes 2591 and the electrodes 2592 can be formed by depositing a light-transmitting conductive material on the substrate 2590 by a sputtering method and then removing an unnecessary portion by any of various patterning techniques such as photolithography.

Examples of a material used for the insulating layer 2593 include a resin such as acrylic or epoxy, a resin having a siloxane bond such as silicone, and an inorganic insulating material such as silicon oxide, silicon oxynitride, or aluminum oxide.

The wiring 2594 is formed in an opening provided in the insulating layer 2593, whereby the adjacent electrodes 2591 are electrically connected to each other. A light-transmitting conductive material can be favorably used for the wiring 2594 because the aperture ratio of the touch panel can be increased. Moreover, a material having higher conductivity than the electrodes 2591 and 2592 can be favorably used for the wiring 2594 because electric resistance can be reduced.

Through the wiring 2594, a pair of electrodes 2591 are electrically connected to each other. Between the pair of electrodes 2591, the electrode 2592 is provided.

The wiring 2598 is electrically connected to any of the electrodes 2591 and 2592. Part of the wiring 2598 serves as a terminal. For the wiring 2598, for example, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display portion 2501 includes a plurality of pixels arranged in a matrix. Each of the pixels includes a display element and a pixel circuit for driving the display element.

For the substrate 2510 and the substrate 2570, for example, a flexible material having a vapor permeability of $10^{-5}$ g/(m$^2$·day) or lower, preferably $10^{-6}$ g/(m$^2$·day) or lower can be favorably used. Note that materials whose thermal expansion coefficients are substantially equal to each other are preferably used for the substrates 2510 and 2570. For example, the coefficients of linear expansion of the materials are preferably $1\times10^{-3}$/K or lower, more preferably $5\times10^{-5}$/K or lower, still more preferably $1\times10^{-5}$/K or lower.

A sealing layer 2560 preferably has a higher refractive index than the air. In the case where light is extracted to the sealing layer 2560 side as illustrated in FIG. 9A, the sealing layer 2560 can also serve as an optical element.

The display portion 2501 includes a pixel 2502R. The pixel 2502R includes a light-emitting module 2580R.

The pixel 2502R includes a light-emitting element 2550R and a transistor 2502t that can supply power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode.

In the case where the sealing layer 2560 is provided on the light extraction side, the sealing layer 2560 is in contact with the light-emitting element 2550R and the coloring layer 2567R.

The coloring layer 2567R overlaps with the light-emitting element 2550R. Accordingly, part of light emitted from the light-emitting element 2550R passes through the coloring layer 2567R and is emitted outside of the light-emitting module 2580R as indicated by an arrow in FIG. 9A.

The display portion 2501 includes a light-blocking layer 2567BM on the light extraction side. The light-blocking layer 2567BM is provided so as to surround the coloring layer 2567R.

The display portion 2501 includes an anti-reflective layer 256'7p in a region that overlaps with the pixels. As the anti-reflective layer 2567p, a circular polarizing plate can be used, for example.

An insulating layer 2521 is provided in the display portion 2501. The insulating layer 2521 covers the transistor 2502t. With the insulating layer 2521, unevenness caused by the pixel circuit is covered. The insulating layer 2521 may have a function of suppressing diffusion of impurities. This can prevent a reduction in reliability of the transistor 2502t or the like due to diffusion of impurities.

The light-emitting element 2550R is formed over the insulating layer 2521. A partition 2528 is provided so as to overlap with an end portion of the lower electrode in the light-emitting element 2550R. Note that a spacer for controlling the distance between the substrate 2510 and the substrate 2570 may be provided over the partition 2528.

A scan line driver circuit 2503g(1) includes a transistor 2503t and a capacitor 2503c. Note that the driver circuit can be formed in the same process and over the same substrate as those of the pixel circuit.

Over the substrate 2510, the wirings 2511 through which a signal can be supplied are provided. Over the wirings 2511, the terminal 2519 is provided. The FPC 2509(1) is electrically connected to the terminal 2519. The FPC 2509(1) has a function of supplying signals such as a pixel signal and a synchronization signal. Note that a printed wiring board (PWB) may be attached to the FPC 2509(1).

For the display portion 2501, a transistor with any of a variety of structures can be used. In the example illustrated in FIG. 9A, a bottom-gate transistor is used. In each of the transistor 2502t and the transistor 2503t illustrated in FIG. 9A, a semiconductor layer including an oxide semiconductor can be used for a channel region. Alternatively, in each of the transistor 2502t and the transistor 2503t, a semiconductor layer including amorphous silicon can be used for a channel region. Further alternatively, in each of the transistor 2502t and the transistor 2503t, a semiconductor layer including polycrystalline silicon that is obtained by a crystallization process such as laser annealing can be used for a channel region.

Figure 9B:
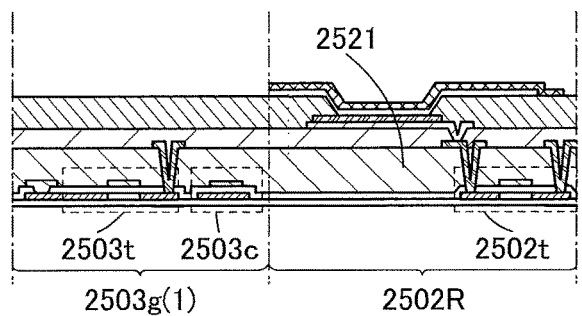

FIG. 9B illustrates the structure of the display portion 2501 in which a top-gate transistor is used.

In the case of a top-gate transistor, as well as the above semiconductor layers that can be used for a bottom-gate transistor, a semiconductor layer including a film that is transferred from a polycrystalline silicon substrate or a single crystal silicon substrate or the like may be used for a channel region.

Next, a touch panel having a structure different from that illustrated in FIGS. 9A and 9B will be described with reference to FIGS. 10A and 10B.

Figure 10A:
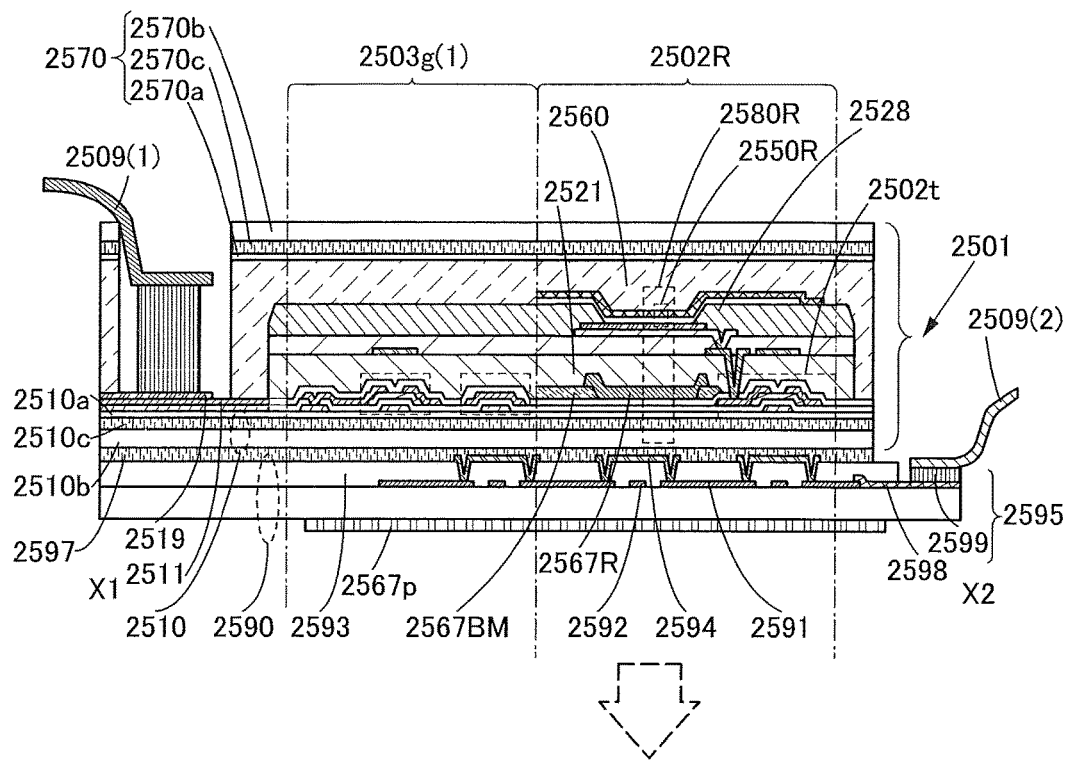
FIGS. 10A and 10B illustrate an example of a touch panel.
Figure 10B:
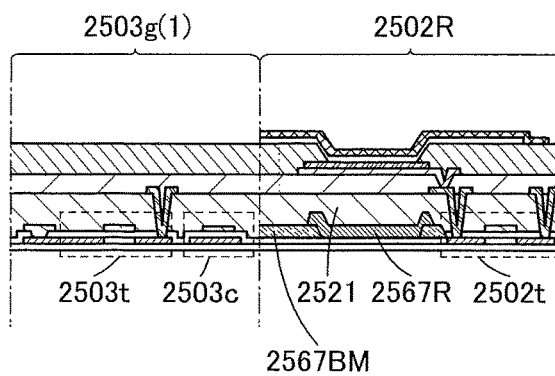

FIG. 10A is a cross-sectional view of a touch panel 2001. The touch panel 2001 illustrated in FIG. 10A differs from the touch panel 2000 illustrated in FIG. 9A in the position of the touch sensor 2595 relative to the display portion 2501. Different structures will be described in detail below, and the above description of the touch panel 2000 can be referred to for the other structures.

The coloring layer 2567R overlaps with the light-emitting element 2550R. The light-emitting element 2550R illustrated in FIG. 10A emits light to the side where the transistor 2502t is provided. Accordingly, part of light emitted from the light-emitting element 2550R passes through the coloring layer 2567R and is emitted outside of the light-emitting module 2580R as indicated by an arrow in FIG. 10A.

The display portion 2501 includes the light-blocking layer 2567BM on the light extraction side. The light-blocking layer 2567BM is provided so as to surround the coloring layer 2567R.

The touch sensor 2595 is provided on the substrate 2510 side of the display portion 2501 (see FIG. 10A).

The display portion 2501 and the touch sensor 2595 are attached to each other with the adhesive layer 2597 provided between the substrate 2510 and the substrate 2590.

In the display portion 2501, a transistor with any of a variety of structures can be used. In the example illustrated in FIG. 10A, a bottom-gate transistor is used. In the example illustrated in FIG. 10B, a top-gate transistor is used.

Next, an example of a method for driving a touch panel will be described with reference to FIGS. 11A and 11B.

Figure 11A:
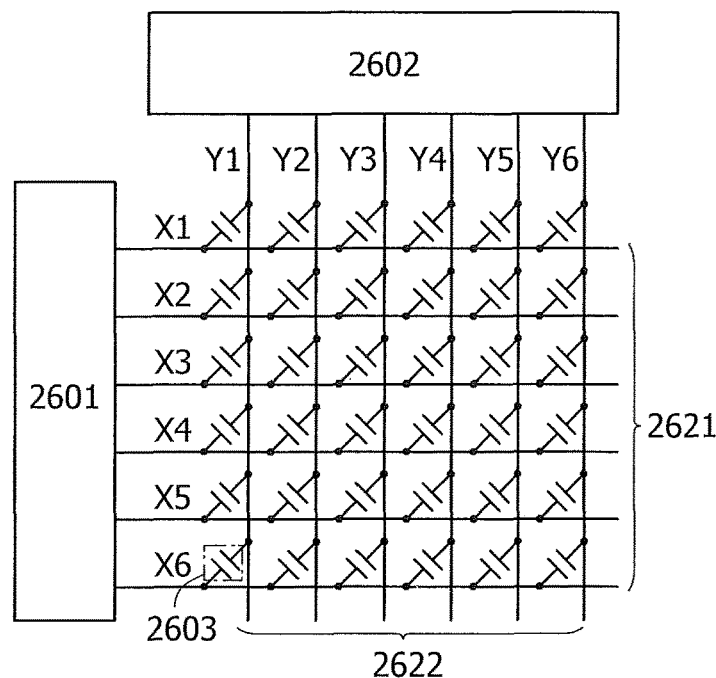
FIGS. 11A and 11B are a block diagram and a timing chart, respectively, of a touch sensor.

FIG. 11A is a block diagram showing the configuration of a mutual capacitive touch sensor. FIG. 11A shows a pulse voltage output circuit 2601 and a current sensing circuit 2602. Note that in FIG. 11A, six wirings X1 to X6 represent electrodes 2621 to which a pulse voltage is applied, and six wirings Y1 to Y6 represent electrodes 2622 that sense changes in current. FIG. 11A also shows capacitors 2603 that are each formed in a region where the electrodes 2621 and 2622 overlap with each other. Note that the functions of the electrodes 2621 and 2622 can be exchanged with each other.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in mutual capacitance in the capacitor 2603. The approach or contact of an object can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of an object, whereas a decrease in current value is sensed when mutual capacitance is decreased owing to the approach or contact of an object. Note that an integrator circuit or the like is used for sensing of current values.

Figure 11B:
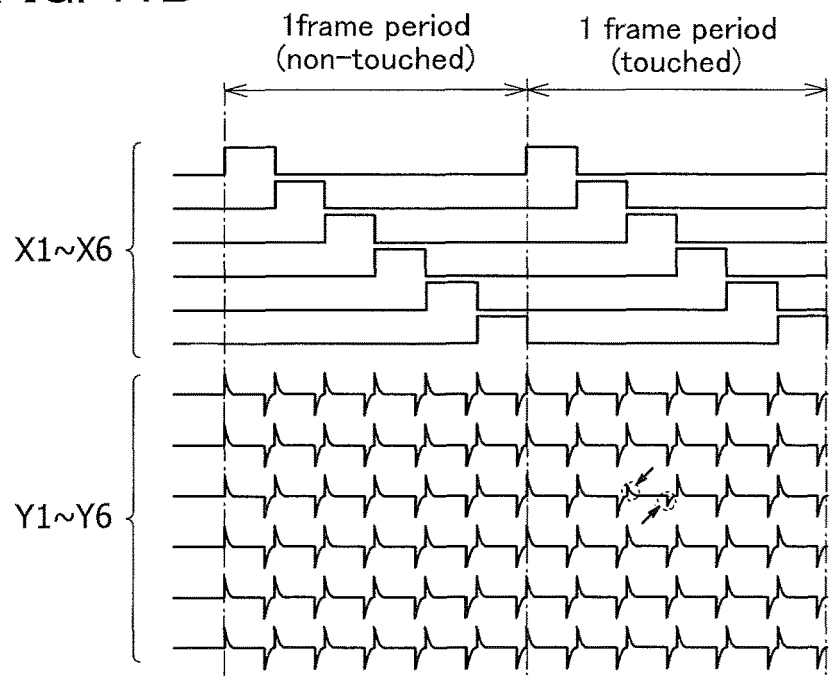

FIG. 11B is a timing chart showing input and output waveforms in the mutual capacitive touch sensor shown in FIG. 11A. In FIG. 11B, sensing of an object is performed in all the rows and columns in one frame period. FIG. 11B shows a period during which an object is not sensed (not touched) and a period during which an object is sensed (touched). Sensed current values of the wirings Y1 to Y6 are shown as the waveforms of voltage values.

A pulse voltage is sequentially applied to the wirings X1 to X6, and waveforms of the wirings Y1 to Y6 change in accordance with the pulse voltage. When there is no approach or contact of an object, the waveforms of the wirings Y1 to Y6 change in accordance with changes in the voltages of the wirings X1 to X6. The current value is decreased at the point of approach or contact of an object and accordingly the waveform of the voltage value changes. By sensing a change in mutual capacitance in this manner, the approach or contact of an object can be sensed.

Figure 12:
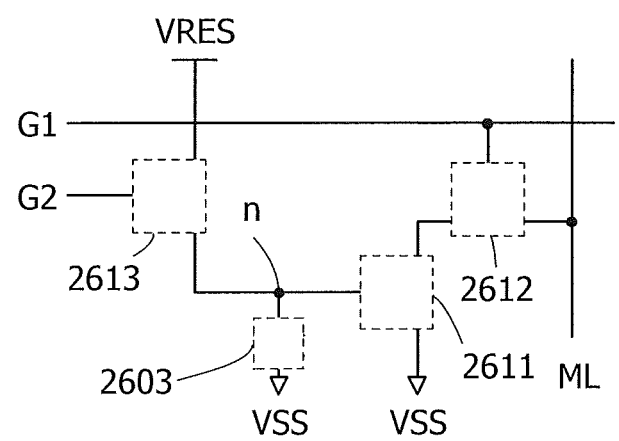
FIG. 12 is a circuit diagram of a touch sensor.

Although FIG. 11A shows a passive matrix touch sensor in which only the capacitor 2603 is provided at the intersection of wirings as a touch sensor, an active matrix touch sensor including a transistor and a capacitor at the intersection may also be used. FIG. 12 shows an example of a sensor circuit included in an active matrix touch sensor.

The sensor circuit shown in FIG. 12 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. A voltage VSS is applied to the other electrode of the capacitor 2603.

Next, the operation of the sensor circuit shown in FIG. 12 will be described. First, a potential for turning on the transistor 2613 is supplied as the signal G2, and a potential corresponding to the voltage VRES is applied to a node n connected to the gate of the transistor 2611. Then, a potential for turning off the transistor 2613 is supplied as the signal G2, so that the potential of the node n is held. Then, mutual capacitance of the capacitor 2603 changes owing to the approach or contact of an object such as a finger, and accordingly the potential of the node n changes from VRES.

In reading operation, a potential for turning on the transistor 2612 is supplied as the signal G1. A current flowing through the transistor 2611, that is, a current flowing through the wiring ML changes in accordance with the potential of the node n. By sensing this current, the approach or contact of an object can be sensed.

In each of the transistors 2611, 2612, and 2613, an oxide semiconductor layer is preferably used as a semiconductor layer in which a channel region is formed. In particular, such a transistor is used as the transistor 2613, so that the potential of the node n can be held for a long time and the frequency of operation of resupplying VRES to the node n (refresh operation) can be reduced.

At least part of this embodiment can be implemented in combination with any of the other embodiments described in this specification, as appropriate.

Example 1

Synthesis Example 1

In this example, a method for synthesizing bis(4-methyldibenzo[f,h]quinazolin-12-yl-κC,κN)(2,4-pentanedionato-κ²O,O')iridium(III) (Abbreviation: [Ir(mdbqz)₂(acac)]) represented by Structural Formula (100) in Embodiment 1 will be described. The structure of [Ir(mdbqz)₂(acac)] is shown below.

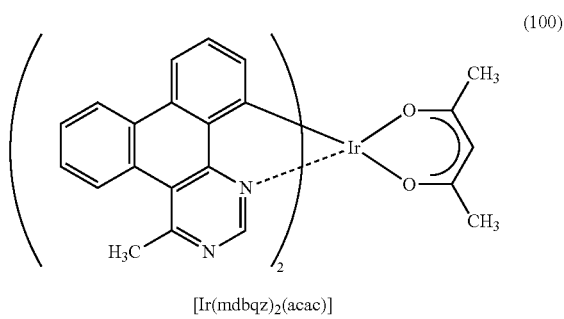

[Ir(mdbqz)₂(acac)]

Step 1; Synthesis of 5-(2-biphenyl)-4-methylpyrimidine

First, 2.9 g (16.8 mmol) of 5-bromo-4-methylpyrimidine, 3.6 g (18.0 mmol) of 2-biphenylboronic acid, 9.6 g (45.0 mmol) of tripotassium phosphate, 0.369 g (0.900 mmol) of 2-dicyclohexylphosphino-2',6'-dimethoxybiphenyl (S-Phos), and 40 mL of toluene were put in a 300-mL three-neck flask. Then, the air in the flask was replaced with nitrogen, and the mixture was degassed by being stirred with the pressure reduced. After that, the air in the flask was replaced with nitrogen, and 0.101 g (0.450 mmol) of palladium(II) acetate was added to the mixture. The mixture was stirred at 100° C. for 13 hours under a nitrogen stream. Water was added to the obtained reaction solution to separate the solution into an organic layer and an aqueous layer, and the aqueous layer was subjected to extraction with chloroform. The organic layer and the extracted solution were combined, washed with saturated saline, and dried by adding anhydrous magnesium sulfate. The obtained mixture was subjected to gravity filtration, and the filtrate was concentrated to give a solid. The solid was purified by silica gel column chromatography. As a developing solvent, a mixed solvent of hexane and ethyl acetate in a ratio of 4:1 was used. The obtained fraction of a target substance was concentrated to give 4.1 g of a white solid in a yield of 98%. By a nuclear magnetic resonance (NMR) method, the white solid was identified as 5-(2-biphenyl)-4-methylpyrimidine. The synthesis scheme of Step 1 is shown in (a-0).

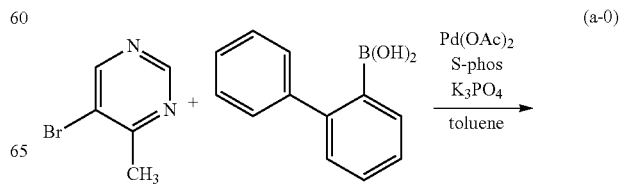

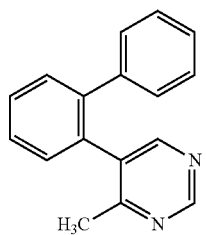

Step 2; Synthesis of 4-methyldibenzo[f,h]quinazoline (Abbreviation: Hmdbqz)

First, 4.1 g (16.4 mmol) of 5-(2-biphenyl)-4-methylpyrimidine that was synthesized in Step 1 was put in a 100-mL three-neck flask and degassed by being stirred with the pressure reduced. Then, the air in the flask was replaced with nitrogen. To this solid, 40 mL of dehydrated dichloromethane and 1.2 g (12.3 mmol) of concentrated sulfuric acid were added. Then, 10.6 g (65.6 mmol) of iron(III) chloride was added to this mixed solution, and the solution was stirred at room temperature for 20 hours. After that, the obtained mixed solution was added to methanol, and the mixture was stirred at room temperature for 16 hours. Water and dichloromethane were added to this reaction solution to separate the solution into an organic layer and an aqueous layer, and the aqueous layer was subjected to extraction with dichloromethane. The extracted solution and the organic layer were combined, washed with water and saturated saline, and then dried by adding anhydrous magnesium sulfate. The obtained mixture was subjected to gravity filtration, and the filtrate was concentrated to give a solid. To the solid, 1 L of methanol was added. Then, the mixture was heated for reflux for 1 hour and subjected to gravity filtration to remove an insoluble matter. The obtained filtrate was concentrated to give a solid. The solid was recrystallized with methanol to give 2.2 g of a white solid in a yield of 54%. By a nuclear magnetic resonance (NMR) method, the white solid was identified as 4-methyldibenzo[f,h]quinazoline. The synthesis scheme of Step 2 is shown in (b-0).

(b-0)

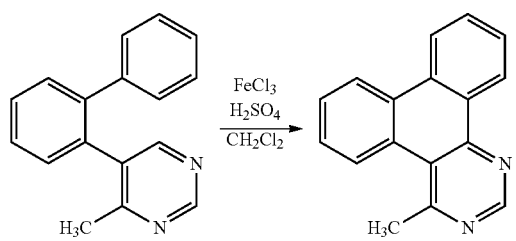

Step 3; Synthesis of di-μ-chloro-tetrakis(4-methyldibenzo[f,h]quinazolin-12-yl-κC,κN)diiridium(III) (Abbreviation: [Ir(mdbqz)$_2$Cl]$_2$)

First, 2.2 g (8.9 mmol) of 4-methyldibenzo[f,h]quinazoline (abbreviation: Hmdbqz) that was synthesized in Step 2, 0.266 g (0.89 mmol) of iridium chloride hydrate, and 40 mL of ethylene glycol were put in a 100-mL round-bottom flask, and the air in the flask was replaced with argon. This reaction container was subjected to irradiation with microwaves (2.45 GHz, 100 W) for 1 hour to cause a reaction. After the reaction, the reaction solution was subjected to suction filtration. The obtained solid was washed with methanol, water, and dichloromethane to give 0.37 g of an yellow solid in a yield of 58%. The synthesis scheme of Step 3 is shown in (c-0).

(c-0)

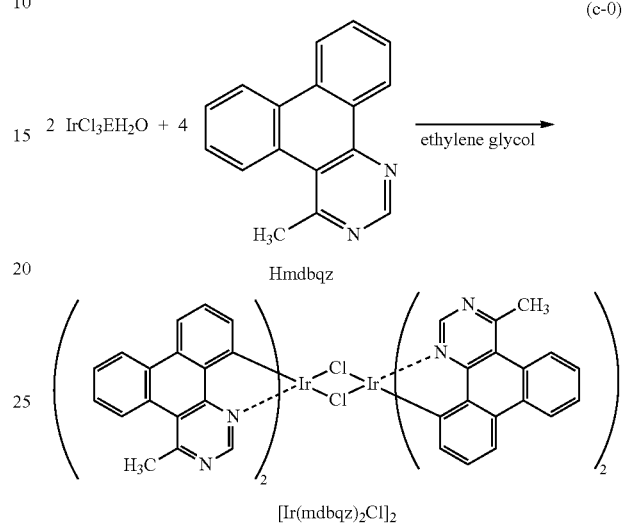

Step 4; Synthesis of bis(4-methyldibenzo[f,h]quinazolin-12-yl-κC,κN)(2,4-pentanedionato-κ$^2$O,O')iridium(III) (Abbreviation: [Ir(mdbqz)$_2$(acac)])

First, 15 mL of 2-ethoxyethanol, 0.370 g (0.26 mmol) of [ft(mdbqz)$_2$Cl]$_2$ that was synthesized in Step 3, 0.260 g (2.6 mmol) of acetylacetone, and 0.276 g (2.6 mmol) of sodium carbonate were put in a 50-mL recovery flask, and the air in the flask was replaced with argon. This reaction container was subjected to irradiation with microwaves (2.45 GHz, 120 W) for 2 hours to cause a reaction. After the reaction, water was added to the obtained reaction mixture, and the mixture was subjected to extraction with dichloromethane. The extracted solution was washed with saturated saline and then dried by adding anhydrous magnesium sulfate. The obtained mixture was subjected to gravity filtration to obtain a filtrate. This filtrate was concentrated to give a solid. The solid was recrystallized with a mixed solvent of dichloromethane and ethanol to give 160 mg of an yellow solid in a yield of 40%. The synthesis scheme of Step 4 is shown in (d-0).

(d-0)

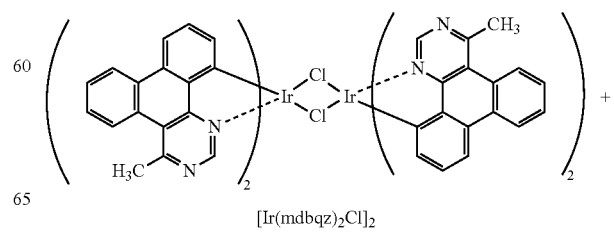

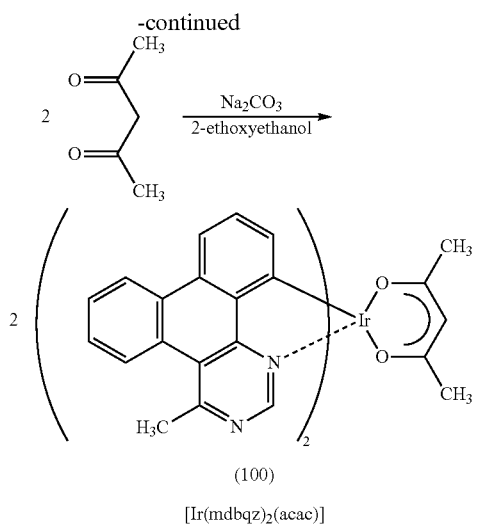

[Ir(mdbqz)₂(acac)]

Figure 15:
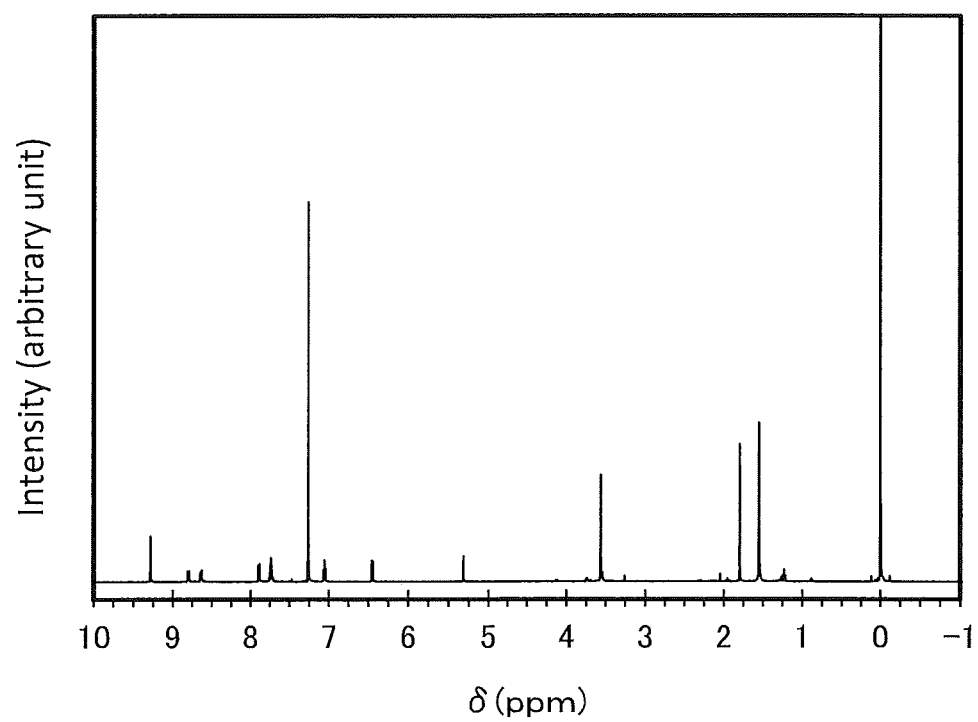
FIG. 15 is a $^1$H-NMR chart of the organometallic complex represented by Structural Formula (100).

Measurements were performed on the protons ($^1$H) of the yellow solid that was obtained in Step 4 by a nuclear magnetic resonance (NMR) method. The obtained values are shown below. In addition, FIG. 15 shows a $^1$H-NMR chart. The results revealed that [Ir(mdbqz)₂(acac)], which is the organometallic complex of one embodiment of the present invention and represented by Structural Formula (100), was obtained in Synthesis Example 1.

$^1$H-NMR. δ(CDCl₃): 1.80 (s, 6H), 3.56 (s, 6H), 5.31 (s, 1H), 6.45 (d, 2H), 7.06 (t, 2H), 7.71-7.76 (m, 4H), 7.89 (d, 2H), 8.64 (d, 2H), 8.80 (d, 2H), 9.28 (s, 2H).

Figure 16:
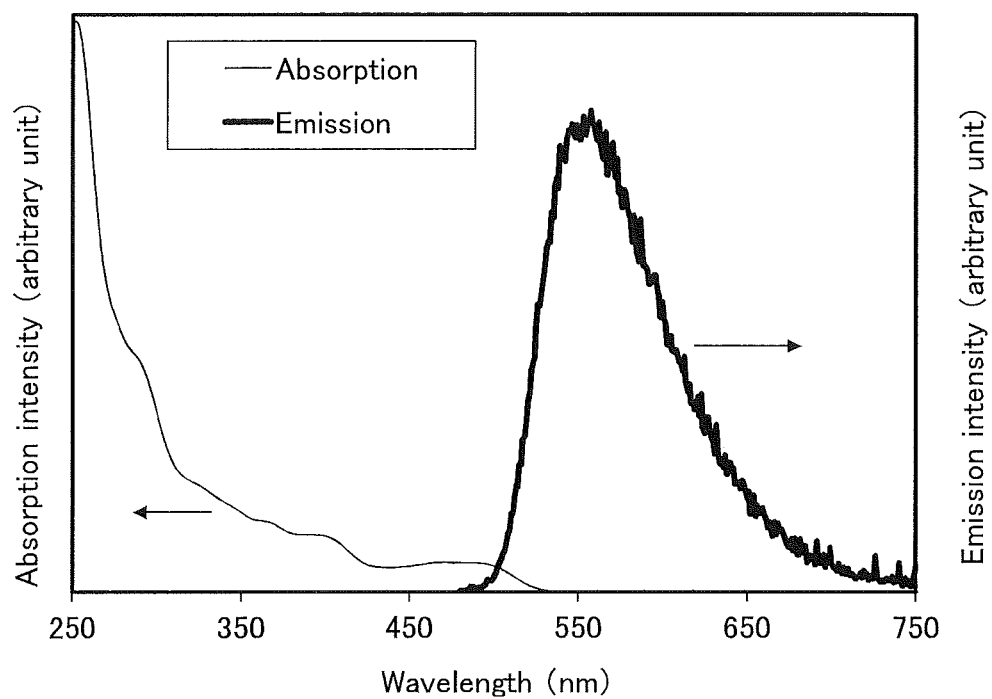
FIG. 16 is a graph showing the ultraviolet-visible absorption spectrum and the emission spectrum of the organometallic complex represented by Structural Formula (100).

Next, the ultraviolet-visible absorption spectrum (hereinafter, simply referred to as the absorption spectrum) and the emission spectrum of a dichloromethane solution of [Ir(mdbqz)₂(acac)] were measured. The measurement of the absorption spectrum was performed at room temperature in such a manner that an ultraviolet-visible light spectrophotometer (V550 type manufactured by JASCO Corporation) was used and the dichloromethane solution (0.010 mmol/L) was put in a quartz cell. In addition, the measurement of the emission spectrum was performed at room temperature in such a manner that a fluorescence spectrophotometer (FS920 manufactured by Hamamatsu Photonics K. K.) was used and the degassed dichloromethane solution (0.010 mmol/L) was put in a quartz cell. FIG. 16 shows the measurement results of the absorption spectrum and the emission spectrum. The horizontal axis represents a wavelength, and the vertical axes represent the absorption intensity and the emission intensity. FIG. 16 shows the absorption spectrum obtained in such a manner that the measured absorption spectrum of only dichloromethane that was in a quartz cell was subtracted from the measured absorption spectrum of the dichloromethane solution (0.010 mmol/L) that was in a quartz cell.

As shown in FIG. 16, the organometallic complex [Ir(mdbqz)₂(acac)] described in this example has an emission peak at 557 nm, which indicates that yellow green light was observed from the dichloromethane solution.

Next, [Ir(mdbqz)₂(acac)] obtained in this example was subjected to liquid chromatography mass spectrometry (LC/MS analysis).

In the LC/MS analysis, liquid chromatography (LC) was carried out with ACQUITY UPLC (registered trademark) (manufactured by Waters Corporation), and mass spectrometry (MS) was carried out with Xevo G2 Tof MS (manufactured by Waters Corporation). ACQUITY UPLC (registered trademark) BEH C₈ (2.1×100 mm, 1.7 μm) (manufactured by Waters Corporation) was used as a column for LC, and the column temperature was set to 40° C. Acetonitrile was used for Mobile Phase A, and a 0.1% formic acid aqueous solution was used for Mobile Phase B. A sample was prepared in such a manner that [Ir(mdbqz)₂(acac)] was dissolved in chloroform at a given concentration and the mixture was diluted with acetonitrile. The injection amount was 5.0 μL.

In LC, a gradient method in which the composition of mobile phases is changed was employed. The ratio of Mobile Phase A to Mobile Phase B was 40:60 for 0 to 1 minute after the start of the measurement, and then the composition was changed such that the ratio of Mobile Phase A to Mobile Phase B after 10 minutes was 95:5. The ratio was changed linearly.

In MS, ionization was carried out by an electrospray ionization (ESI) method. At this time, the capillary voltage and the sample cone voltage were set to 3.0 kV and 30 V, respectively, and detection was performed in a positive mode. A component with m/z of 779.20 which underwent the ionization under the above-described conditions was collided with an argon gas in a collision cell and dissociated into product ions. Energy (collision energy) for the collision with argon was 30 eV. A mass range for the measurement was m/z=100 to 1200. The detection results of the dissociated product ions obtained by time-of-flight (TOF) MS are shown in FIG. 17.

Figure 17:
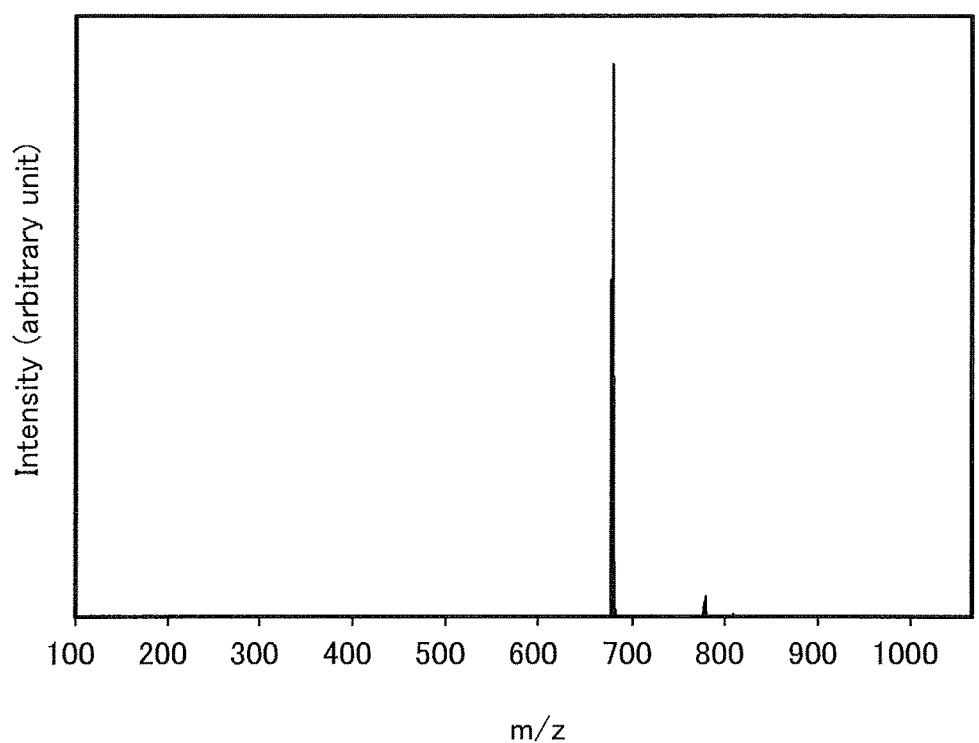
FIG. 17 shows LC/MS analysis results of the organometallic complex represented by Structural Formula (100).

The results in FIG. 17 show that product ions of [Ir(mdbqz)₂(acac)] are mainly detected at m/z of about 679. Note that the results in FIG. 17 show the characteristics derived from [Ir(mdbqz)₂(acac)] and therefore can be regarded as important data for identifying [Ir(mdbqz)₂(acac)] contained in the mixture.

The product ions detected at m/z of about 679 are presumed to be cations in [Ir(mdbqz)₂(acac)] from which acetylacetone is dissociated, which suggests that [Ir(mdbqz)₂(acac)] contains acetylacetone.

Example 2

Synthesis Example 2

In this example, a method for synthesizing bis(4-methyldibenzo[f,h]quinazolin-12-yl-κC,κN)(2,2,6,6-tetramethyl-3,5-heptanedionato-κ²O,O')iridium(III) (Abbreviation: [Ir(mdbqz)₂(dpm)]) represented by Structural Formula (101) in Embodiment 1 will be described. The structure of [Ir(mdbqz)₂(dpm)] is shown below.

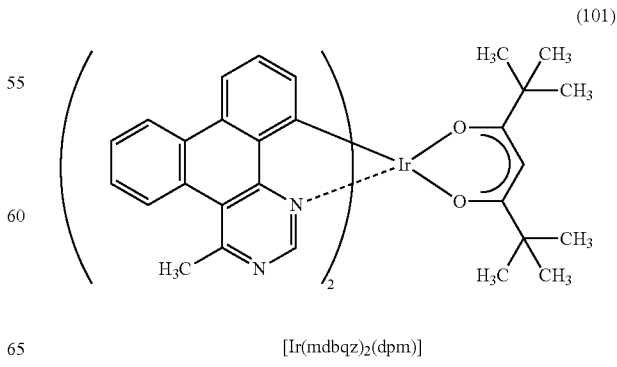

[Ir(mdbqz)₂(dpm)]

Step 1; Synthesis of di-μ-chloro-tetrakis(4-methyl-dibenzo[f,h]quinazolin-12-yl-κC,κN)diiridium(III) (Abbreviation: [Ir(mdbqz)$_2$Cl]$_2$)

First, 2.0 g (8.2 mmol) of 4-methyldibenzo[f,h]quinazoline (abbreviation: Hmdbqz), 1.2 g (4.0 mmol) of iridium chloride hydrate, 30 mL of 2-ethoxyethanol, and 10 mL of water were put in a 100-mL round-bottom flask, and the air in the flask was replaced with argon. This reaction container was subjected to irradiation with microwaves (2.45 GHz, 100 W) for 2 hours to cause a reaction. After the reaction, the reaction solution was subjected to suction filtration. The obtained solid was washed with methanol to give 2.5 g of a brown solid in a yield of 86%. The synthesis scheme of Step 1 is shown in (c-1).

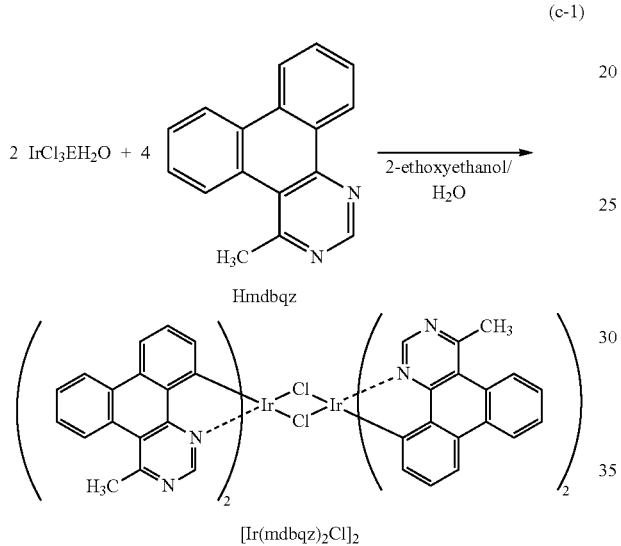

(c-1)

Step 2; Synthesis of bis(4-methyldibenzo[f,h]quinazolin-12-yl-κC,κN)(2,2,6,6-tetramethyl-3,5-heptanedionato-κ$^2$O,O')iridium(III) (Abbreviation: [ft(mdbqz)$_2$(dpm)])

First, 40 mL of 2-ethoxyethanol, 2.5 g (1.7 mmol) of [ft(mdbqz)$_2$Cl]$_2$ that was synthesized in Step 1, 3.1 g (17 mmol) of dipivaloylmethane, and 1.8 g (17 mmol) of sodium carbonate were put in a 100-mL round-bottom flask, and the air in the flask was replaced with argon. This reaction container was subjected to irradiation with microwaves (2.45 GHz, 120 W) for 2 hours to cause a reaction. After the reaction, water was added to the obtained reaction mixture, and the mixture was subjected to extraction with dichloromethane. The extracted solution was washed with saturated saline and then dried by adding anhydrous magnesium sulfate. The obtained mixture was subjected to gravity filtration to obtain a filtrate. This filtrate was concentrated to give a solid. Dichloromethane was added to the solid, and the mixture was subjected to suction filtration through a stack of Celite (produced by Wako Pure Chemical Industries, Ltd., Catalog No. 531-16855) and aluminum oxide (alumina). The obtained filtrate was concentrated to give a solid. The solid was recrystallized with a mixed solvent of dichloromethane and ethanol to give 190 mg of an yellow solid in a yield of 6%. The synthesis scheme of Step 2 is shown in (d-2).

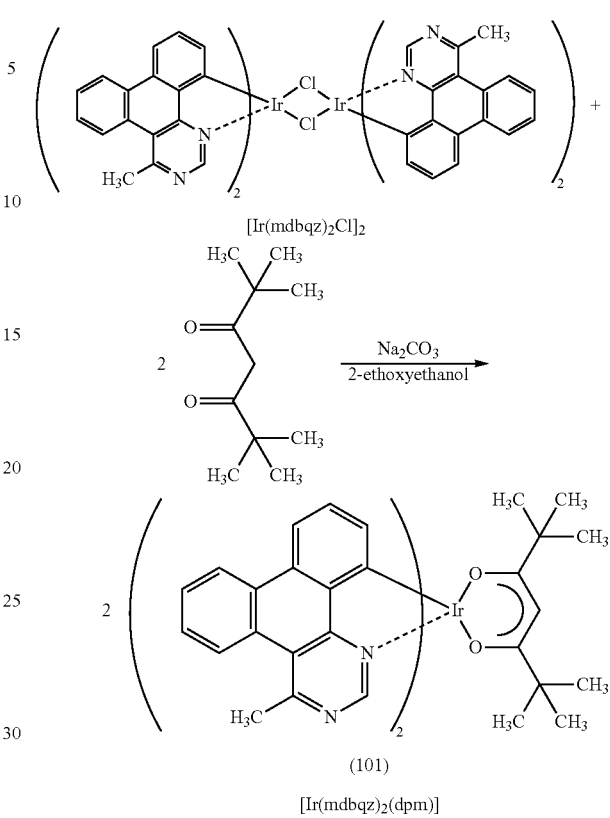

(d-2)

Figure 18:
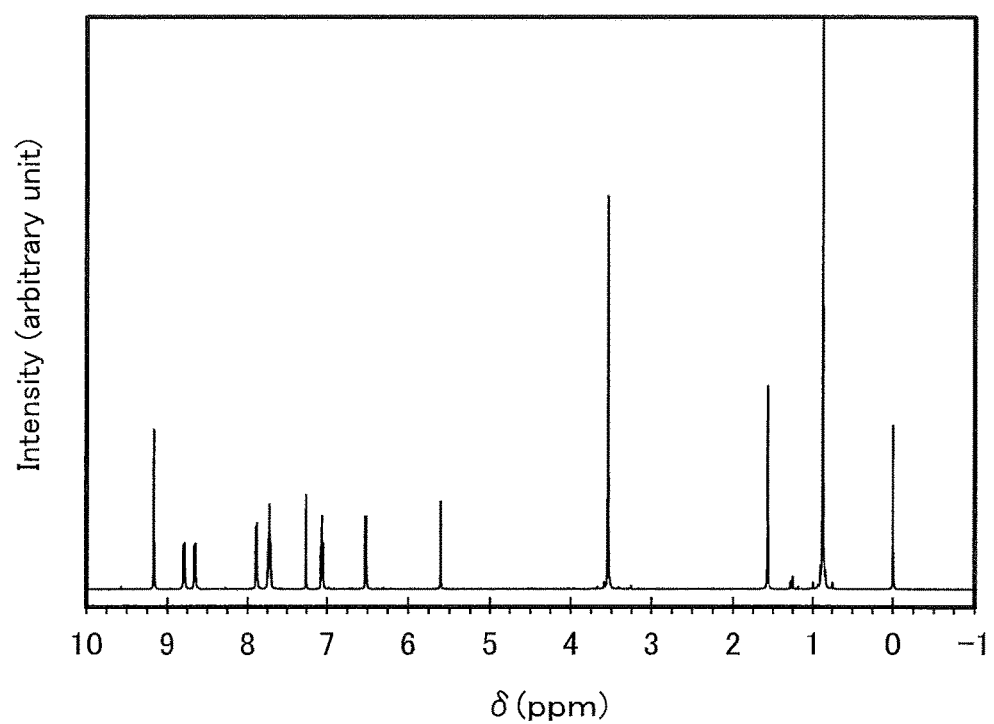
FIG. 18 is a $^1$H NMR chart of the organometallic complex represented by Structural Formula (101).

Measurements were performed on the protons ($^1$H) of the yellow solid that was obtained in Step 2 by a nuclear magnetic resonance (NMR) method. The obtained values are shown below. In addition, FIG. 18 shows a $^1$H-NMR chart. The results revealed that [ft(mdbqz)$_2$(dpm)], which is the organometallic complex of one embodiment of the present invention and represented by Structural Formula (101), was obtained in Synthesis Example 2.

$^1$H-NMR. δ(CDCl$_3$): 0.87 (s, 18H), 3.54 (s, 6H), 5.61 (s, 1H), 6.52 (d, 2H), 7.06 (t, 2H), 7.70-7.75 (m, 4H), 7.89 (d, 2H), 8.64 (d, 2H), 8.79 (d, 2H), 9.17 (s, 2H).

Figure 19:
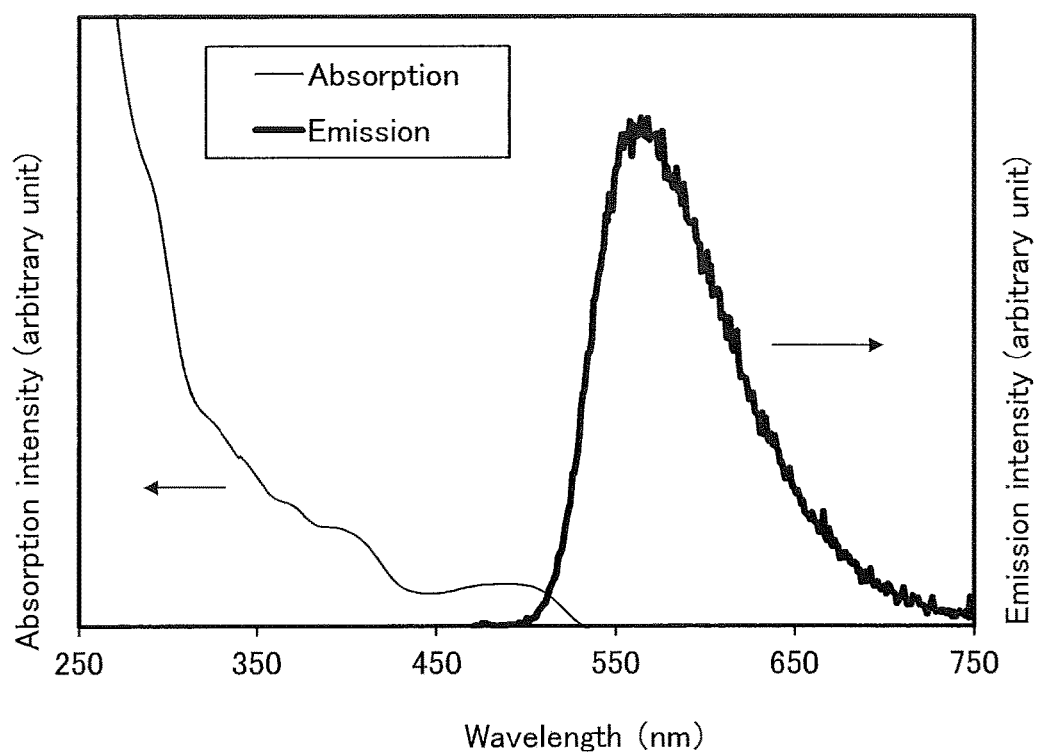
FIG. 19 shows the ultraviolet-visible absorption spectrum and the emission spectrum of the organometallic complex represented by Structural Formula (101).

Next, the ultraviolet-visible absorption spectrum (hereinafter, simply referred to as the absorption spectrum) and the emission spectrum of a dichloromethane solution of [ft(mdbqz)$_2$(dpm)] were measured. The measurement of the absorption spectrum was performed at room temperature in such a manner that an ultraviolet-visible light spectrophotometer (V550 type manufactured by JASCO Corporation) was used and the dichloromethane solution (0.0096 mmol/L) was put in a quartz cell. In addition, the measurement of the emission spectrum was performed at room temperature in such a manner that a fluorescence spectrophotometer (FS920 manufactured by Hamamatsu Photonics K. K.) was used and the degassed dichloromethane solution (0.0096 mmol/L) was put in a quartz cell. FIG. 19 shows the measurement results of the absorption spectrum and the emission spectrum. The horizontal axis represents a wavelength, and the vertical axes represent the absorption intensity and the emission intensity. FIG. 19 shows the absorption spectrum obtained in such a manner that the measured absorption spectrum of only dichloromethane that was in a quartz cell was subtracted from the measured absorption spectrum of the dichloromethane solution (0.0096 mmol/L) that was in a quartz cell.

As shown in FIG. 19, the organometallic complex [Ir(mdbqz)$_2$(dpm)] described in this example has an emission peak at 557 nm, which indicates that yellow green light was observed from the dichloromethane solution.

Next, [Ir(mdbqz)$_2$(dpm)] obtained in this example was subjected to liquid chromatography mass spectrometry (LC/MS analysis).

In the LC/MS analysis, liquid chromatography (LC) was carried out with ACQUITY UPLC (registered trademark) (manufactured by Waters Corporation), and mass spectrometry (MS) was carried out with Xevo G2 Tof MS (manufactured by Waters Corporation). ACQUITY UPLC (registered trademark) BEH C$_8$ (2.1×100 mm, 1.7 μm) (manufactured by Waters Corporation) was used as a column for LC, and the column temperature was set to 40° C. Acetonitrile was used for Mobile Phase A, and a 0.1% formic acid aqueous solution was used for Mobile Phase B. A sample was prepared in such a manner that [Ir(mdbqz)$_2$(dpm)] was dissolved in chloroform at a given concentration and the mixture was diluted with acetonitrile. The injection amount was 5.0 μL.

In LC, a gradient method in which the composition of mobile phases is changed was employed. The ratio of Mobile Phase A to Mobile Phase B was 70:30 for 0 to 1 minute after the start of the measurement, and then the composition was changed such that the ratio of Mobile Phase A to Mobile Phase B after 10 minutes was 95:5. The ratio was changed linearly.

In MS, ionization was carried out by an electrospray ionization (ESI) method. At this time, the capillary voltage and the sample cone voltage were set to 3.0 kV and 30 V, respectively, and detection was performed in a positive mode. A component with m/z of 863.29 which underwent the ionization under the above-described conditions was collided with an argon gas in a collision cell and dissociated into product ions. Energy (collision energy) for the collision with argon was 30 eV. A mass range for the measurement was m/z=100 to 1200. The detection results of the dissociated product ions obtained by time-of-flight (TOF) MS are shown in FIG. 20.

Figure 20:
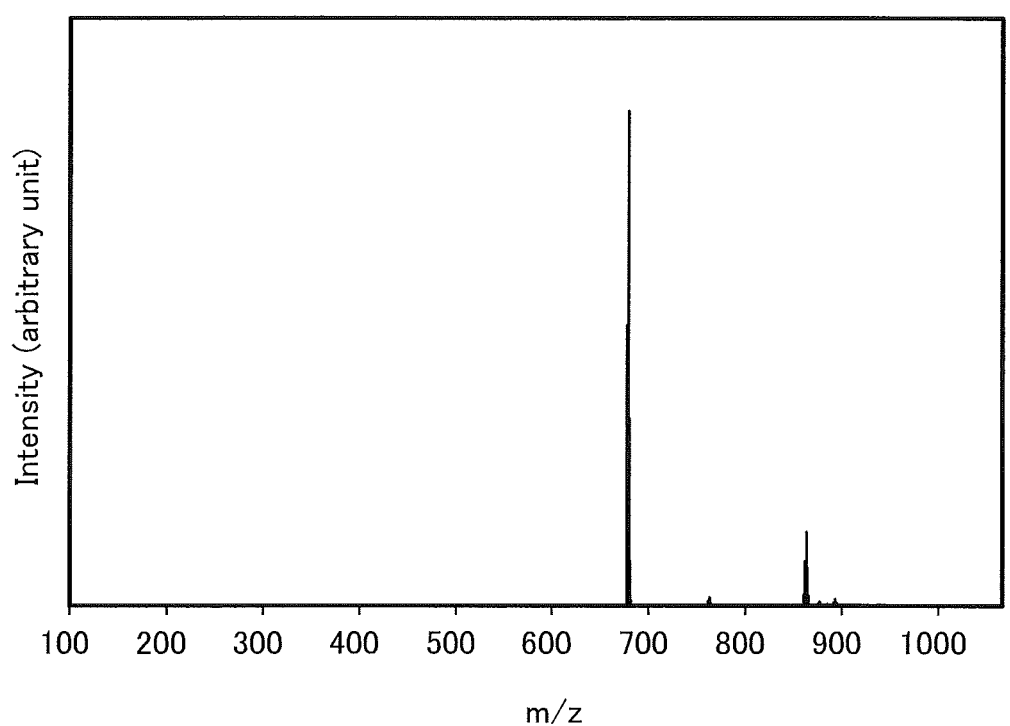
FIG. 20 shows LC/MS analysis results of the organometallic complex represented by Structural Formula (101).

The results in FIG. 20 show that product ions of [Ir(mdbqz)$_2$(dpm)] are mainly detected at m/z of about 679. Note that the results in FIG. 20 show the characteristics derived from [Ir(mdbqz)$_2$(dpm)] and therefore can be regarded as important data for identifying [Ir(mdbqz)$_2$(dpm)] contained in the mixture.

The product ions detected at m/z of about 679 are presumed to be cations in [Ir(mdbqz)$_2$(dpm)] from which dipivaloylmethane is dissociated, which suggests that [Ir(mdbqz)$_2$(dpm)] contains dipivaloylmethane.

Example 3

Synthesis Example 3

In this example, a method for synthesizing bis(4-methyldibenzo[f,h]quinazolin-12-yl-κC,κN)(2,8-dimethyl-4,6-nonanedionato-κ$^2$O,O')iridium(III) (Abbreviation: [Ir(mdbqz)$_2$(divm)]) represented by Structural Formula (104) in Embodiment 1 will be described. The structure of [Ir(mdbqz)$_2$(divm)] is shown below.

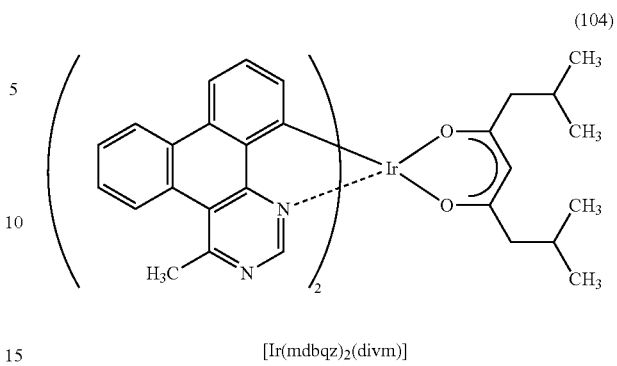

(104)

[Ir(mdbqz)$_2$(divm)]

Synthesis of bis(4-methyldibenzo[f,h]quinazolin-12-yl-κC,κN)(2,8-dimethyl-4,6-nonanedionato-κ$^2$O,O') iridium(III) (Abbreviation: [Ir(mdbqz)$_2$(divm)])

First, 40 mL of 2-ethoxyethanol, 2.1 g (1.5 mmol) of [Ir(mdbqz)$_2$Cl]$_2$, 1.7 g (9.2 mmol) of diisovalerylmethane, and 1.6 g (15 mmol) of sodium carbonate were put in a 100-mL round-bottom flask, and the air in the flask was replaced with argon. This reaction container was subjected to irradiation with microwaves (2.45 GHz, 120 W) for 1 hour to cause a reaction. After the reaction, dichloromethane was added to the reaction solution, and the solution was subjected to suction filtration to remove a solid, thereby obtaining a filtrate. The filtrate was concentrated to give a solid. The solid was purified by silica gel column chromatography. Dichloromethane was used as a developing solvent. The obtained fraction of a target substance was concentrated to give a solid. The solid was recrystallized with a mixed solvent of ethyl acetate and hexane to give 110 mg of an yellow solid in a yield of 9%. The synthesis scheme is shown in (d-1).

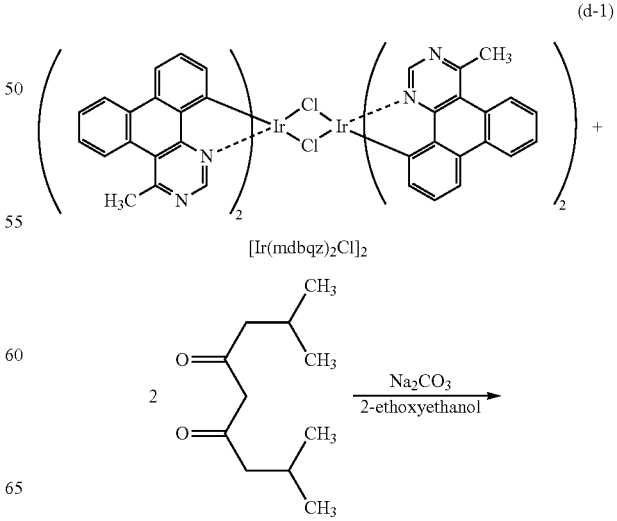

(d-1)

-continued

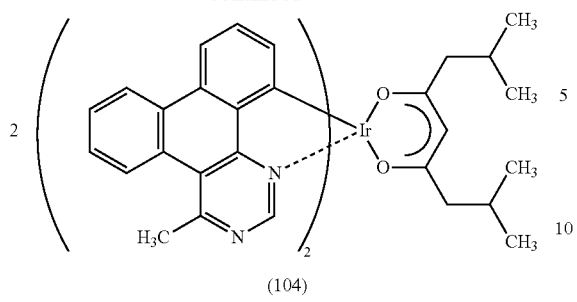

(104)

[Ir(mdbqz)₂(divm)]

Figure 21:
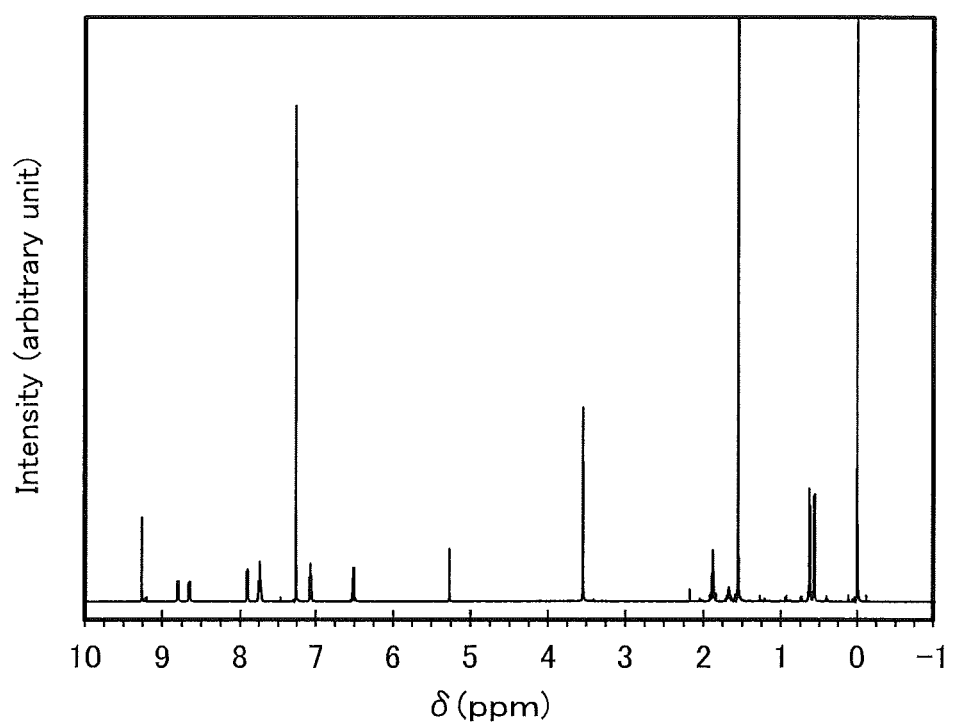
FIG. 21 is a $^1$H-NMR chart of the organometallic complex represented by Structural Formula (104).

Measurements were performed on the protons (¹H) of the yellow solid that was obtained in the above step by a nuclear magnetic resonance (NMR) method. The obtained values are shown below. In addition, FIG. 21 shows a ¹H-NMR chart. The results revealed that [ft(mdbqz)₂(divm)], which is the organometallic complex of one embodiment of the present invention and represented by Structural Formula (104), was obtained in Synthesis Example 3.

¹H-NMR. δ(CDCl₃): 0.57 (d, 6H), 0.63 (d, 6H), 1.63-1.71 (m, 2H), 1.84-1.92 (m, 4H), 3.54 (s, 6H), 5.27 (s, 1H), 6.51 (d, 2H), 7.07 (t, 2H), 7.72-7.77 (m, 4H), 7.91 (d, 2H), 8.65 (d, 2H), 8.80 (d, 2H), 9.27 (s, 2H).

Figure 22:
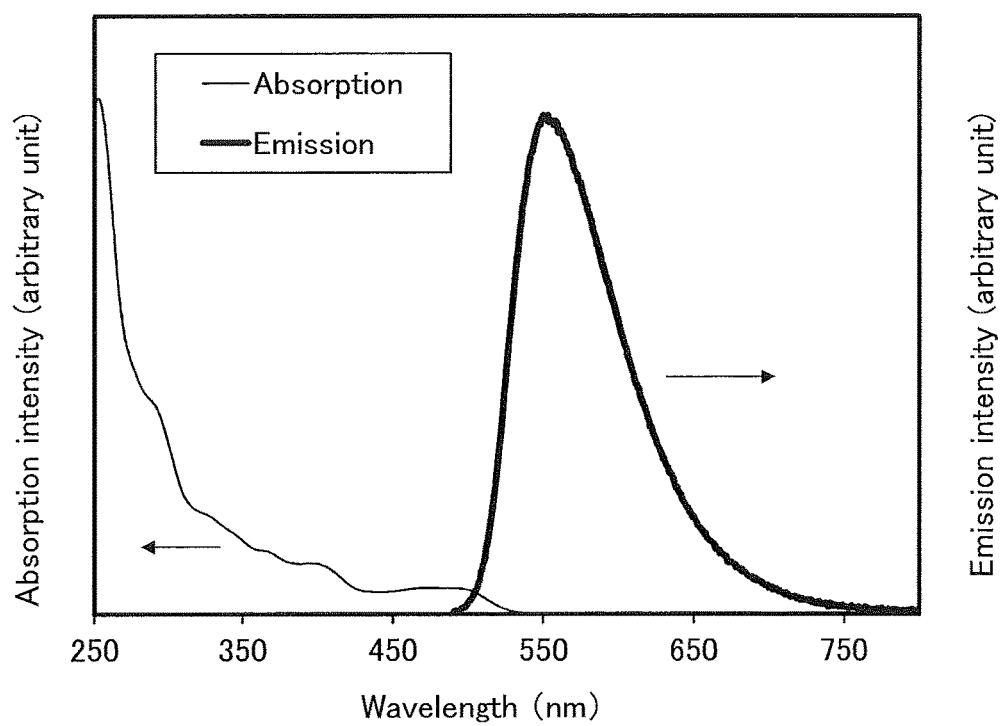
FIG. 22 shows the ultraviolet-visible absorption spectrum and the emission spectrum of the organometallic complex represented by Structural Formula (104).

Next, the ultraviolet-visible absorption spectrum (hereinafter, simply referred to as the absorption spectrum) and the emission spectrum of a dichloromethane solution of [ft (mdbqz)₂(divm)] were measured. The measurement of the absorption spectrum was performed at room temperature in such a manner that an ultraviolet-visible light spectrophotometer (V550 type manufactured by JASCO Corporation) was used and the dichloromethane solution (0.0099 mmol/L) was put in a quartz cell. In addition, the measurement of the emission spectrum was performed at room temperature in such a manner that an absolute PL quantum yield measurement system (C11347-01 manufactured by Hamamatsu Photonics K. K.) was used and the deoxidized dichloromethane solution (0.0099 mmol/L) was sealed in a quartz cell under a nitrogen atmosphere in a glove box (LABstar M13 (1250/780) manufactured by Bright Co., Ltd). FIG. 22 shows the measurement results of the absorption spectrum and the emission spectrum. The horizontal axis represents a wavelength, and the vertical axes represent the absorption intensity and the emission intensity. FIG. 22 shows the absorption spectrum obtained in such a manner that the measured absorption spectrum of only dichloromethane that was in a quartz cell was subtracted from the measured absorption spectrum of the dichloromethane solution (0.0099 mmol/L) that was in a quartz cell.

As shown in FIG. 22, the organometallic complex [Ir (mdbqz)₂(divm)] described in this example has an emission peak at 553 nm, which indicates that yellow green light was observed from the dichloromethane solution.

Example 4

Synthesis Example 4

In this example, a method for synthesizing tris(4-methyldibenzo[f,h]quinazolin-12-yl-κC,κN)iridium(III) (Abbreviation: [Ir(mdbqz)₃]) represented by Structural Formula (114) in Embodiment 1 will be described. The structure of [Ir(mdbqz)₃] is shown below.

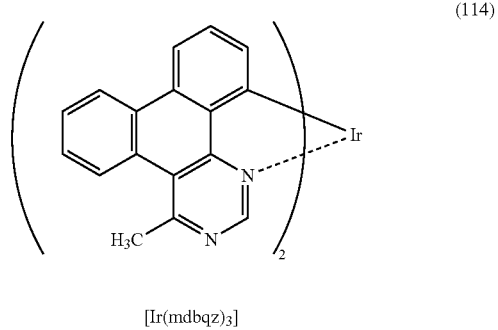

(114)

[Ir(mdbqz)₃]

Synthesis of tris(4-methyldibenzo[f,h]quinazolin-12-yl-κC,κN)iridium(III) (Abbreviation: [Ir(mdbqz)₃])

First, 1.1 g (4.5 mmol) of 4-methyldibenzo[f,h]quinazoline (abbreviation: Hmdbqz) and 0.44 g (0.90 mmol) of tris(acetylacetonato)iridium(III) were put in a reaction container provided with a three-way cock, and the mixture was heated at 250° C. for 42 hours under an argon stream. Dichloromethane was added to the obtained reaction mixture, and the mixture was subjected to suction filtration to give a solid. Then, 200 mL of toluene was added to the solid, and the mixture was heated for reflux for 30 minutes. This mixture was filtered to give a solid. To the solid, 100 mL of 1,1,2,2-tetrachloroethane was added, and the mixture was heated at 140° C. for 30 minutes. This mixture was filtered to give 0.39 g of an orange solid in a yield of 47%. The synthesis scheme is shown in (c-2).

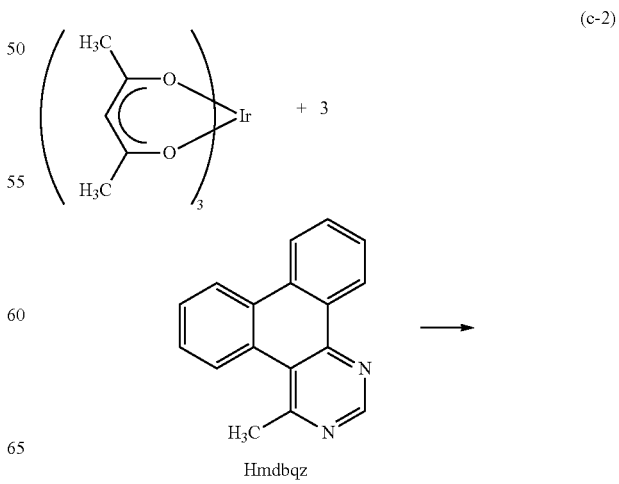

(c-2)

Hmdbqz

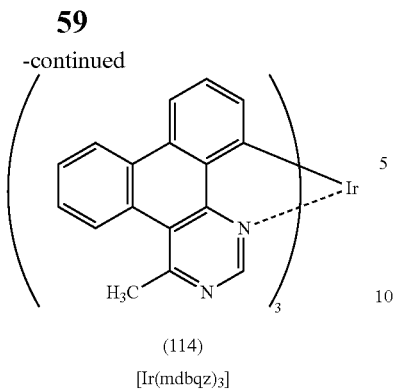

(114)

[Ir(mdbqz)₃]

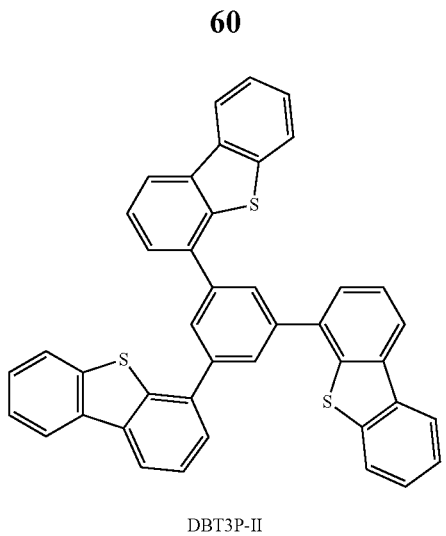

DBT3P-II

Figure 23:
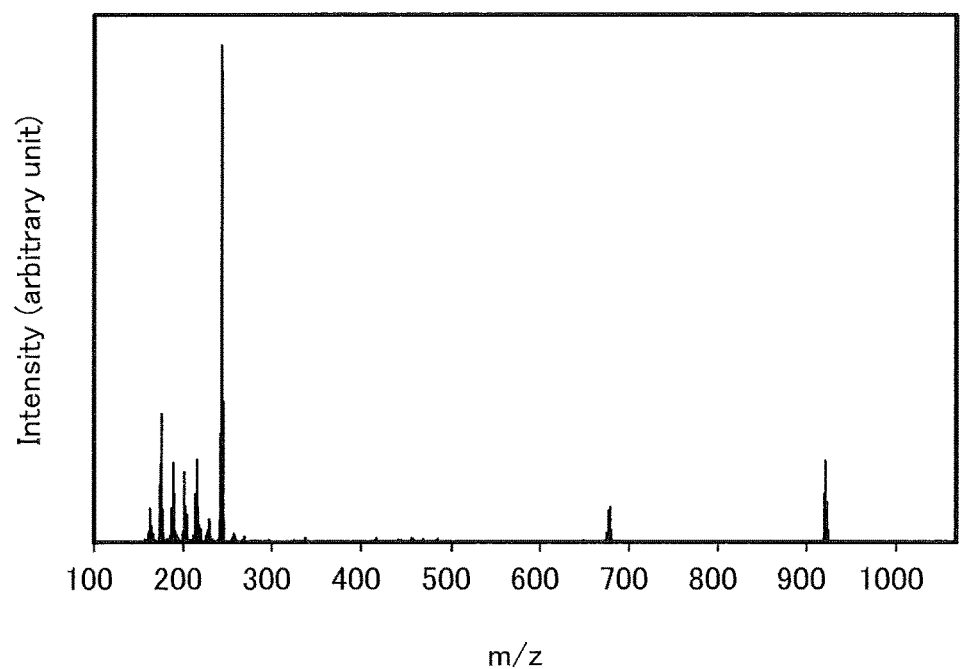
FIG. 23 shows EI/MS analysis results of the organometallic complex represented by Structural Formula (114).

The orange solid obtained in the above step was subjected to electron impact mass spectrometry (EI/MS analysis). Accelerated electrons with an energy of 70 eV were used for the ionization. FIG. 23 shows the mass spectrum. In FIG. 23, the horizontal axis represents m/z (mass-to-charge ratio) and the vertical axis represents the intensity (arbitrary unit). In the spectrum shown in FIG. 23, the peak at m/z of about 922 is derived from molecular ions. The peak at m/z of about 243, which suggests the fragment derived from the ligand, 4-methyldibenzo[f,h]quinazoline (abbreviation: Hmdbqz), serves as a reference, and the peak derived from molecular ions (m/z of about 922) is not strong; this result indicates that the fragmentation occurs with high probability. A fragment indicated by the peak at m/z of about 679 is generated in such a manner that two bonds are cut from a molecular ion at the same time and one ligand, 4-methyldibenzo[f,h]quinazoline (abbreviation: Hmdbqz), is removed from [Ir(mdbqz)₃]. It is found that the ligand, 4-methyldibenzo[f,h]quinazoline (abbreviation: Hmdbqz), is further fragmented, thereby generating fragments. The results revealed that [Ir(mdbqz)₃], which is the organometallic complex of one embodiment of the present invention and represented by Structural Formula (114), was obtained in Synthesis Example 4.

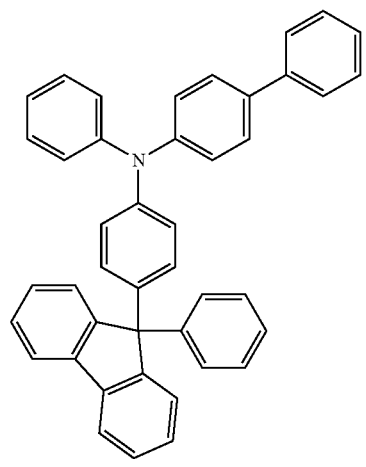

BPAFLP

Example 5

Figure 24:
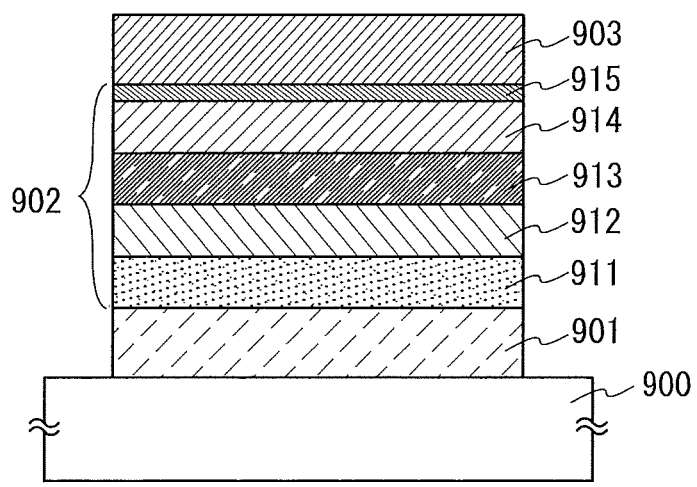
FIG. 24 illustrates a light-emitting element.

In this example, Light-emitting Element 1 was fabricated, in which the organometallic complex [Ir(mdbqz)₂(acac)] which is one embodiment of the present invention and represented by Structural Formula (100) is used for a light-emitting layer, and the operation characteristics of Light-emitting Element 1 were measured. In addition, the emission spectrum of Light-emitting Element 1 was measured. Note that the fabrication of Light-emitting Element 1 will be described with reference to FIG. 24. Chemical formulae of materials used in this example are shown below.

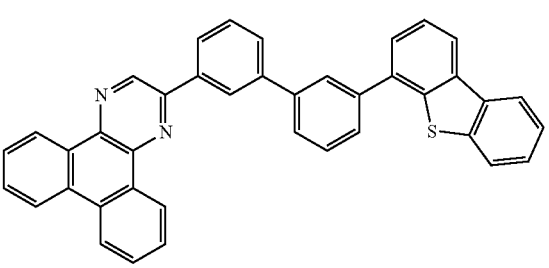

2mDBTBPDBq-II

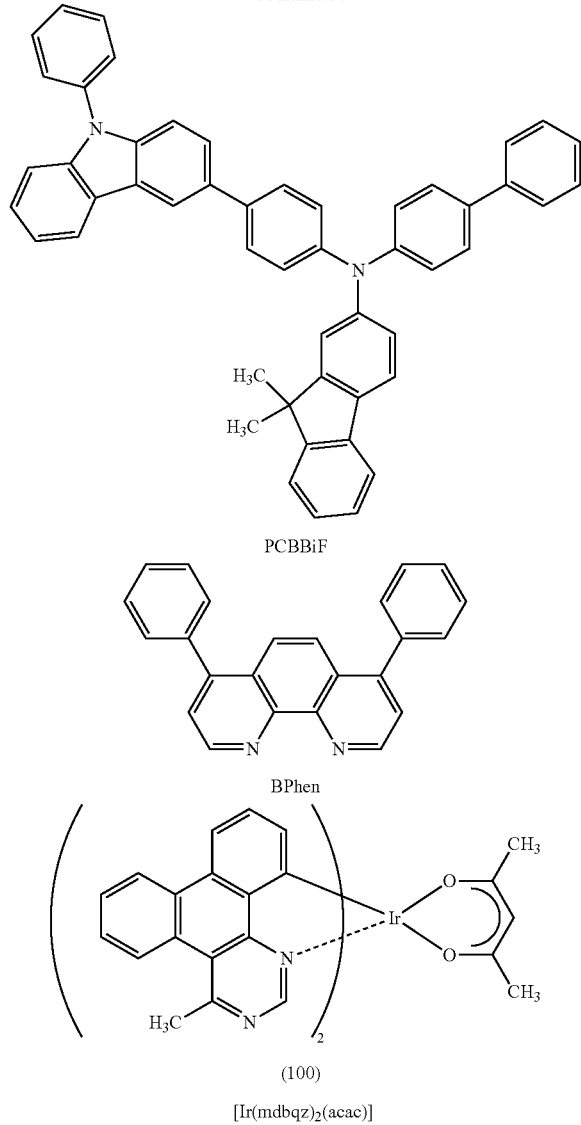

PCBBiF

BPhen

[Ir(mdbqz)₂(acac)]

<<Fabrication of Light-Emitting Element 1>>

First, indium tin oxide (ITO) was deposited over a glass substrate 900 by a sputtering method, so that a first electrode 901 which functions as an anode was formed. Note that the thickness of the first electrode 901 was set to 110 nm and that the area of the first electrode 901 was set to 2 mm×2 mm.

Next, as pretreatment for fabricating Light-emitting Element 1 over the substrate 900, a surface of the substrate was washed with water, baking was performed at 200° C. for 1 hour, and then UV ozone treatment was performed for 370 seconds.

After that, the substrate 900 was transferred into a vacuum evaporation apparatus in which the pressure had been reduced to approximately $10^{-4}$ Pa, subjected to vacuum baking at 170° C. for 30 minutes in a heating chamber of the vacuum evaporation apparatus, and then cooled down for approximately 30 minutes.

Next, the substrate 900 was fixed to a holder provided in the vacuum evaporation apparatus so that the surface of the substrate 900 over which the first electrode 901 was formed faced downward. In this example, the case will be described where a hole-injection layer 911, a hole-transport layer 912, a light-emitting layer 913, an electron-transport layer 914, and an electron-injection layer 915 which are included in an EL layer 902 are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2; in this manner, the hole-injection layer 911 was formed on the first electrode 901. The thickness of the hole-injection layer 911 was set to 20 nm. Note that co-evaporation is an evaporation method in which a plurality of different substances are concurrently vaporized from their respective evaporation sources.

Then, 4-phenyl-4'-(9-phenylfluoren-9-yl)triphenylamine (abbreviation: BPAFLP) was deposited by evaporation to a thickness of 20 nm, so that the hole-transport layer 912 was formed.

Next, the light-emitting layer 913 was formed on the hole-transport layer 912 in the following manner. By co-evaporation, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-9,9-dimethyl-N-[4-(9-phenyl-9H-carbazol-3-yl)phenyl]-9H-fluoren-2-amine (abbreviation: PCBBiF), and [Ir(mdbqz)₂(acac)] were deposited so that the mass ratio of 2mDBTBPDBq-II to PCBBiF and [Ir(mdbqz)₂(acac)] was 0.8:0.2:0.025. The thickness of the light-emitting layer 913 was set to 40 nm.

Next, the electron-transport layer 914 was formed in such a manner that 2mDBTBPDBq-II was deposited by evaporation on the light-emitting layer 913 to a thickness of 20 nm and then bathophenanthroline (abbreviation: BPhen) was deposited by evaporation to a thickness of 10 nm. Furthermore, lithium fluoride was deposited by evaporation to a thickness of 1 nm on the electron-transport layer 914, so that the electron-injection layer 915 was formed.

Finally, aluminum was deposited by evaporation to a thickness of 200 nm on the electron-injection layer 915 to form a second electrode 903 serving as a cathode. In this manner, Light-emitting Element 1 was fabricated. Note that in all of the above evaporation steps, evaporation was performed by a resistance-heating method.

Table 2 shows the element structure of Light-emitting Element 1 fabricated as described above.

TABLE 2

| | First Electrode | Hole-injection Layer | Hole-transport Layer | Light-emitting Layer | Electron-transport Layer | | Electron-injection Layer | Second Electrode |
|---|---|---|---|---|---|---|---|---|
| Light-emitting Element 1 | ITO (110 nm) | DBT3P-II:MoOx (4:2 20 nm) | BPAFLP (20 nm) | * | 2mDBTBPDBq-II (20 nm) | BPhen (10 nm) | LiF (1 nm) | Al (200 nm) |

* 2mDBTBPDBq-II:PCBBiF:[Ir(mdbqz)₂(acac)] (0.8:0.2:0.025 40 nm)

Light-emitting Element 1 was sealed in a glove box under a nitrogen atmosphere so as not to be exposed to the air (specifically, a sealant was applied to surround the element, and at the time of sealing, UV treatment was performed and heat treatment was performed at 80° C. for 1 hour).

<<Operation Characteristics of Light-Emitting Element 1>>

The operation characteristics of Light-emitting Element 1 were measured. Note that the measurements were performed at room temperature (in an atmosphere kept at 25° C.).

Figure 25:
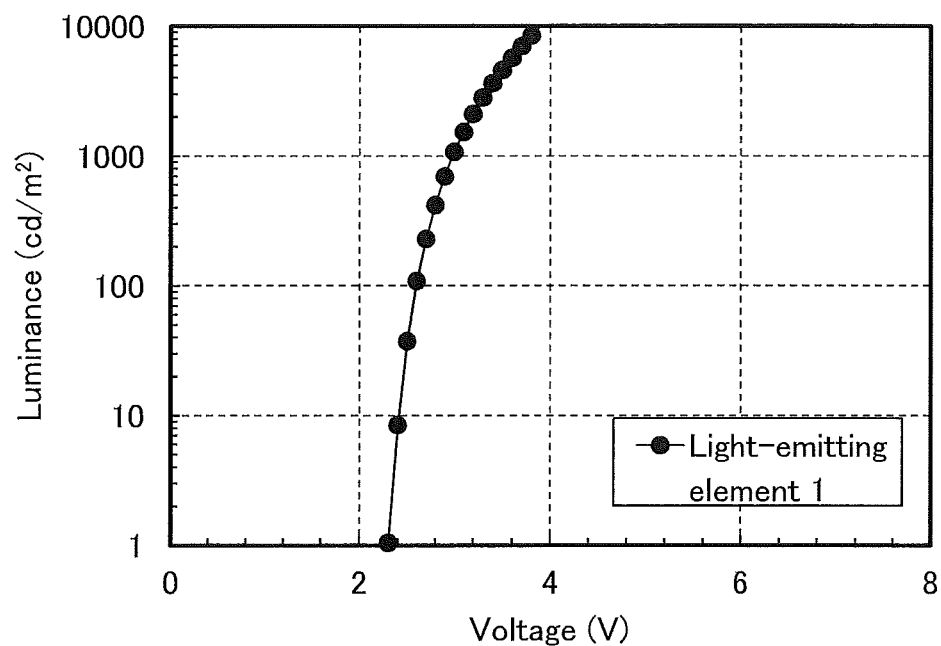
FIG. 25 is a graph showing the voltage-luminance characteristics of Light-emitting Element 1.
Figure 26:
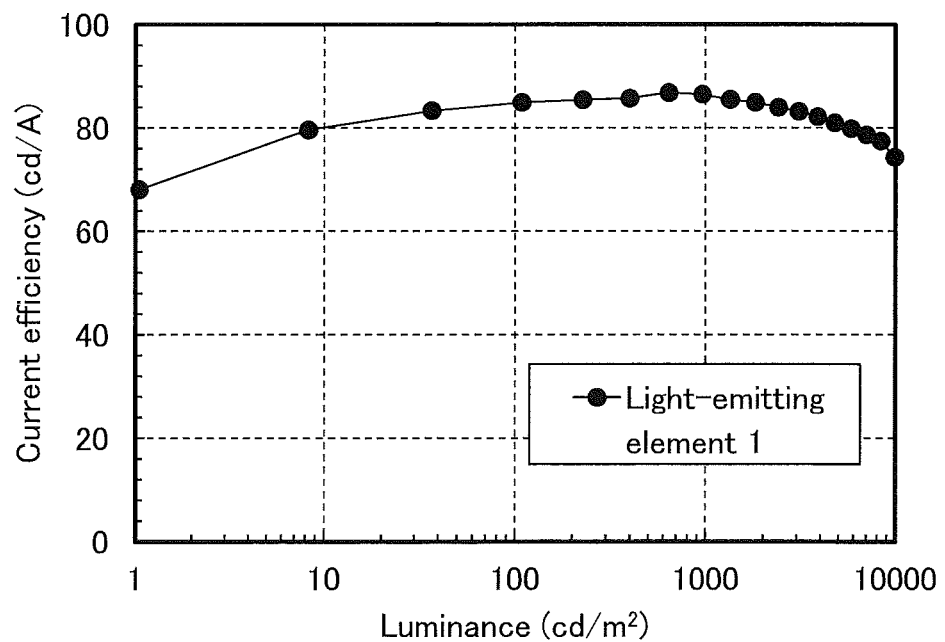
FIG. 26 is a graph showing the luminance-current efficiency characteristics of Light-emitting Element 1.

FIG. 25 shows the voltage-luminance characteristics of Light-emitting Element 1. FIG. 26 shows the luminance-current efficiency characteristics of Light-emitting Element 1.

These results reveal that Light-emitting Element 1 of one embodiment of the present invention has high efficiency. Table 3 shows initial values of main characteristics of Light-emitting Element 1 at a luminance of about 1000 cd/m².

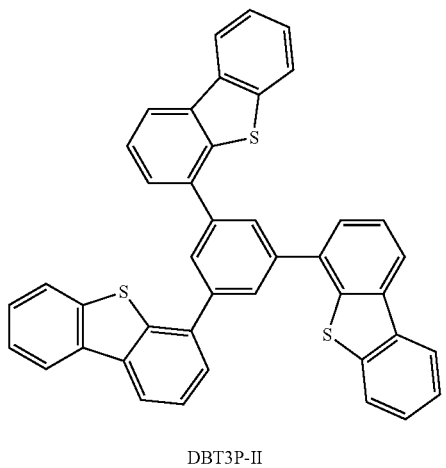

DBT3P-II

TABLE 3

| | Voltage (V) | Current (mA) | Current Density (mA/cm²) | Chromaticity (x, y) | Luminance (cd/m²) | Current Efficiency (cd/A) | Power Efficiency (lm/W) | External Quantum Efficiency (%) |
|---|---|---|---|---|---|---|---|---|
| Light-emitting Element 1 | 3.0 | 0.050 | 1.2 | (0.40, 0.58) | 1100 | 86 | 91 | 23 |

The above results reveal that Light-emitting Element 1 fabricated in this example is a high-luminance light-emitting element having high current efficiency.

Figure 27:
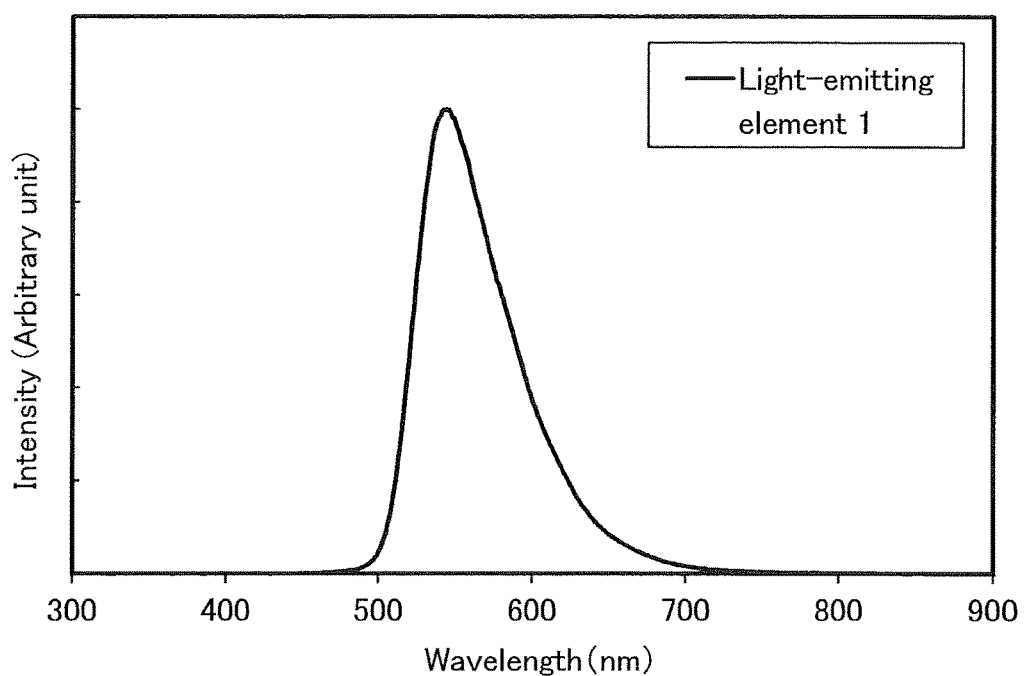
FIG. 27 is a graph showing the emission spectrum of Light-emitting Element 1.

FIG. 27 shows the emission spectrum of Light-emitting Element 1, through which a current flows at a current density of 2.5 mA/cm². As shown in FIG. 27, the emission spectrum of Light-emitting Element 1 has a peak at around 544 nm. It is suggested that the peak is derived from light emission of the organometallic complex [Ir(mdbqz)₂(acac)] of one embodiment of the present invention.

Example 6

In this example, Light-emitting Element 2 was fabricated, in which the organometallic complex [Ir(mdbqz)₂(dpm)] which is one embodiment of the present invention and represented by Structural Formula (101) is used for a light-emitting layer, and the operation characteristics of Light-emitting Element 2 were measured. In addition, the emission spectrum of Light-emitting Element 2 was measured. Note that Light-emitting Element 2 has the same structure as Light-emitting Element 1 described in Example 5 and will thus be described with reference to FIG. 24. Chemical formulae of materials used in this example are shown below.

-continued

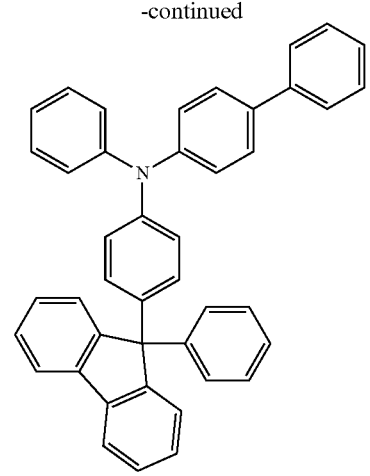

BPAFLP

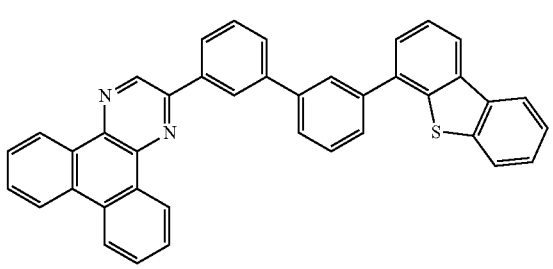

2mDBTBPDBq-II

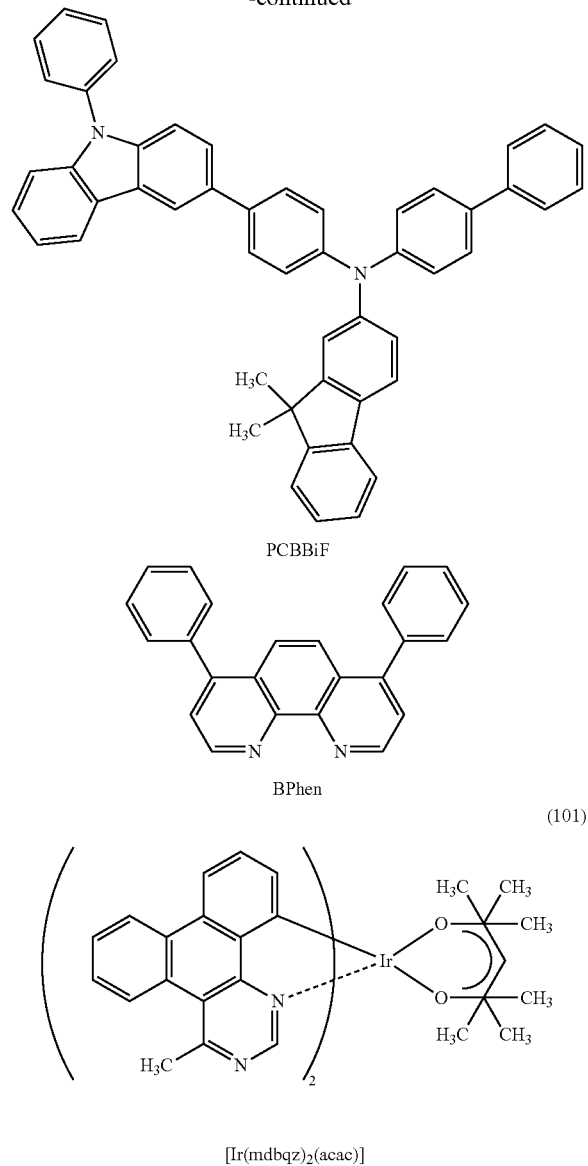

<<Fabrication of Light-Emitting Element 2>>

First, indium tin oxide (ITO) was deposited over a glass substrate 900 by a sputtering method, so that a first electrode 901 which functions as an anode was formed. Note that the thickness of the first electrode 901 was set to 110 nm and that the area of the first electrode 901 was set to 2 mm×2 mm.

Next, as pretreatment for fabricating Light-emitting Element 2 over the substrate 900, a surface of the substrate was washed with water, baking was performed at 200° C. for 1 hour, and then UV ozone treatment was performed for 370 seconds.

After that, the substrate 900 was transferred into a vacuum evaporation apparatus in which the pressure had been reduced to approximately $10^{-4}$ Pa, subjected to vacuum baking at 170° C. for 30 minutes in a heating chamber of the vacuum evaporation apparatus, and then cooled down for approximately 30 minutes.

Next, the substrate 900 was fixed to a holder provided in the vacuum evaporation apparatus so that the surface of the substrate 900 over which the first electrode 901 was formed faced downward. In this example, the case will be described where a hole-injection layer 911, a hole-transport layer 912, a light-emitting layer 913, an electron-transport layer 914, and an electron-injection layer 915 which are included in an EL layer 902 are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2; in this manner, the hole-injection layer 911 was formed on the first electrode 901. The thickness of the hole-injection layer 911 was set to 20 nm. Note that co-evaporation is an evaporation method in which a plurality of different substances are concurrently vaporized from their respective evaporation sources.

Then, 4-phenyl-4'-(9-phenylfluoren-9-yl)triphenylamine (abbreviation: BPAFLP) was deposited by evaporation to a thickness of 20 mu, so that the hole-transport layer 912 was formed.

Next, the light-emitting layer 913 was formed on the hole-transport layer 912 in the following manner. By co-evaporation, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-9,9-dimethyl-N-[4-(9-phenyl-9H-carbazol-3-yl)phenyl]-9H-fluor en-2-amine (abbreviation: PCBBiF), and [Ir(mdbqz)$_2$(dpm)] were deposited to a thickness of 20 nm so that the mass ratio of 2mDBTBPDBq-II to PCBBiF and [[Ir(mdbqz)$_2$(dpm)] was 0.7:0.3:0.05. Then, 2mDBTBPDBq-II, PCBBiF, and [Ir(mdbqz)$_2$(dpm)] were deposited by co-evaporation to a thickness of 20 nm so that the mass ratio of 2mDBTBPDBq-II to PCBBiF and [Ir(mdbqz)$_2$(dpm)] was 0.8:0.2:0.05.

Next, the electron-transport layer 914 was formed in such a manner that 2mDBTBPDBq-II was deposited by evaporation on the light-emitting layer 913 to a thickness of 20 nm and then bathophenanthroline (abbreviation: BPhen) was deposited by evaporation to a thickness of 10 nm. Furthermore, lithium fluoride was deposited by evaporation to a thickness of 1 nm on the electron-transport layer 914, so that the electron-injection layer 915 was formed.

Finally, aluminum was deposited by evaporation to a thickness of 200 nm on the electron-injection layer 915 to form a second electrode 903 serving as a cathode. In this manner, Light-emitting Element 2 was fabricated. Note that in all of the above evaporation steps, evaporation was performed by a resistance-heating method.

Table 4 shows the element structure of Light-emitting Element 2 fabricated as described above.

TABLE 4

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 2 | ITO (110 nm) | DBT3P-II:MoOx (4:2 20 nm) | BPAFLP (20 nm) | * | 2mDBTBPDBq-II (20 nm) | BPhen (10 nm) | LiF (1 nm) | Al (200 nm) |

* 2mDBTBPDBq-II:PCBBiF:[Ir(mdbqz)$_2$(dpm)] (0.7:0.3:0.05 20 nm\0.8:0.2:0.05 20 nm)

Light-emitting Element 2 was sealed in a glove box under a nitrogen atmosphere so as not to be exposed to the air (specifically, a sealant was applied to surround the element, and at the time of sealing, UV treatment was performed and heat treatment was performed at 80° C. for 1 hour).

<<Operation Characteristics of Light-Emitting Element 2>>

The operation characteristics of Light-emitting Element 2 were measured. Note that the measurements were performed at room temperature (in an atmosphere kept at 25° C.).

Figure 28:
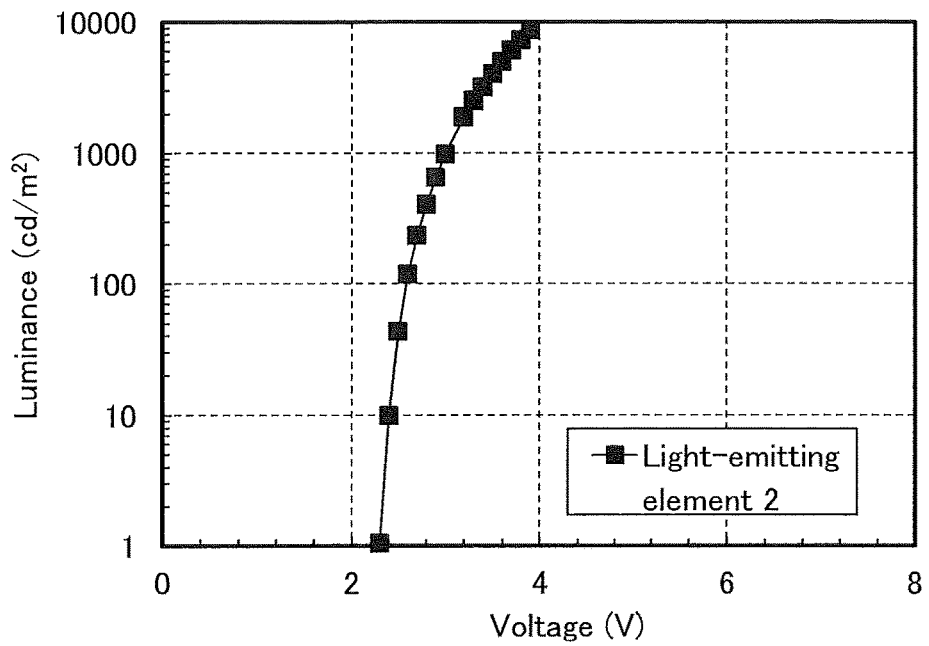
FIG. 28 is a graph showing the voltage-luminance characteristics of Light-emitting Element 2.
Figure 29:
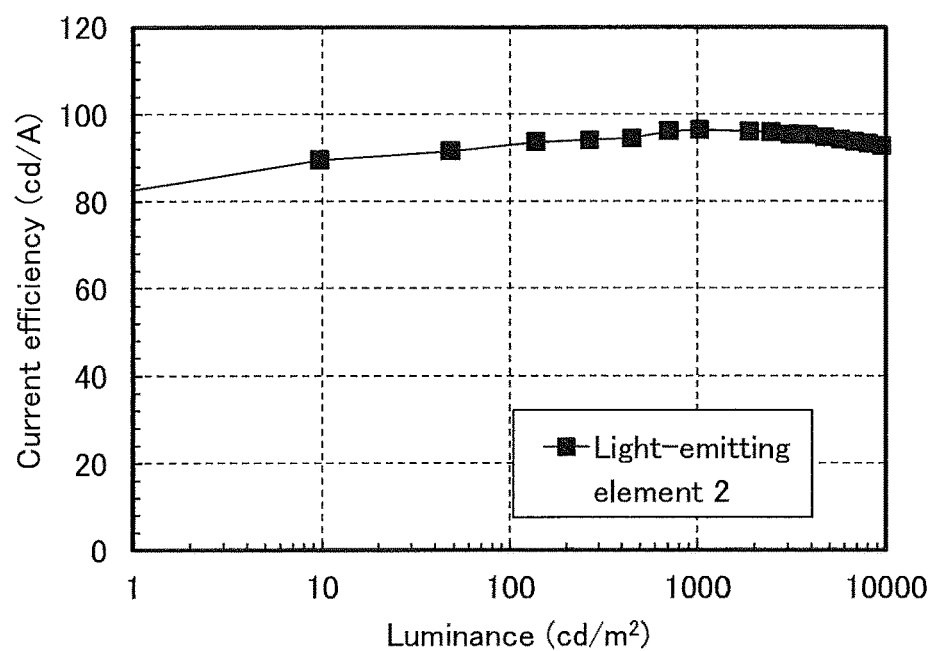
FIG. 29 is a graph showing the luminance-current efficiency characteristics of Light-emitting Element 2.

FIG. 28 shows the voltage-luminance characteristics of Light-emitting Element 2. FIG. 29 shows the luminance-current efficiency characteristics of Light-emitting Element 2.

These results reveal that Light-emitting Element 2 of one embodiment of the present invention has high efficiency. Table 5 shows initial values of main characteristics of Light-emitting Element 2 at a luminance of about 1000 cd/m².

TABLE 5

| | Voltage (V) | Current (mA) | Current Density (mA/cm²) | Chromaticity (x, y) | Luminance (cd/m²) | Current Efficiency (cd/A) | Power Efficiency (lm/W) | External Quantum Efficiency (%) |
|---|---|---|---|---|---|---|---|---|
| Light-emitting Element 2 | 3.0 | 0.041 | 1.0 | (0.44, 0.55) | 990 | 97 | 100 | 27 |

The above results reveal that Light-emitting Element 2 fabricated in this example is a light-emitting element having high current efficiency.

Figure 30:
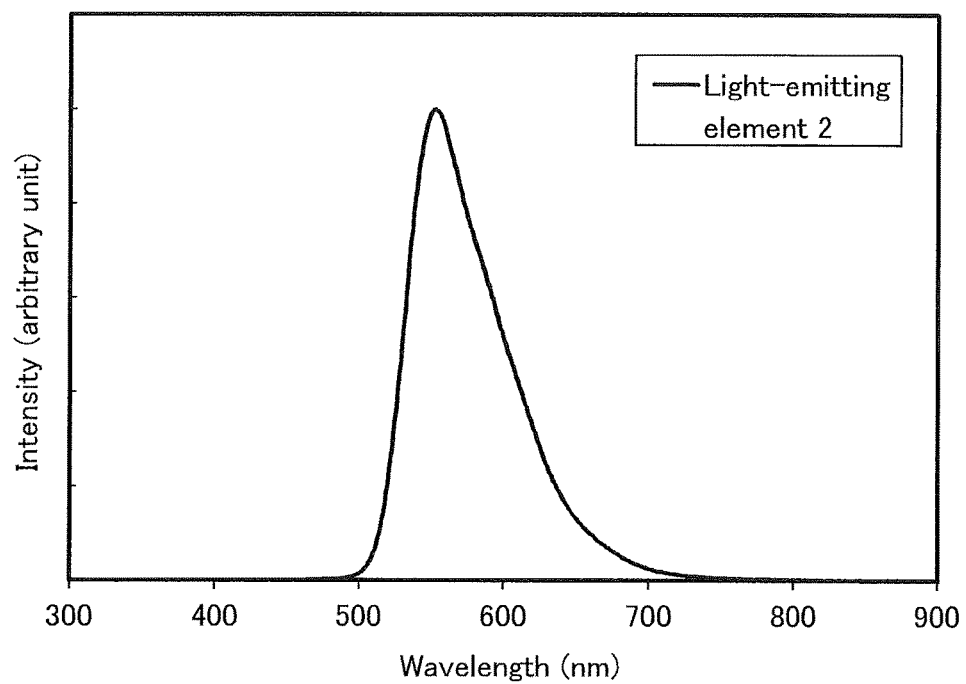
FIG. 30 is a graph showing the emission spectrum of Light-emitting Element 2.

FIG. 30 shows the emission spectrum of Light-emitting Element 2, through which a current flows at a current density of 2.5 mA/cm². As shown in FIG. 30, the emission spectrum of Light-emitting Element 2 has a peak at around 553 nm. It is suggested that the peak is derived from light emission of the organometallic complex [Ir(mdbqz)₂(dpm)] of one embodiment of the present invention.

Figure 31:
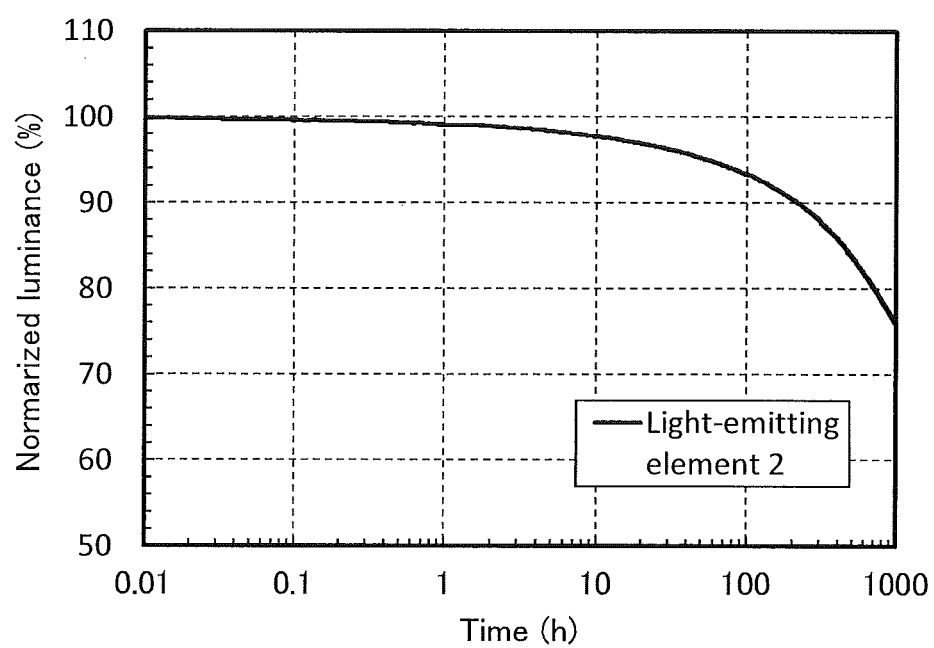
FIG. 31 is a graph showing the reliability of Light-emitting Element 2.

FIG. 31 shows the results of a reliability test on Light-emitting Element 2. In FIG. 31, the vertical axis represents normalized luminance (%) on the assumption that the initial luminance is 100%, and the horizontal axis represents driving time (h) of the element. Note that in the reliability test, Light-emitting Element 2 was driven under the conditions where the initial luminance was set to 5000 cd/m² and the current density was constant. The results show that Light-emitting Element 2 has a long lifetime.

This application is based on Japanese Patent Application serial no. 2014-256995 filed with Japan Patent Office on Dec. 19, 2014, the entire contents of which are hereby incorporated by reference.

What is claimed is:

1. An organometallic complex comprising:

a metal belonging to Group 9 or 10; and a benzo[h] quinazoline skeleton, wherein the benzo[h]quinazoline skeleton comprises a condensed ring sharing a carbon-carbon bond between a 5-position and a 6-position with a benzo[h]quinazoline, and wherein the benzo[h]quinazoline skeleton is bonded to the metal.

2. The organometallic complex according to claim 1, wherein the organometallic complex further comprises a ligand selected from a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two coordinating elements are both nitrogen, and wherein the ligand is bonded to the metal.

3. The organometallic complex according to claim 1, wherein the condensed ring is a substituted or unsubstituted six-membered aromatic ring formed with carbon or both carbon and nitrogen.

4. An organometallic complex comprising a structure represented by Formula (G1),

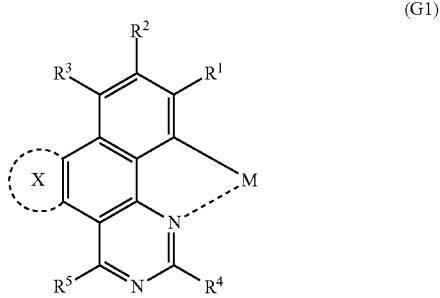

(G1)

wherein M represents a metal belonging to Group 9 or 10, wherein each of R¹ to R⁴ independently represents hydrogen, a substituted or unsubstituted alkyl group having 1 to 6 carbon atoms, or a substituted or unsubstituted aryl group having 6 to 10 carbon atoms, wherein R⁵ represents hydrogen, a substituted or unsubstituted alkyl group having 1 to 6 carbon atoms, or a substituted or unsubstituted phenyl group, and wherein a ring X represents a substituted or unsubstituted six-membered aromatic ring formed with carbon or both carbon and nitrogen.

5. The organometallic complex according to claim 4, wherein the organometallic complex is represented by Formula (G2),

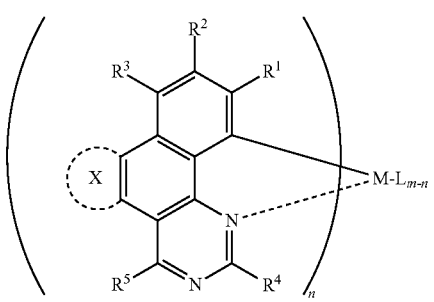
(G2)

wherein M represents a metal belonging to Group 9 or 10, wherein L represents a monoanionic ligand, wherein each of $R^1$ to $R^4$ independently represents hydrogen, a substituted or unsubstituted alkyl group having 1 to 6 carbon atoms, or a substituted or unsubstituted aryl group having 6 to 10 carbon atoms, wherein $R^5$ represents hydrogen, a substituted or unsubstituted alkyl group having 1 to 6 carbon atoms, or a substituted or unsubstituted phenyl group, wherein a ring X represents a substituted or unsubstituted six-membered aromatic ring formed with carbon or both carbon and nitrogen, wherein m is 3 and n is 1, 2, or 3, when the metal belongs to Group 9, and wherein m is 2 and n is 1 or 2, when the metal belongs to Group 10.

6. The organometallic complex according to claim 5, wherein the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two coordinating elements are both nitrogen.

7. The organometallic complex according to claim 5, wherein the monoanionic ligand is represented by any of Formulae (L1) to (L7),

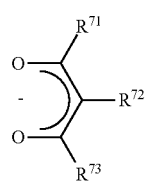
(L1)

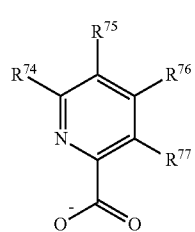
(L2)

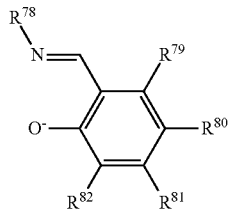
(L3)

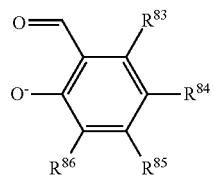
(L4)

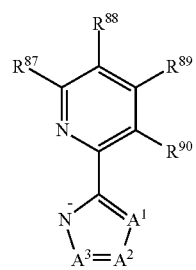
(L5)

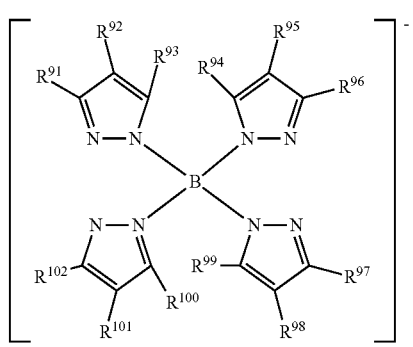
(L6)

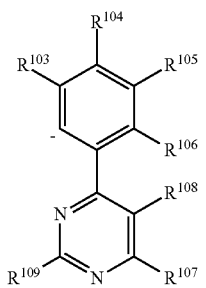
(L7)

wherein each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms, and wherein each of $A^1$ to $A^3$ independently represents nitrogen, sp$^2$ hybridized carbon bonded to hydrogen, or sp$^2$ hybridized carbon having a substituent, the substituent being an alkyl group having 1 to 6 carbon atoms, a halogen group, a haloalkyl group having 1 to 6 carbon atoms, or a phenyl group.

8. The organometallic complex according to claim 4, wherein the organometallic complex is represented by Formula (G3),

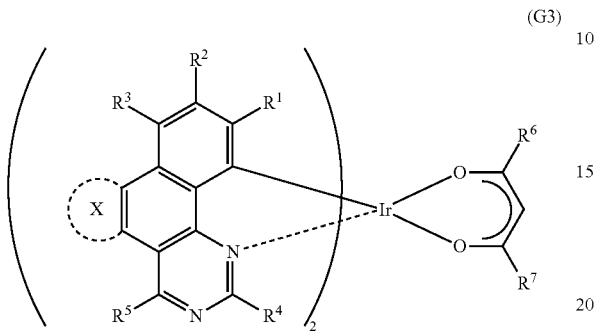

(G3)

wherein each of R¹ to R⁴ independently represents hydrogen, a substituted or unsubstituted alkyl group having 1 to 6 carbon atoms, or a substituted or unsubstituted aryl group having 6 to 10 carbon atoms,
wherein R⁵ represents hydrogen, a substituted or unsubstituted alkyl group having 1 to 6 carbon atoms, or a substituted or unsubstituted phenyl group,
wherein each of R⁶ and R⁷ independently represents hydrogen or a substituted or unsubstituted alkyl group having 1 to 6 carbon atoms, and
wherein a ring X represents a substituted or unsubstituted six-membered aromatic ring formed with carbon or both carbon and nitrogen.

9. The organometallic complex according to claim 4, wherein the organometallic complex is represented by Formula (G4),

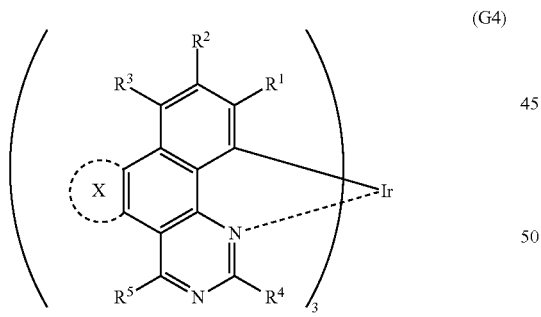

(G4)

wherein each of R¹ to R⁴ independently represents hydrogen, a substituted or unsubstituted alkyl group having 1 to 6 carbon atoms, or a substituted or unsubstituted aryl group having 6 to 10 carbon atoms,
wherein R⁵ represents hydrogen, a substituted or unsubstituted alkyl group having 1 to 6 carbon atoms, or a substituted or unsubstituted phenyl group, and
wherein a ring X represents a substituted or unsubstituted six-membered aromatic ring formed with carbon or both carbon and nitrogen.

10. The organometallic complex according to claim 4, wherein the organometallic complex is represented by any one of Formulae (100), (101), (104), and (114),

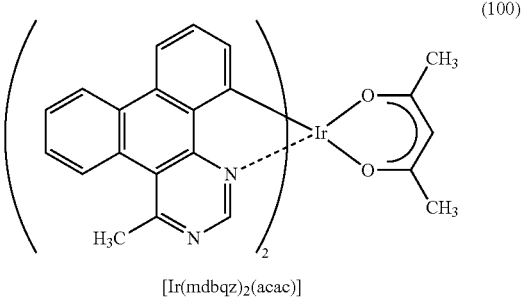

(100)

[Ir(mdbqz)₂(acac)]

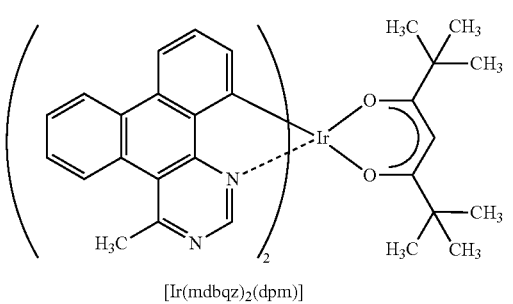

(101)

[Ir(mdbqz)₂(dpm)]

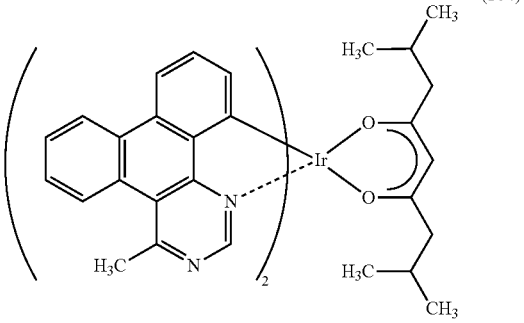

(104)

[Ir(mdbqz)₂(divm)]

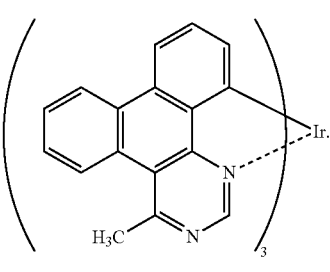

(114)

[Ir(mdbqz)₃]

11. A light-emitting element comprising an electroluminescence layer between a pair of electrodes, the electroluminescence layer comprising the organometallic complex according to claim 4.

12. A light-emitting device comprising:
the light-emitting element according to claim 11; and
at least one of a transistor and a substrate.

13. An electronic device comprising:
the light-emitting device according to claim 12; and
at least one of a microphone, a camera, an operation button, an external connection portion, and a speaker.

14. A lighting device comprising:
the light-emitting device according to claim 12; and
a housing.

* * * * *